US 6,642,227 B2

(12) United States Patent
Cao et al.

(10) Patent No.: US 6,642,227 B2
(45) Date of Patent: Nov. 4, 2003

(54) INHIBITORS OF C-JUN N-TERMINAL KINASES (JNK) AND OTHER PROTEIN KINASES

(75) Inventors: Jingrong Cao, Newton, MA (US); Jeremy Green, Burlington, MA (US); Young-Choon Moon, Lexington, MA (US); Jian Wang, Boston, MA (US); Mark Ledeboer, Acton, MA (US); Edmund Harrington, South Boston, MA (US); Huai Gao, Natick, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 50 days.

(21) Appl. No.: 10/121,035

(22) Filed: Apr. 10, 2002

(65) Prior Publication Data

US 2003/0096816 A1 May 22, 2003

Related U.S. Application Data

(60) Provisional application No. 60/283,621, filed on Apr. 13, 2001, provisional application No. 60/329,440, filed on Oct. 15, 2001, and provisional application No. 60/292,974, filed on May 23, 2001.

(51) Int. Cl.[7] .................... C07D 409/04; C07D 409/14; A61K 31/381
(52) U.S. Cl. ................ 514/227.8; 514/235.8; 514/252.19; 514/275; 544/60; 544/122; 544/331
(58) Field of Search .......... 544/60, 122, 331; 514/227.8, 235.8, 252.19, 275

(56) References Cited

U.S. PATENT DOCUMENTS

| 4,940,712 A | 7/1990 | Walker et al. ............... 514/272 |
| 5,932,576 A | 8/1999 | Anantanarayan et al. 514/235.5 |
| 6,051,574 A | 4/2000 | Anthony ..................... 514/247 |
| 6,114,333 A | 9/2000 | Davis et al. ................. 514/252 |

FOREIGN PATENT DOCUMENTS

| WO | WO 95/19358 | 7/1995 |
| WO | WO 97/03967 | 2/1997 |
| WO | WO 97/09325 | 3/1997 |
| WO | WO 98/28282 | 7/1998 |
| WO | WO 01/12621 | * 2/2001 |
| WO | WO 01/29009 | 4/2001 |

OTHER PUBLICATIONS

Casanova et al., PubMed Abstract [Rev. Neurol. 28(9):909–15], May 1999.*
Simone, Oncology: Introduction, Cecil Textbook of Medicine, 20th Edition, vol. 1, pp. 1004–1010, 1996.*
Traxler, Review: Oncologic, Endocrine & Metabolic. Protein Tyrosine kinase inhibitors in cancer treatment, Exp. Opin. Ther. Patents, 7(6), pp. 571–588, 1997.*
Layzer, Degenerative Diseases of the Nervous System, Cecil Textbook of Medicine, 20th Edition, vol. 2, pp. 2050–2057, 1996.*
Damasio, Alzheimer's Disease and Related Dementias, Cecil Textbook of Medicine, 20th Edition, vol. 2, pp. 1992–1996, 1996.*

* cited by examiner

*Primary Examiner*—Deepak Rao
(74) *Attorney, Agent, or Firm*—Andrea L. C. Robidoux; Vertex Pharmaceuticals Incorporated

(57) ABSTRACT

The present invention provides compounds of formula I:

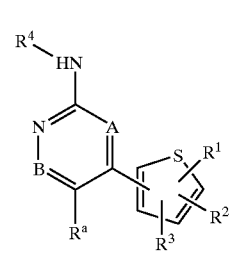

or a pharmaceutically acceptable derivative o thereof, wherein A, B, $R^a$, $R^1$, $R^2$, $R^3$, and $R^4$ are as described in the specification. These compounds are inhibitors of protein kinase, particularly inhibitors of JNK, a mammalian protein kinase involved cell proliferation, cell death and response to extracellular stimuli; Lck and Src kinase. The invention also relates to methods for producing these inhibitors. The invention also provides pharmaceutical compositions comprising the inhibitors of the invention and methods of utilizing those compositions in the treatment and prevention of various disorders.

31 Claims, No Drawings

INHIBITORS OF C-JUN N-TERMINAL KINASES (JNK) AND OTHER PROTEIN KINASES

CROSS REFERENCE TO RELATED APPLICATIONS

This application claims benefit of priority to U.S. provisional applications 60/283,621 filed Apr. 13, 2001, 60/329,440 filed Oct. 15, 2001 and 60/292,974 filed May 23, 2001.

TECHNICAL FIELD OF INVENTION

The present invention relates to inhibitors of protein kinase, especially c-Jun N-terminal kinases (JNK) and the Src-family of kinases, including Lck, which are members of the mitogen-activated protein (MAP) kinase family. JNK, Src, and Lck have been implicated in a number of different human diseases. The invention also provides pharmaceutical compositions comprising the inhibitors of the invention and methods of utilizing those compositions in the treatment and prevention of various disorders in which JNK, Src, and Lck play a role.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

One particularly interesting kinase family are the c-Jun $NH_2$-terminal protein kinases, also known as JNKs. Three distinct genes, JNK1, JNK2, JNK3 have been identified and at least ten different splicing isoforms of JNKs exist in mammalian cells [Gupta et al., *EMBO J.*, 15:2760–70 (1996)]. Members of the JNK family are activated by proinflammatory cytokines, such as tumor necrosis factor-α (TNFα) and interleukin-1 β (IL-1β), as well as by environmental stress, including anisomycin, UW irradiation, hypoxia, and osmotic shock [Minden et al., *Biochemica et Biophysica Acta*, 1333:F85–F104 (1997)].

The down-Stream substrates of JNKs include transcription factors c-Jun, ATF-2, Elk1, p53 and a cell death domain protein (DENN) [Zhang et al. *Proc. Natl. Acad. Sci. USA*, 95:2586–91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [*Nat. Genet.* 21:326–9 (1999); *FEBS Lett.* 420:201–4 (1997); *J. Clin. Invest.* 102:1942–50 (1998); *Hepatology* 28:1022–30 (1998)]. Therefore, inhibitors of JNK may be useful to treat various hepatic disorders.

A role for JNK in cardiovascular disease such as myocardial infarction or congestive heart failure has also been reported as it has been shown JNK mediates hypertrophic responses to various forms of cardiac stress [*Circ. Res.* 83:167–78 (1998); *Circulation* 97:1731–7 (1998); *J. Biol. Chem.* 272:28050–6 (1997); *Circ. Res.* 79:162–73 (1996); *Circ. Res.* 78:947–53 (1996); *J. Clin. Invest.* 97:508–14 (1996)].

It has been demonstrated that the JNK cascade also plays a role in T-Cell activation, including activation of the IL-2 promoter. Thus, inhibitors of JNK may have therapeutic value in altering pathologic immune responses [*J. Immunol.* 162:3176–87 (1999); *Eur. J. Immunol.* 28:3867–77 (1998); *J. Exp. Med.* 186:941–53 (1997); *Eur. J. Immunol.* 26:989–94 (1996)].

A role for JNK activation in various cancers has also been established, suggesting the potential use of JNK inhibitors in cancer. For example, constitutively activated JNK is associated with HTLV-1 mediated tumorigenesis [*Oncogene* 13:135–42 (1996)]. JNK may play a role in Kaposi's sarcoma (KS) because it is thought that the proliferative effects of bFGF and OSM on KS cells are mediated by their activation of the JNK signaling pathway [*J. Clin. Invest.* 99:1798–804 (1997)]. Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [*Blood* 92:2450–60 (1998)].

JNK1 and JNK2 are widely expressed in a variety of tissues. In contrast, JNK3, is selectively expressed in the brain and to a lesser extent in the heart and testis [Gupta et al., supra; Mohit et al., *Neuron* 14:67–78 (1995); Martin et al., *Brain Res. Mol. Brain Res.* 35:47–57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the LNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature*, 389:865–870 (1997)].

Based on these findings, JNK signalling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

The Src-family of kinases are implicated in cancer, immune system dysfunction, and bone remodeling diseases. For general reviews, see Thomas and Brugge, *Annu. Rev. Cell Dev. Biol.* (1997) 13, 513; Lawrence and Niu, *Pharmacol. Ther.* (1998) 77, 81; Tatosyan and Mizenina, *Biochemistry* (Moscow) (2000) 65, 49; Boschelli et al., *Drugs of the Future* 2000, 25(7), 717, (2000).

Members of the Src family include the following eight kinases in mammals: Src, Fyn, Yes, Fgr, Lyn, Hck, Lck, Blk and Yrc. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 65, 49–58 (2000).

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell*, 69, 551 (1992) and Soriano et al., *Cell*, 64, 693 (1991).

Suppression of arthritic bone destruction has been achieved by the overexpression of CSK in rheumatoid synoviocytes and osteoclasts. Takayanagi et al., *J. Clin. Invest.*, 104, 137 (1999). CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717, (2000).

Src also plays a role in the replication of hepatitis B virus. The virally encoded transcription factor HBx activates Src in a step required for propagation of the virus. Klein et al., *EMBO J.*, 18, 5019, (1999) and Klein et al., *Mol. Cell. Biol.*, 17, 6427 (1997).

A number of studies have linked Src expression to cancers such as colon, breast, hepatic and pancreatic cancer, certain B-Cell leukemias and lymphomas. Talamonti et al., *J. Clin. Invest.*, 91, 53 (1993); Lutz et al., *Biochem. Biophys. Res.* 243, 503 (1998); Rosen et al., *J. Biol. Chem.*, 261, 13754 (1986); Bolen et al., *Proc. Natl. Acad. Sci. USA*, 84, 2251 (1987); Masaki et al., *Hepatology*, 27, 1257 (1998); Biscardi et al., *Adv. Cancer Res.*, 76, 61 (1999); Lynch et al., *Leukemia*, 7, 1416 (1993). Furthermore, antisense Src expressed in ovarian and colon tumor cells has been shown to inhibit tumor growth. Wiener et al., *Clin. Cancer Res.*, 5, 2164 (1999); Staley et al., *Cell Growth Diff.*, 8, 269 (1997).

Other Src family kinases are also potential therapeutic targets. Lck plays a role in T-Cell signaling. Mice that lack the Lck gene have a poor ability to develop thymocytes. The function of Lck as a positive activator of T-Cell signaling suggests that Lck inhibitors may be useful for treating autoimmune disease such as rheumatoid arthritis. Molina et al., *Nature*, 357, 161 (1992). Hck, Fgr and Lyn have been identified as important mediators of integrin signaling in myeloid leukocytes. Lowell et al., *J. Leukoc. Biol.*, 65, 313 (1999). Inhibition of these kinase mediators may therefore be useful for treating inflammation. Boschelli et al., *Drugs of the Future* 2000, 25(7), 717, (2000).

Accordingly, there is still a great need to develop potent inhibitors of JNKs and Src family kinases that are useful in treating various conditions associated with JNK and Src activation.

SUMMARY OF THE INVENTION

The present invention provides compounds of formula I:

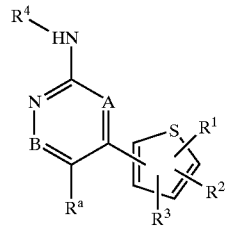

I wherein $R^1$, $R^2$, $R^3$, $R^4$, and $R^a$ are as described below.

The present invention also provides a pharmaceutical composition comprising a compound of formula I.

The compounds and pharmaceutical compositions of the present invention are useful as inhibitors of c-Jun N-terminal kinases (JNK) and Src family kinases, including Src and Lck. Thus, they are also useful in methods for treating or preventing a variety of disorders, such as heart disease, immunodeficiency disorders, inflammatory diseases, allergic diseases, autoimmune diseases, destructive bone disorders such as osteoporosis, proliferative disorders, infectious diseases and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation and neurodegenerative disorders.

DETAILED DESCRIPTION OF THE INVENTION

The present invention provides a compound of formula I:

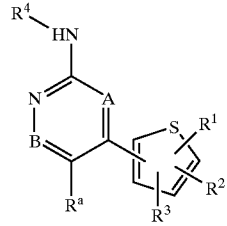

I or a pharmaceutically acceptable derivative thereof, wherein:

A and B are each independently selected from N or CH;
$R^1$ and $R^2$ are each independently selected from halogen, CN, $NO_2$, $N(R)_2$, OR, SR, or $(T)_n$—$R^5$;
$R^3$ is selected from a 3–6 membered carbocyclic or heterocyclic ring having one to two heteroatoms independently selected from nitrogen, oxygen, or sulfur, phenyl, or a 5–6 membered heteroaryl ring having one to three heteroatoms independently selected from nitrogen, oxygen, or sulfur, wherein said phenyl or heteroaryl ring is optionally substituted with one $(T)_n$—Ar and one to two $R^7$;
each n is independently selected from zero or one;

T is a $C_1$–$C_6$ alkylidene chain, wherein one methylene unit of T is optionally replaced by CO, $CO_2$, COCO, CONR, OCONR, NRNR, NRNRCO, NRCO, $NRCO_2$, NRCONR, $SO_2$, $NRSO_2$, $SO_2NR$, $NRSO_2NR$, O, S, or NR;

each R is independently selected from hydrogen or an optionally substituted $C_1$–$C_6$ aliphatic group; or two R on the same nitrogen atom may be taken together with the nitrogen to form a four to eight membered, saturated or unsaturated heterocyclic ring containing one to three heteroatoms independently selected from nitrogen, oxygen, or sulfur;

$R^4$ is $(T)_n$—R, $(T)_n$—Ar, or $(T)_n$—$Ar^1$;

$R^a$ is selected from $R^b$, halogen, $NO_2$, $OR^b$, $SR^b$, or $N(R^b)_2$;

$R^b$ is selected from hydrogen or a $C_1$–$C_4$ aliphatic group optionally substituted with oxo, OH, SH, $NH_2$, halogen, $NO_2$, or CN;

$R^5$ is an optionally substituted $C_1$–$C_6$ aliphatic or Ar;

Ar is a 5–6 membered saturated, partially unsaturated, or aryl monocyclic ring having zero to three heteroatoms independently selected from nitrogen, sulfur, or oxygen, or an 8–10 membered saturated, partially unsaturated, or aryl bicyclic ring having zero to four heteroatoms independently selected from nitrogen, sulfuri or oxygen, wherein Ar is optionally substituted with one to three $R^7$;

$Ar^1$ is a 6-membered aryl ring having zero to two nitrogens, wherein said ring is substituted with one Z—$R^6$ group and optionally substituted with one to three $R^7$;

Z is a $C_1$–$C_6$ alkylidene chain wherein up to two non-adjacent methylene units of Z are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; provided that said optionally replaced methylene unit of Z is a methylene unit non-adjacent to $R^6$;

$R^6$ is selected from Ar, R, halogen, $NO_2$, CN, OR, SR, $N(R)_2$, NRC(O)R, $NRC(O)N(R)_2$, $NRCO_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or C(O)$CH_2$C(O)R; and each $R^7$ is independently selected from R, halogen, $NO_2$, CN, OR, SR, $N(R)_2$, NRC(O)R, $NRC(O)N(R)_2$, $NRCO_2R$, C(O)R, $CO_2R$, $C(O)N(R)_2$, $OC(O)N(R)_2$, SOR, $SO_2R$, $SO_2N(R)_2$, $NRSO_2R$, $NRSO_2N(R)_2$, C(O)C(O)R, or C(O)$CH_2$C(O)R; or two $R^7$ on adjacent positions of $Ar^1$ may be taken together to form a saturated, partially unsaturated, or fully unsaturated five to seven membered ring containing zero to three heteroatoms selected from O, S, or N.

The following abbreviations are used throughout the specifications (including in chemical formulae):
iPr=isopropyl
t-Bu or tBu=tert-butyl
Et=ethyl
Me=methyl
Cbz=benzoyloxycarbonyl
BOC=tert-butyloxycarbonyl
Ph=phenyl
Bn=benzyl
DMF=N,N-dimethylformamide
THF=tetrahydrofuran
DCM=dichloromethane
DMF-DMA=N,N-dimethylformamide-dimethylacetal
DMSO-dimethylsulfoxide
TLC=thin layer chromatography As used herein, the following definitions shall apply unless otherwise indicated.

The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl) alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-Substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 7 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl, heteroaryl, aralkyl, or heteroaralkyl group are selected from halogen, —R°, —OR°, —SR°, 1,2-methylene-dioxy, 1,2-ethylenedioxy, phenyl (Ph) optionally substituted with R°, —O(Ph) optionally substituted with R°, —CH$_2$(Ph) optionally substituted with R°, —CH$_2$CH$_2$(Ph), optionally substituted with R°, —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, or —(CH$_2$)$_y$NHC(O)R°, wherein each R° is independently selected from hydrogen, optionally substituted C$_{1-6}$ aliphatic, an unsubstituted 5–6 membered heteroaryl or heterocyclic ring, phenyl, —O(Ph), or —CH$_2$(Ph). Optional substituents on the aliphatic group of R° are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo C$_{1-4}$ aliphatic.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic).

Optional substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted-CH$_2$CH$_2$(Ph), or an unsubstituted 5–6 membered heteroaryl or heterocyclic ring. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic).

The term "alkylidene chain" refers to a straight or branched carbon chain that may be fully saturated or have one or more units of unsaturation.

A combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Preferred R$^1$ groups of formula I are selected from N(R)$_2$, OR, SR, or (T)$_n$—R$^5$ wherein T is a C$_{1-4}$ alkylidene chain and wherein one methylene unit of T is optionally replaced by S, O, N(R), or CO$_2$. More preferred RI groups of formula I are selected from SCH$_2$-4-phenol, SCH$_3$, OH, OEt, N-(Me)$_2$, OMe, 4-methylpiperidin-1-yl, NHEt, NHCH$_2$CH$_2$-piperidin-1-yl, or NHCH$_2$CH$_2$morpholin-4-yl.

Preferred R$^2$ groups of formula I are selected from CN, R$^5$, halogen, CO$_2$R$^5$, or N(R)$_2$. More preferred R$^2$ groups are selected from CN or CO$_2$R$^5$.

Preferred R$^3$ groups of formula I are selected from 5–6 membered ring selected from carbocyclic, phenyl, or a heterocyclyl or heteroaryl ring having one to two heteroatoms independently selected from nitrogen, oxygen or sulfur, wherein R$^3$ is optionally substituted with one (T)$_n$—Ar group and one R$^7$. More preferred R$^3$ groups of formula I are selected from phenyl, pyridyl, pyrimidinyl, cyclohexyl, and furanyl. Preferred substituents on R$^3$ are selected from (T)$_n$—Ar or R$^7$ wherein Ar is a an optionally substituted 5–6 membered aryl ring having zero to two heteroatoms independently selected from nitrogen, oxygen, or sulfur, and wherein R$^7$ is selected from R, halogen, OR, N(R)$_2$, or CO$_2$R. More preferred substituents on R$^3$ are selected from phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, halogen, such as chloro, bromo, and fluoro, haloalkyl such as trifluoromethyl, OH, NH$_2$, alkyl, such as methyl, and alkoxy, such as methoxy and ethoxy.

Preferred R$^4$ groups of formula I are selected from hydrogen or Ar wherein Ar is an optionally substituted 6 membered saturated, partially saturated, or aryl ring having zero to two heteroatoms independently selected from nitrogen, oxygen, or sulfur. More preferred R$^4$ groups of formula I are selected from phenyl, benzyl, pyridyl, piperidinyl, and cyclohexyl. Preferred substituents on R$^4$ are selected from CO$_2$R, OR, OAr, halogen, NRSO$_2$R, SO$_2$N(R)$_2$, NRCON(R)$_2$, NO$_2$, or N(R)$_2$. More preferred substituents of R$^4$ are selected from benzyloxy, phenoxy, SO$_2$NH$_2$, OH, NO$_2$, NH$_2$, OMe, Br, Cl, CO$_2$Me, NHSO$_2$Me, NHSO$_2$Et, NHCON(Me)$_2$, NHCON(Et)$_2$, NHCOpyrrolidin-1-yl, or NHCOmorpholin-4-yl.

Most preferred R$^4$ groups of formula I are those wherein R$^4$ is Ar$^1$. Preferred Z—R$^6$ groups of the Ar$^1$ group of formula I are those wherein Z is a C$_{1-4}$ alkylidene chain wherein one methylene unit of Z is optionally replaced by O, NH, NHCO, NHCO$_2$, NHSO$_2$, CONH, and wherein R$^6$ is selected from N(R)$_2$, NHCOR, or Ar wherein Ar is a 5–6 membered heterocyclic or heteroaryl ring having one to two heteroatoms independently selected from nitrogen, oxygen, or sulfur. The Ar group of R$^6$ is optionally substituted with R, OR, N(R)$_2$, or oxo. More preferred Z—R$^6$ groups of formula I are selected from O(CH$_2$)$_3$OH, O(CH$_2$)$_3$NH(CH$_2$)$_2$OH, O(CH$_2$)$_2$NH(CH$_2$)$_2$OH, O(CH$_2$)$_3$N(hydroxyethyl)(methyl), O(CH$_2$)$_3$pyrrolidin-1-yl, O(CH$_2$)$_2$morpholin-4-yl, O(CH$_2$)$_3$N(Me)$_2$, O(CH$_2$)$_3$N(Et)$_2$, O(CH$_2$)$_3$(4-hydroxyethylpiperazin-1-yl), O(CH$_2$)$_3$piperazin-1-yl,O (CH₂)₃(4-hydroxymethylpiperidin-1-yl), O(CH₂)₃(4-hydroxypiperidin-1-yl), NHCO(CH₂)₃N(Me)₂, NHCO(CH₂)₃NCOCH₃, NHCOCH₂pyridin-2-yl, NHCOCH₂(2-aminothiazol-4-yl), NHCOCH₂cyclopropyl, NHCO(CH₂)₂N(Et)₂, NHCO(CH₂)₂(piperazin-2,5-dione-3-yl), NHCOpyrrolidin-1-yl, NHCOmorpholin-4-yl, NHCO₂CH₂tetrahydrofuran-2-yl, NHCO₂tetrahydrofuran-2-yl, NHCO₂tetrahydropyran-4-yl, or NHCO₂CH₂tetrahydropyran-2-yl.

Preferred R$^a$ groups of formula I are selected from R$^b$, OR$^b$, SR$^b$, or N (R$^b$)₂. More preferred R$^a$ groups of formula I are selected from methyl, OH, OMe, or NH₂.

One embodiment of this invention relates to compounds of formula IIa:

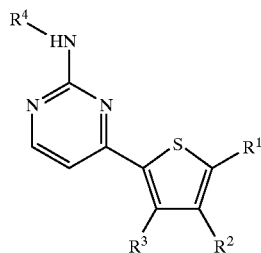

IIa or a pharmaceutically acceptable derivative thereof, wherein R¹, R², R³, and R⁴ are as described above.

Preferred R¹ groups of formula IIa are selected from N(R)₂, OR, SR, or (T)$_n$—R⁵ wherein T is a C$_{1-4}$ alkylidene chain and wherein one methylene unit of T is optionally replaced by S, O, N(R), or CO₂. More preferred R¹ groups of formula IIa are selected from SCH₂-4-phenol, SCH₃, OH, OEt, N(Me)₂, OMe, 4-methylpiperidin-1-yl, NHEt, NHCH₂CH₂piperidin-1-yl, or NHCH₂CH₂morpholin-4-yl.

Preferred R² groups of formula IIa are selected from CN, R⁵, halogen, CO₂R⁵, or N(R)₂. More preferred R² groups are selected from CN or CO₂R⁵.

Preferred R³ groups of formula IIa are selected from 5–6 membered ring selected from carbocyclic, phenyl, or a heterocyclyl or heteroaryl ring having one to two heteroatoms independently selected from nitrogen, oxygen or sulfur, wherein R³ is optionally substituted with one (T)$_n$—Ar group and one R⁷. More preferred R³ groups of formula IIa are selected from phenyl, pyridyl, pyrimidinyl, cyclohexyl, and furanyl. Preferred substituents on R³ are selected from (T)$_n$—Ar or R⁷ wherein Ar is a an optionally substituted 5–6 membered aryl ring having zero to two heteroatoms independently selected from nitrogen, oxygen, or sulfur, and wherein R⁷ is selected from R, halogen, OR, N(R)₂, or CO₂R. More preferred substituents on R³ are selected from phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, halogen, such as chloro, bromo, and fluoro, haloalkyl such as trifluoromethyl, OH, NH₂, alkyl, such as methyl, and alkoxy, such as methoxy and ethoxy.

Preferred R⁴ groups of formula IIa are selected from hydrogen or Ar wherein Ar is an optionally substituted 6 membered saturated, partially saturated, or aryl ring having zero to two heteroatoms independently selected from nitrogen, oxygen, or sulfur. More preferred R⁴ groups of formula IIa are selected from phenyl, benzyl, pyridyl, piperidinyl, and cyclohexyl. Preferred substituents on R⁴ are selected from CO₂R, OR, OAr, halogen, NRSO₂R, SO₂N(R)₂, NRCON(R)₂, NO₂, or N(R)₂. More preferred substituents of R⁴ are selected from benzyloxy, phenoxy, SO₂NH₂, OH, NO₂, NH₂, OMe, Br, Cl, CO₂Me, NHSO₂Me, NHSO₂Et, NHCON (Me)₂, NHCON (Et)₂, NHCOpyrrolidin-1-yl, or NHCOmorpholin-4-yl.

Preferred compounds of formula IIa are those having one or more, more preferably more than one, and most preferably all, of the features selected from the group consisting of:

(a) R¹ is selected from N(R)₂, OR, SR, or (T)$_n$—R⁵;
(b) T is a C$_{1-4}$ alkylidene chain, wherein one methylene unit of T is optionally replaced by S, O, N(R), or CO₂;
(c) R² is CN, R, halogen, C₂R⁵, or N(R)₂;
(d) R³ is a 5–6 membered ring selected from carbocyclic, phenyl, or a heterocyclyl or heteroaryl ring having one to two heteroatoms independently selected from nitrogen, oxygen or sulfur, wherein R³ is optionally substituted with one (T)$_n$—Ar group and one R⁷; and
(e) R⁴ is hydrogen or Ar, wherein Ar is an optionally substituted 6 membered saturated, partially saturated, or aryl ring having zero to two heteroatoms independently selected from nitrogen, oxygen, or sulfur.

More preferred compounds of formula IIa are those having one or more, more preferably more than one, and most preferably all, of the features selected from the group consisting of:

(a) R¹ is selected from SCH₂-4-phenol, SCH₃, OH, OEt, N(Me)₂, OMe, 4-methylpiperidin-1-yl, NHEt, NHCH₂CH₂piperidin-1-yl, or NHCH₂CH₂morpholin-4-yl;
(b) R² is CN or C₂R⁵;
(c) R³ is selected from phenyl, pyridyl, pyrimidinyl, cyclohexyl, or furanyl, wherein R³ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, OH, NH₂, methyl, methoxy or ethoxy; and
(d) R⁴ is selected from hydrogen or a phenyl, benzyl, pyridyl, piperidinyl, or cyclohexyl ring, wherein said ring is optionally subsituted with benzyloxy, phenoxy, SO₂NH₂, OH, NO₂, NH₂, OMe, Br, Cl, CO₂Me, NHSO₂Me, NHSO₂Et, NHCON(Me)₂, NHCON(Et)₂, NHCOpyrrolidin-1-yl, or NHCOmorpholin-4-yl.

Another embodiment relates to compounds of formula IIb:

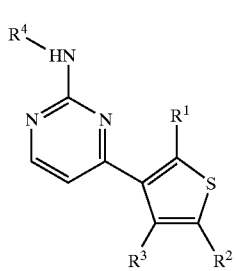

IIb or a pharmaceutically acceptable derivative thereof, wherein R¹, R², R³, and R⁴ are as defined above.

Preferred R¹, R³, and R⁴ groups of formula IIb are those described above for compounds of formula IIa.

Preferred R² groups of formula IIb are CN, R⁷, Ar, halogen, or N(R⁶)₂. When R² is Ar, a preferred Ar group is 4-(C₁₋₃ alkyl)-thiazol-2-yl.

Preferred compounds of formula IIb are those having one or more, more preferably more than one, and most preferably all, of the features selected from the group consisting of:

(a) $R^1$ is selected from N(R)₂, OR, SR, or (T)ₙ—R⁵;

(b) T is a C₁₋₄ alkylidene chain, wherein one methylene unit of T is optionally replaced by S, O, N(R), or CO₂;

(c) $R^2$ is CN, R⁷, Ar, halogen, or N(R⁶)₂;

(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one (T)ₙ—Ar group and one R⁷; and (e) $R^4$ is hydrogen or Ar, wherein Ar is an optionally substituted 6 membered saturated, partially saturated, or aryl ring having zero to two heteroatoms independently selected from nitrogen, oxygen, or sulfur.

More preferred compounds of formula IIb are those having one or more, more preferably more than one, 2and most preferably all, of the features selected from the group consisting of:

(a) $R^1$ is selected from SCH₂-4-phenol, SCH₃, OH, OEt, N(Me)₂, OMe, 4-methylpiperidin-1-yl, NHEt, NHCH₂CH₂piperidin-1-yl, or NHCH₂CH₂morpholin-4-yl;

(b) $R^2$ is CN or 4-(C₁₋₃ alkyl)-thiazol-2-yl;

(c) $R^3$ is selected from phenyl, pyridyl, pyrimidinyl, cyclohexyl, or furanyl, wherein $R^3$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropyl-phenyl, 4-F-3-Cl-phenyl, pyrrolyl, pyrimidinyl, chloro, bromo, fluoro, trifluoromethyl, OH, NH₂, methyl, methoxy or ethoxy; and (d) $R^4$ is selected from hydrogen or a phenyl, benzyl, pyridyl, piperidinyl, or cyclohexyl ring, wherein said ring is optionally subsituted with benzyloxy, phenoxy, SO₂NH₂, OH, NO₂, NH₂, OMe, Br, Cl, CO₂Me, NHSO₂Me, NHSO₂Et, NHCON(Me)₂, NHCON(Et)₂, NHCOpyrrolidin-1-yl, or NHCOmorpholin-4-yl.

Exemplary structures of formula IIa are set forth in Table 1 below.

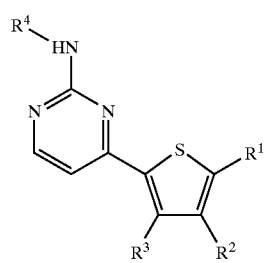

IIa

TABLE 1

Compounds of Formula IIa

| No. IIa- | R¹ | R² | R³ | R⁴ |
|---|---|---|---|---|
| 1 | SMe | CN | 4-CO₂H-phenyl | H |
| 2 | SMe | CN | 4-Cl-phenyl | H |
| 3 | SMe | CN | 4-CF₃-phenyl | H |
| 4 | SMe | CN | 4-CH₃-phenyl | H |
| 5 | SMe | CN | 2-Cl-phenyl | H |
| 6 | SMe | CN | 4-OCH₃-phenyl | H |
| 7 | NHCH₂Ph | CN | 4-CF₃-phenyl | H |
| 8 | NHCH₂Ph | CN | 2-Cl-phenyl | H |
| 9 | NHCH₂Ph | CN | 4-OCH₃-phenyl | H |
| 10 | SMe | CN | 4-Cl-phenyl | Ph |
| 11 | OEt | CN | 4-Cl-phenyl | Ph |
| 12 | SMe | CN | 4-CF₃-phenyl | Ph |
| 13 | OEt | CN | 4-CF₃-phenyl | Ph |
| 14 | SMe | CN | 4-CH₃-phenyl | Ph |
| 15 | OEt | CN | 4-CH₃-phenyl | Ph |
| 16 | SMe | CN | H | R |
| 17 | CH₂CH₂OH | CN | OPh | Et |
| 18 | CONHEt | CF₃ | pyridin-3-yl | CH₂Ph |
| 19 | SCH₂Ph | NHEt | CONHCH₂Ph | COPh |
| 20 | CH₂NO₂ | CONHEt | NH(4-Cl-phenyl) | H |
| 21 | NHCONH₂ | OMe | CH₂Ph | SO₂Me |
| 22 | Et | CN | thiazol-2-yl | Ph |
| 23 | SMe | CN | piperidin-1-yl | cyclohexyl |
| 24 | OCH₂Ph | Cl | 4-CONHMe-phenyl | cyclohexyl |
| 25 | NHMe | NO₂ | NHPh | H |
| 26 | SMe | NO₂ | NH₂ | H |
| 27 | OEt | NO₂ | NHCH₂Ph | H |
| 28 | NHMe | NH₂ | NHPh | Ph |
| 29 | SMe | NH₂ | NH₂ | Me |
| 30 | OEt | NH₂ | NHCH₂Ph | Me |
| 31 | NHMe | NHCOEt | Ph | Ph |
| 32 | SMe | NHCOEt | CH₂Ph | CH₂Ph |
| 33 | OEt | NHCOEt | CH₂Ph | H |
| 34 | NHMe | CONHMe | Ph | H |
| 35 | SMe | CONHMe | Ph | Ph |
| 36 | OEt | CONRMe | 4-Cl-Ph | Ph |
| 37 | SMe | CN | Ph | 3-OBn-Ph |
| 38 | SMe | CN | Ph | 3-SO₂NH₂-Ph |
| 39 | S-CH₂-phen-4-ol | CN | Ph | Ph |
| 40 | SMe | CN | Ph | 3-OH-Ph |
| 41 | SMe | CN | Ph | 4-OBn-Ph |
| 42 | OH | CN | Ph | 3-OBn-Ph |
| 43 | SMe | CN | cyclohexyl | 3,5-OMe-Ph |
| 44 | SMe | CN | cyclohexyl | 3-SO₂NH₂-Ph |
| 45 | SMe | CN | cyclohexyl | 3-OBn-Ph |
| 46 | SMe | CN | cyclohexyl | Ph |
| 47 | SMe | CN | cyclohexyl | 4-CO₂Et-Ph |
| 48 | SMe | CN | cyclohexyl | 3-OH-Ph |
| 49 | SMe | CN | 3-OMe-Ph | 3-NO₂-Ph |
| 50 | SMe | CN | 3-OMe-Ph | 3-NH₂-Ph |
| 51 | SMe | CN | 3-OH-Ph | 3-NO₂-Ph |
| 52 | SMe | CN | 3-OBn-Ph | Ph |
| 53 | SMe | CN | 3-OBn-Ph | 3-NO₂-Ph |
| 54 | N(Me)₂ | CN | 3-OBn-Ph | Ph |
| 55 | N(Me)₂ | CN | 3-OBn-Ph | 3-NO₂-Ph |
| 56 | SMe | CN | 3-pyridyl | 3-OBn-Ph |
| 57 | SMe | CN | 3-pyridyl | 3-OH-Ph |
| 58 | OEt | CN | Ph | Ph |
| 59 | SMe | CN | 3-Br-Ph | 3-NH₂-Ph |
| 60 | N(Me)₂ | CN | 3-OPh-Ph | 3-NH₂-Ph |
| 61 | SMe | CN | 3-OPh-Ph | 3-NH₂-Ph |
| 62 | SMe | CN | 5-Br-3-pyridyl | 3-OBn-Ph |
| 63 | 4-Me-piperidin-1-yl | CN | 3-OPh-Ph | Ph |
| 64 | OH | CN | 4-tolyl | Ph |
| 65 | SMe | CN | 3-OBn-Ph | 3-OH-Ph |
| 66 | SMe | CN | 3-OPh-Ph | 3-OH-Ph |
| 67 | SMe | CN | 3-OH-Ph | 3-OH-Ph |
| 68 | SMe | CN | 3-Br-Ph | 3-OH-Ph |
| 69 | SMe | CN | 3-Br-Ph | 3-OBn-Ph |
| 70 | NHEt | CN | Ph | 3-OH-Ph |
| 71 | SMe | CN | 3-(3-OH-Ph)-Ph | 3-OH-Ph |
| 72 | SMe | CN | 3-(3-OEt-Ph)-Ph | 3-OH-Ph |

TABLE 1-continued

Compounds of Formula IIa

| No. IIa- | R¹ | R² | R³ | R⁴ |
|---|---|---|---|---|
| 73 | SMe | CN | 3-(3-pyridyl)-Ph | 3-OH-Ph |
| 74 | SMe | CN | 5-Ph-pyridin-3-yl | 3-OBn-Ph |
| 75 | N(Me)₂ | CN | 5-Br-3-pyridyl | 3-OBn-Ph |
| 76 | N(Me)₂ | CN | 5-Ph-3-pyridyl | 3-OBn-Ph |
| 77 | SMe | CO₂Et | Ph | 3-OR-Ph |
| 78 | SMe | CO₂Et | Ph | Ph |
| 79 | NHEt | CN | Ph | 4-OH-Ph |
| 80 | N(Me)₂ | CN | 5-Ph-pyridin-3-yl | 3-OH-Ph |
| 81 | SMe | CN | 3-(3-NH₂-Ph)-Ph | 3-OH-Ph |
| 82 | SMe | CN | 3-(3-Cl,4-F-Ph)-Ph | 3-OH-Ph |
| 83 | SMe | CN | 3-(4-iPr-Ph)-Ph | 3-OH-Ph |
| 84 | SMe | CN | 5-Ph-pyridin-3-yl | 3-OH-Ph |
| 85 | SMe | CN | 5-Ph-pyridin-3-yl | 3-NO₂-Ph |
| 86 | SMe | CN | 3-(3-N-Boc-pyrrol-2-yl)-Ph | 3-OH-Ph |
| 87 | SMe | CN | 3-(4-iPr-Ph)-Ph | 3-OH-Ph |
| 88 | SMe | CN | 3-pyridyl | 3-NHSO₂Me-Ph |
| 89 | SMe | CN | 3-pyridyl | 3-NHSO₂Et-Ph |
| 90 | NHEt | CO₂Et | Ph | 3-OMe-Ph |
| 91 | SMe | CN | 3-pyridyl | 3-SO₂NH₂-Ph |
| 92 | SMe | CN | 3-(2-OH-Ph)-Ph | 3-OH-Ph |
| 93 | SMe | CN | 3-(3-pyrrol-2-yl)-Ph | 3-OH-Ph |
| 94 | SMe | CN | 3-(6-OMe-pyridin-2-yl)-Ph | 3-OH-Ph |
| 95 | SMe | CN | 3-(5-OMe-pyridin-2-yl)-Ph | 3-OH-Ph |
| 96 | SMe | CN | 3-(2,5-Me₂-isoxazol-4-yl)-Ph | 3-OH-Ph |
| 97 | NH(CH₃)₂ morpholin-4-yl | CN | Ph | 3-OH-Ph |
| 98 | NH(CH₃)₂ morpholin-4-yl | CN | Ph | 3-SO₂NH₂-Ph |
| 99 | NH(CH₃)₂ morpholin-4-yl | CN | Ph | 4-OH-Ph |
| 100 | NH(CH₃)₃ N(Et)₂ | CN | Ph | 3-OH-Ph |
| 101 | NH(CH₃)₃ N(Et)₂ | CN | Ph | 4-OH-Ph |
| 102 | NH(CH₃)₂ piperidin-1-yl | CN | Ph | 3-OH-Ph |
| 103 | NH(CH₃)₂ piperidin-1-yl | CN | Ph | 3-SO₂NH₂-Ph |
| 104 | NH(CH₃)₂ piperidin-1-yl | CN | Ph | 4-OH-Ph |
| 105 | SMe | CN | 3-(pyridin-4-yl)-Ph | 3-OH-Ph |

Exemplary structures of formula IIb are set forth in Table 2 below.

TABLE 2

Compounds of Formula IIb

| No. IIb- | R¹ | R² | R³ | R⁴ |
|---|---|---|---|---|
| 1 | SMe | 4-CH₃-thiazol-2-yl | Me | Ph |
| 2 | SMe | 4-CH₃-thiazol-2-yl | Me | 4-F-Ph |
| 3 | SMe | 4-CH₃-thiazol-2-yl | Me | 6-Cl-pyridin-3-yl |
| 4 | SMe | 4-CH₃-thiazol-2-yl | Me | 3-Cl-Ph |
| 5 | SMe | 4-CH₃-thiazol-2-yl | Me | 3-CH₃O-Ph |
| 6 | SMe | 4-CH₃-thiazol-2-yl | Me | 3-BnO-Ph |
| 7 | SMe | CN | Me | Ph |
| 8 | SMe | CN | Me | 4-F-Ph |
| 9 | SMe | CN | Me | 6-Cl-pyridin-3-yl |

TABLE 2-continued

Compounds of Formula IIb

| No. IIb- | R¹ | R² | R³ | R⁴ |
|---|---|---|---|---|
| 10 | SMe | CN | Me | 3-Cl-Ph |
| 11 | SMe | CN | Me | 3-CH₃O-Ph |
| 12 | SMe | CN | Me | 3-BnO-Ph |

The above formulae IIa and IIb compounds are those having a pyrimidine ring. Compounds of formula I having a pyridine or triazine ring are otherwise structurally similar to the formulae IIa and IIb compounds and are represented by the following general formulae IIIa, IIIb, IVa, and IVb shown below in Table 3.

TABLE 3

Formulae IIIa, IIIb, IVa, and IVb

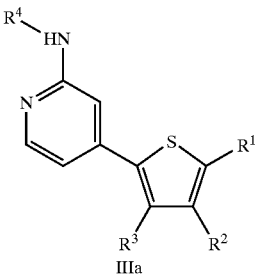

IIIa

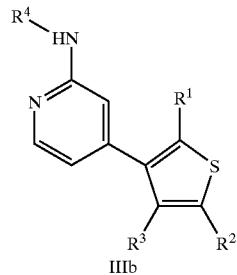

IIIb

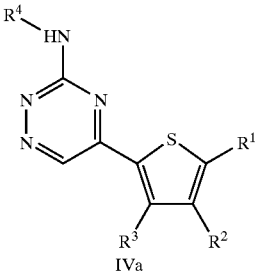

IVa

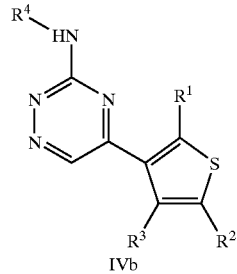

IVb

The compounds shown above in Table 3 are structurally similar to compounds of formula IIa and IIb where the pyrimidine ring of formula IIa is replaced by a pyridine (IIIa and IIIb) or triazine ring (IVa and IVb). Accordingly, preferred $R^1$, $R^2$, $R^3$, and $R^4$ groups of the compounds shown above in Table 3 are as described above for the formula IIa compounds.

Exemplary structures of formulae IIIa and IIIb are set forth in Table 4 below.

TABLE 4

Compounds of Formulae IIIa and IIIb

| No. | $R^1$ | $R^2$ | $R^3$ | $R^4$ |
|---|---|---|---|---|
| IIIa-1 | SMe | CN | 4-CO$_2$H-phenyl | H |
| IIIa-2 | SMe | CN | 4-Cl-phenyl | H |
| IIIa-3 | SMe | CN | 4-CF$_3$-phenyl | H |
| IIIa-4 | SMe | CN | 4-CH$_3$-phenyl | H |
| IIIa-5 | SMe | CN | 2-Cl-phenyl | H |
| IIIa-6 | SMe | CN | 4-OCH$_3$-phenyl | H |
| IIIa-7 | NHCH$_2$Ph | CN | 4-CF$_3$-phenyl | H |
| IIIa-8 | NHCH$_2$Ph | CN | 2-Cl-phenyl | H |
| IIIa-9 | NHCH$_2$Ph | CN | 4-OCH$_3$-phenyl | H |
| IIIa-10 | SMe | CN | 4-Cl-phenyl | Ph |
| IIIa-11 | OEt | CN | 4-Cl-phenyl | Ph |
| IIIa-12 | SMe | CN | 4-CF$_3$-phenyl | Ph |
| IIIa-13 | OEt | CN | 4-CF$_3$-phenyl | Ph |
| IIIa-14 | SMe | CN | 4-CH$_3$-phenyl | Ph |
| IIIa-15 | OEt | CN | 4-CH$_3$-phenyl | Ph |
| IIIa-16 | CH$_2$CH$_2$OH | CN | OPh | Et |
| IIIa-17 | CONHEt | CF$_3$ | pyridin-3-yl | CH$_2$Ph |
| IIIa-18 | SCH$_2$Ph | NHEt | CONHCH$_2$Ph | COPh |
| IIIa-19 | CH$_2$NO$_2$ | CONHEt | NH(4-Cl-phenyl) | H |
| IIIa-20 | NHCONH$_2$ | OMe | CH$_2$Ph | SO$_2$Me |
| IIIa-21 | Et | CN | thiazol-2-yl | Ph |
| IIIa-22 | SMe | CN | piperidin-1-yl | cyclohexyl |
| IIIa-23 | OCH$_2$Ph | Cl | 4-CONHMe-phenyl | cyclohexyl |
| IIIb-1 | SMe | CN | CH$_3$ | Ph |
| IIIb-2 | SMe | CN | CH$_3$ | 4-F-Ph |
| IIIb-3 | SMe | CN | CH$_3$ | 3-CH$_3$O-Ph |
| IIIb-4 | OEt | CN | 4-CH$_3$-phenyl | Ph |
| IIIb-5 | CH$_2$CH$_2$OH | CN | OPh | Et |
| IIIb-6 | CONHEt | CF$_3$ | pyridin-3-yl | CH$_2$Ph |
| IIIb-7 | SCH$_2$Ph | NHEt | CONHCH$_2$Ph | COPh |
| IIIb-8 | CH$_2$NO$_2$ | CONHEt | NH(4-Cl-phenyl) | H |
| IIIb-9 | NHCONH$_2$ | OMe | CH$_2$Ph | SO$_2$Me |

Exemplary structures of formulae IVa and IVb are set forth in Table 5 below.

TABLE 5

Compounds of Formula IVa and IVb

| No.IV- | $R^1$ | $R^2$ | $R^3$ | $R^4$ |
|---|---|---|---|---|
| IVa-1 | SMe | CN | 4-CO$_2$H-phenyl | H |
| IVa-2 | SMe | CN | 4-Cl-phenyl | H |
| IVa-3 | SMe | CN | 4-CF$_3$-phenyl | H |
| IVa-4 | SMe | CN | 4-CH$_3$-phenyl | H |
| IVa-5 | SMe | CN | 2-Cl-phenyl | H |
| IVa-6 | SMe | CN | 4-OCH$_3$-phenyl | H |
| IVa-7 | NHCH$_2$Ph | CN | 4-CF$_3$-phenyl | H |
| IVa-8 | NHCH$_2$Ph | CN | 2-Cl-phenyl | H |
| IVa-9 | NHCH$_2$Ph | CN | 4-OCH$_3$-phenyl | H |
| IVa-10 | SMe | CN | 4-Cl-phenyl | Ph |
| IVa-11 | OEt | CN | 4-Cl-phenyl | Ph |
| IVa-12 | SMe | CN | 4-CF$_3$-phenyl | Ph |
| IVa-13 | OEt | CN | 4-CF$_3$-phenyl | Ph |
| IVa-14 | SMe | CN | 4-CH$_3$-phenyl | Ph |
| IVa-15 | OEt | CN | 4-CH$_3$-phenyl | Ph |
| IVa-16 | CH$_2$CH$_2$OH | CN | OPh | Et |
| IVa-17 | CONHEt | CF$_3$ | pyridin-3-yl | CH$_2$Ph |
| IVa-18 | SCH$_2$Ph | NHEt | CONHCH$_2$Ph | COPh |
| IVa-19 | CH$_2$NO$_2$ | CONHEt | NH(4-Cl-phenyl) | H |
| IVa-20 | NHCONH$_2$ | OMe | CH$_2$Ph | SO$_2$Me |
| IVa-21 | Et | CN | thiazol-2-yl | Ph |
| IVa-22 | SMe | CN | piperidin-1-yl | cyclohexyl |
| IVa-23 | OCH$_2$Ph | Cl | 4-CONHMe-phenyl | cyclohexyl |
| IVb-1 | SMe | CN | CH$_3$ | pyridin-3-yl |
| IVb-2 | SMe | CN | CH$_3$ | Ph |
| IVb-3 | SMe | CN | CH$_2$CH$_3$ | H |
| IVb-4 | CH$_2$CH$_2$OH | CN | OPh | Et |
| IVb-5 | CONHEt | CF$_3$ | pyridin-3-yl | CH$_2$Ph |
| IVb-6 | SCH$_2$Ph | NHEt | CONHCH$_2$Ph | COPh |
| IVb-7 | CH$_2$NO$_2$ | CONHEt | NH(4-Cl-phenyl) | H |
| IVb-8 | NHCONH$_2$ | OMe | CH$_2$Ph | SO$_2$Me |
| IVb-9 | Et | CN | thiazol-2-yl | Ph |
| IVb-10 | SMe | CN | piperidin-1-yl | cyclohexyl |
| IVb-11 | OCH$_2$Ph | Cl | 4-CONHMe-phenyl | cyclohexyl |

A preferred embodiment of this invention relates to compounds of formula V:

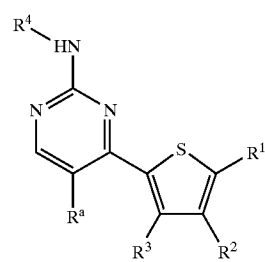

V or a pharmaceutically acceptable derivative thereof, wherein $R^a$, $R^1$, $R^2$, $R^3$, and $R^4$ are as defined above.

Preferred compounds of formula V include those having one or more, and most preferably all, of the following features:

(a) $R^1$ is selected from N(R)$_2$, OR, SR, or (T)$_n$—R$^5$;

(b) T is a C$_{1-4}$ alkylidene chain, wherein one methylene unit of T is optionally replaced by S, O, N(R), or CO$_2$;

(c) $R^2$ is CN, R, halogen, C$_2$R$^5$, or N(R)$_2$;

(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one (T)$_n$—Ar group and one $R^7$;

(e) $R^4$ is hydrogen or Ar, wherein Ar is an optionally substituted 6 membered saturated, partially saturated, or aryl ring having zero to two heteroatoms independently selected from nitrogen, oxygen, or sulfur; and (f) $R^a$ is selected from R$^b$, OR$^b$, SR$^b$, or N(R$^b$)$_2$.

More preferred compounds of formula V are those having one or more, more preferably more than one, and most preferably all, of the features selected from the group consisting of:

(a) $R^1$ is selected from SCH$_2$-4-phenol, SCH$_3$, OH, OEt, N(Me)$_2$, OMe, 4-methylpiperidin-1-yl, NHEt, NHCH$_2$CH$_2$piperidin-1-yl, or NHCH$_2$CH$_2$morpholin-4-yl;

(b) $R^2$ is CN or C$_2$R$^5$;

(c) $R^3$ is selected from phenyl, pyridyl, pyrimidinyl, cyclohexyl, or furanyl, wherein $R^3$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropyl-phenyl, 4-F-3-Cl-phenyl, pyrrolyl, pyrimidinyl, chloro, bromo, fluoro, trifluoromethyl, OH, $NH_2$, methyl, methoxy or ethoxy;

(d) $R^4$ is selected from hydrogen or a phenyl, benzyl, pyridyl, piperidinyl, or cyclohexyl ring, wherein said ring is optionally subsituted with benzyloxy, phenoxy, $SO_2NH_2$, OH, $NO_2$, $NH_2$, OMe, Br, Cl, $CO_2Me$, $NHSO_2Me$, $NHSO_2Et$, $NHCON(Me)_2$, $NHCON(Et)_2$, NHCOpyrrolidin-1-yl, or NHCOmorpholin-4-yl; and (e) $R^a$ is methyl, OH, OMe, or $NH_2$.

Exemplary structures of formula V, wherein $R^2$ is CN, are set forth in Table 7 below.

TABLE 7

Compounds of Formula V

| No.V- | $R^1$ | $R^a$ | $R^3$ | $R^4$ |
|---|---|---|---|---|
| 1 | $SCH_2$phen-4-ol | Me | 3-Cl phenyl | Ph |
| 2 | OH | Me | Ph | 3-OBn-Ph |
| 3 | OEt | Me | Ph | 3-OBn-Ph |
| 4 | SMe | Me | Ph | 3-OBn-Ph |
| 5 | SMe | Me | Ph | 3-$SO_2NH_2$-Ph |
| 6 | SMe | Me | Ph | 3-OH-Ph |
| 7 | SMe | Me | Ph | 3-$NO_2$-Ph |
| 8 | SMe | Me | Ph | 3-$NH_2$-Ph |
| 9 | SMe | Me | 2-$CF_3$-Ph | 3-OBn-Ph |
| 10 | SMe | Me | 2-$CF_3$-Ph | 3-OH-Ph |
| 11 | $SCH_2$phen-4-ol | Me | 3-Cl-Ph | Ph |
| 12 | SMe | Me | 4-Me-Ph | 3-OBn-Ph |
| 13 | SMe | Me | 4-Me-Ph | 3-OH-Ph |
| 14 | SMe | Me | 4-Me-Ph | pyrid-3-yl |
| 15 | SMe | Me | pyrid-3-yl | 3-OBn-Ph |
| 16 | SMe | Me | pyrid-3-yl | Ph |
| 17 | SMe | Me | pyrid-3-yl | 3-OMe-Ph |
| 18 | SMe | Me | pyrid-3-yl | 3,5-OMe-Ph |
| 19 | SMe | Me | pyrid-3-yl | 3-Br-Ph |
| 20 | SMe | Me | pyrid-3-yl | 3-Cl-Ph |
| 21 | SMe | Me | pyrid-3-yl | 3-$CO_2$Me-Ph |
| 22 | SMe | Me | pyrid-3-yl | 6-Cl-pyrid-3-yl |
| 23 | SMe | Me | pyrid-3-yl | $CH_2$Ph |
| 24 | SMe | Me | pyrid-3-yl | 3-OH-Ph |
| 25 | SMe | Me | furan-2-yl | pyrid-3-yl |
| 26 | SMe | Me | furan-2-yl | 3-OH-Ph |
| 27 | SMe | Me | furan-2-yl | 3-OBn-Ph |
| 28 | SMe | Me | furan-2-yl | 3-$NO_2$-Ph |
| 29 | $N(Me)_2$ | Me | 3-OPh-Ph | 3-$NO_2$-Ph |
| 30 | $N(Me)_2$ | Me | 3-OPh-Ph | 3-OH-Ph |
| 31 | SMe | Me | 3-Ph-Ph | 3-OBn-Ph |
| 32 | SMe | Me | 3-Ph-Ph | 3-OH-Ph |

A more preferred embodiment relates to compounds of formula VI:

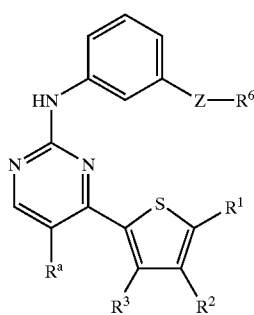

VI or a pharmaceutically acceptable derivative thereof, wherein $R^1$, $R^2$, $R^3$, $R^a$, Z, and $R^6$ are as defined above.

Preferred $R^1$, $R^2$, $R^3$, and $R^a$ groups of formula VI are those described above for formula IIa.

Preferred Z—$R^6$ groups of formula VI are those wherein Z is a $C_{1-4}$ alkylidene chain wherein one methylene unit of Z is optionally replaced by O, NH, NHCO, $NHCO_2$, $NHSO_2$, CONH, and wherein $R^6$ is selected from $N(R)_2$, NHCOR, or Ar wherein Ar is a 5–6 membered heterocyclic or heteroaryl ring having one to two heteroatoms independently selected from nitrogen, oxygen, or sulfur. The Ar group of $R^6$ is optionally substituted with R, OR, $N(R)_2$, or oxo. More preferred Z—$R^6$ groups of formula VI are selected from $O(CH_2)_3OH$, $O(CH_2)_3NH(CH_2)_2OH$, $O(CH_2)_2NH(CH_2)_2OH$, $O(CH_2)_3N$(hydroxyethyl)(methyl), $O(CH_2)_3$pyrrolidin-1-yl, $O(CH_2)_2$morpholin-4-yl, $O(CH_2)_3N(Me)_2$, $O(CH_2)_3N(Et)_2$, $O(CH_2)_3$(4-hydroxyethylpiperazin-1-yl), $O(CH_2)_3$piperazin-1-yl, $O(CH_2)_3$(4-hydroxymethylpiperidin-1-yl), $O(CH_2)_3$(4-hydroxypiperidin-1-yl), $NHCO(CH_2)_3N(Me)_2$, $NHCO(CH_2)_3NCOCH_3$, $NHCOCH_2$pyridin-2-yl, $NHCOCH_2$(2-aminothiazol-4-yl), $NHCOCH_2$cyclopropyl, $NHCO(CH_2)_2N(Et)_2$, NHCO$(CH_2)_2$(piperazin-2,5-dione-3-yl), NHCOpyrrolidin-1-yl, NHCOmorpholin-4-yl, $NHCO_2CH_2$tetrahydrofuran-2-yl, $NHCO_2$tetrahydrofuran-2-yl, $NHCO_2$tetrahydropyran-4-yl, or $NHCO_2CH_2$tetrahydropyran-2-yl.

Preferred compounds of formula VI are those having one or more, more preferably more than one, and most preferably all, of the features selected from the group consisting of:

(a) $R^1$ is $N(R)_2$, OR, SR, or $(T)_n$—$R^5$;

(b) T is a $C_{1-4}$ alkylidene chain, wherein one methylene unit of T is optionally replaced by S, O, N(R), or $CO_2$;

(c) $R^2$ is CN, $R^7$, halogen, or $N(R^6)_2$;

(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one $(T)_n$—Ar group and one $R^7$;

(e) Z is a $C_{1-4}$ alkylidene chain wherein one methylene unit of Z is optionally replaced by O, NH, NHCO, $NHCO_2$, $NHSO_2$, CONH;

(f) $R^6$ is selected from $N(R)_2$, NHCOR, or Ar wherein Ar is an optionally substituted 5–6 membered heterocyclic or heteroaryl ring having one to two heteroatoms independently selected from nitrogen, oxygen, or sulfur; and (g) $R^a$ is $R^b$, $OR^b$, $SR^b$, or $N(R^b)_2$.

More preferred compounds of formula VI are those having one or more, more preferably more than one, and most preferably all, of the features selected from the group consisting of:

(a) $R^1$ is selected from $SCH_2$-4-phenol, $SCH_3$, OH, OEt, $N(Me)_2$, OMe, 4-methylpiperidin-1-yl, NHEt, $NHCH_2CH_2$piperidin-1-yl, or $NHCH_2CH_2$morpholin-4-yl;

(b) $R^2$ is CN;

(c) $R^3$ is a phenyl, pyridyl, furyl, or cyclohexyl ring optionally substituted with $(T)_n$—Ar or $R^7$ wherein Ar is a 5–6 membered aryl ring having zero to two heteroatoms independently selected from nitrogen, oxygen, or sulfur, and wherein $R^7$ is selected from R, halogen, OR, $N(R)_2$, or $CO_2R$;

(d) $R^a$ is hydrogen or methyl; and (e) Z—$R^6$ is selected from $O(CH_2)_3OH$, $O(CH_2)_3NH(CH_2)_2OH$, $O(CH_2)_2NH(CH_2)_2OH$, $O(CH_2)_3N$(hydroxyethyl)(methyl), $O(CH_2)_3$pyrrolidin-1-yl, O(CH$_2$)$_2$morpholin-4-yl, O(CH$_2$)$_3$N(Me)$_2$, O(CH$_2$)$_3$N(Et)$_2$, O(CH$_2$)$_3$(4-hydroxyethylpiperazin-1-yl), O(CH$_2$)$_3$piperazin-1-yl, O(CH$_2$)$_3$(4-hydroxymethylpiperidin-1-yl), O(CH$_2$)$_3$(4-hydroxypiperidin-1-yl), NHCO (CH$_2$)$_3$N(Me)$_2$, NHCO(CH$_2$)$_3$NCOCH$_3$, NHCOCH$_2$pyridin-2-yl, NHCOCH$_2$(2-aminothiazol-4-yl), NHCOCH$_2$cyclopropyl, NHCO(CH$_2$)$_2$N (Et)$_2$, NHCOCH$_2$)$_2$(piperazin-2,5-dione-3-yl), NHCOpyrrolidin-1-yl, NHCOmorpholin-4-yl, NHCO$_2$CH$_2$tetrahydrofuran-2-yl, NHCO$_2$tetrahydrofuran-2-yl, NHCO$_2$tetrahydropyran-4-yl, or NHCO$_2$CH$_2$tetrahydropyran-2-yl.

Exemplary structures of formula VI are set forth in Table 8 below.

TABLE 8

Compounds of Formula VI

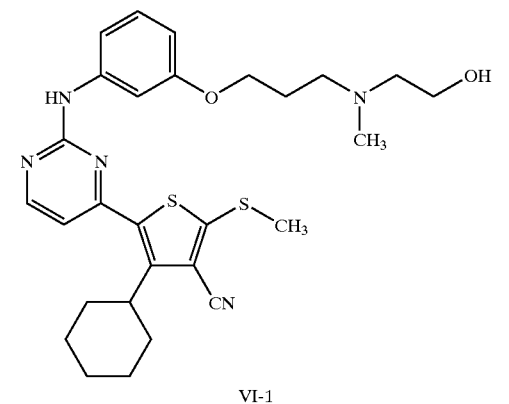

VI-1

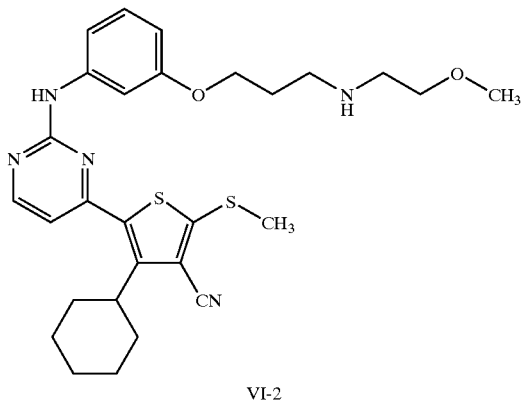

VI-2

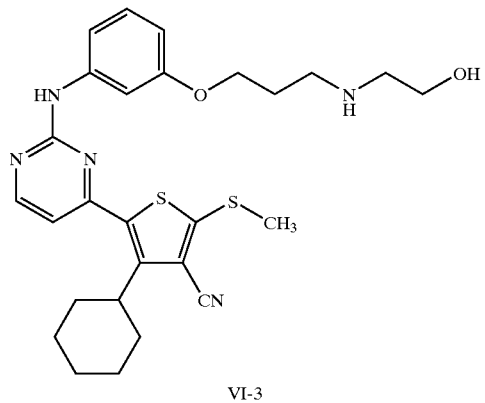

VI-3

TABLE 8-continued

Compounds of Formula VI

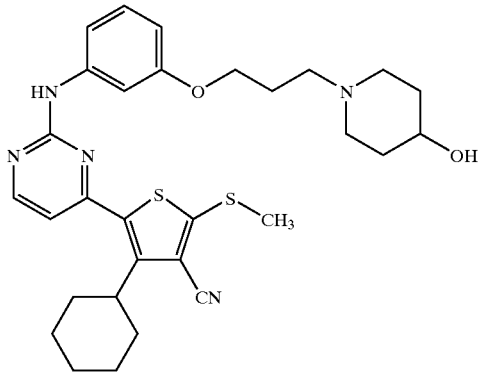

VI-4

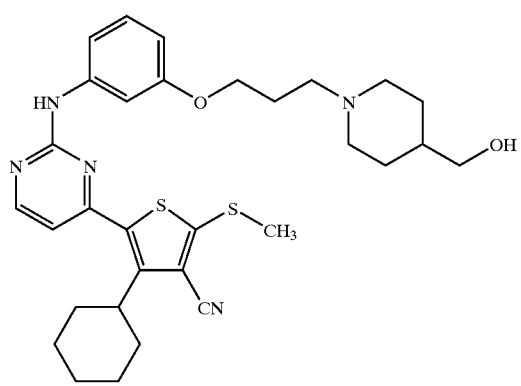

VI-5

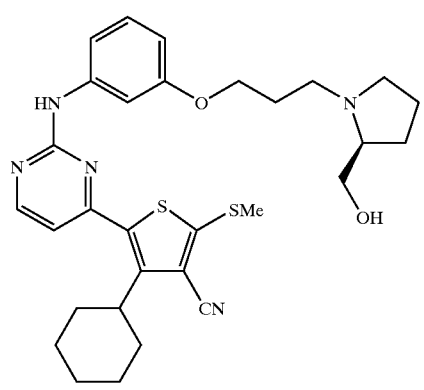

VI-6

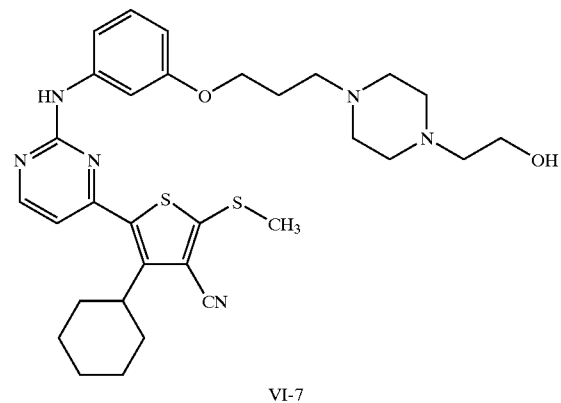

VI-7

TABLE 8-continued
Compounds of Formula VI
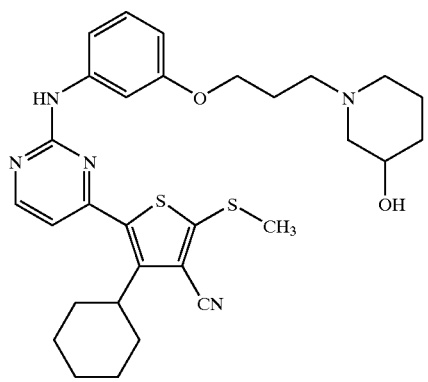
VI-8
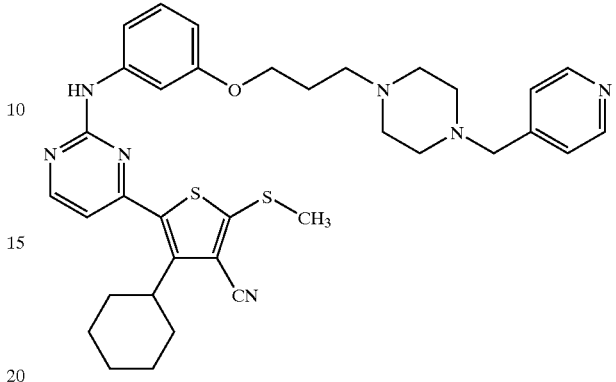
VI-11
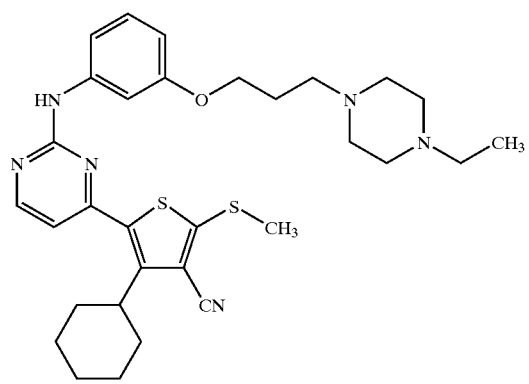
VI-9
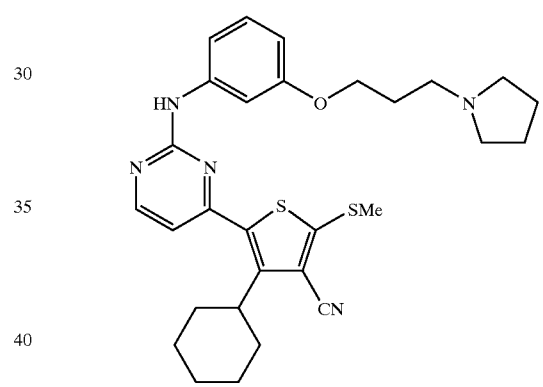
VI-12
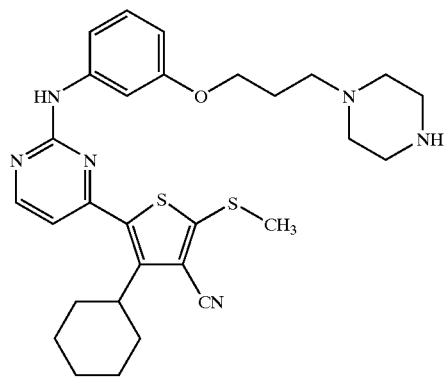
VI-10
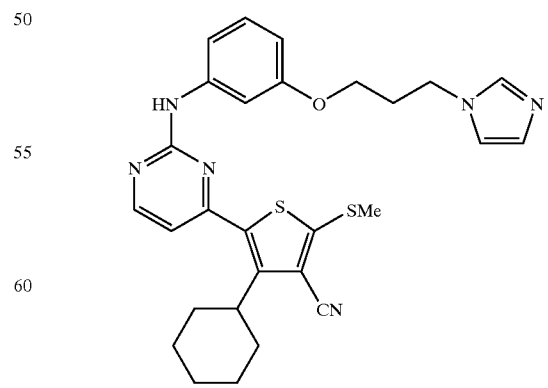
VI-13

TABLE 8-continued
Compounds of Formula VI
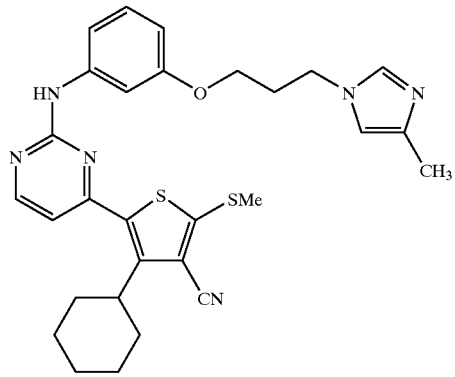
VI-14
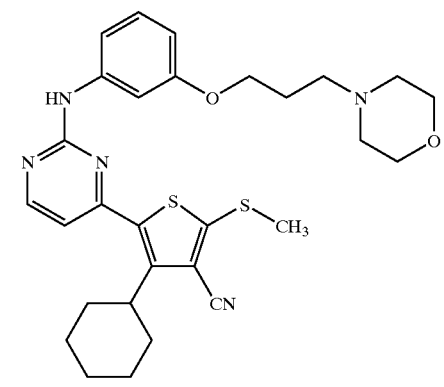
VI-15
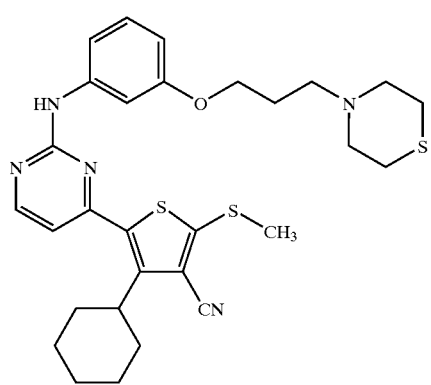
VI-16
TABLE 8-continued
Compounds of Formula VI
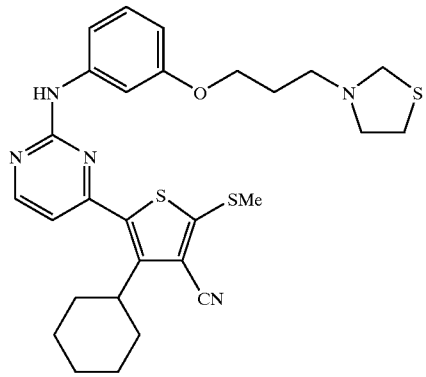
VI-17
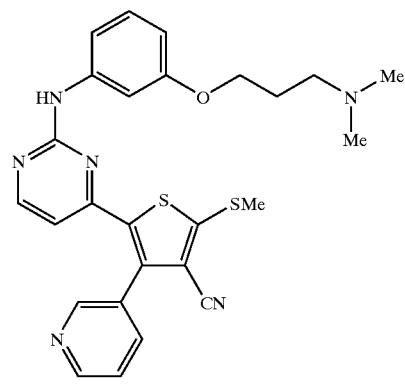
VI-18
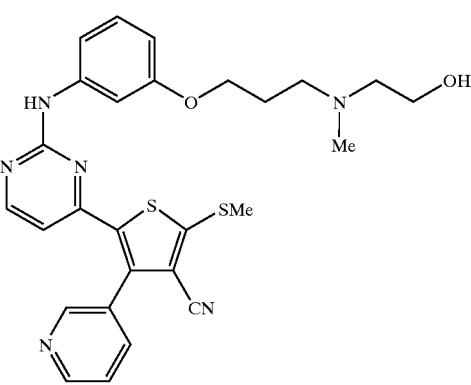
VI-19

TABLE 8-continued
Compounds of Formula VI
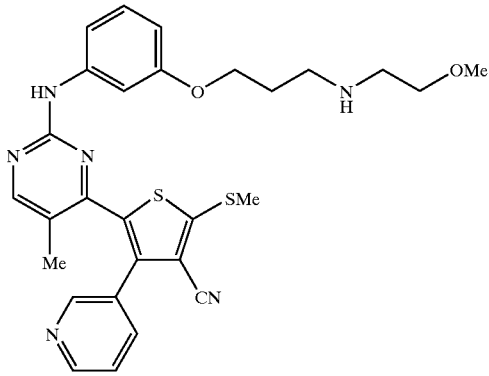
VI-20
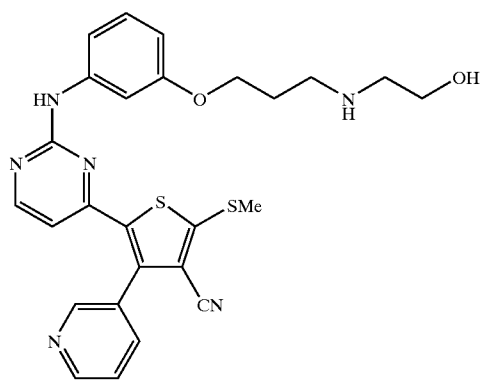
VI-21
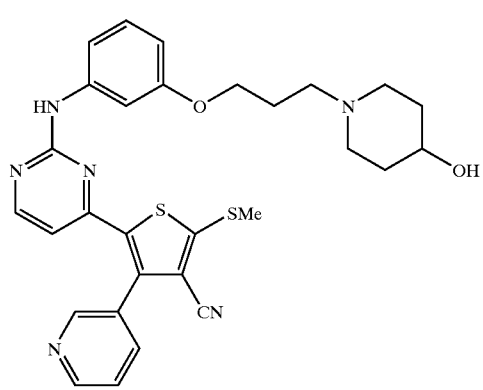
VI-22
TABLE 8-continued
Compounds of Formula VI
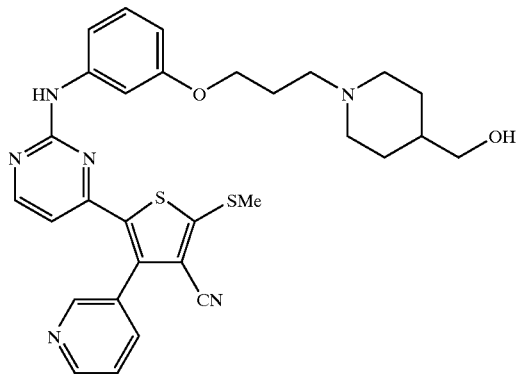
VI-23
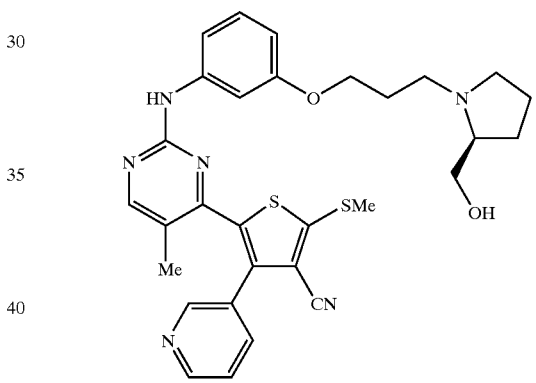
VI-24
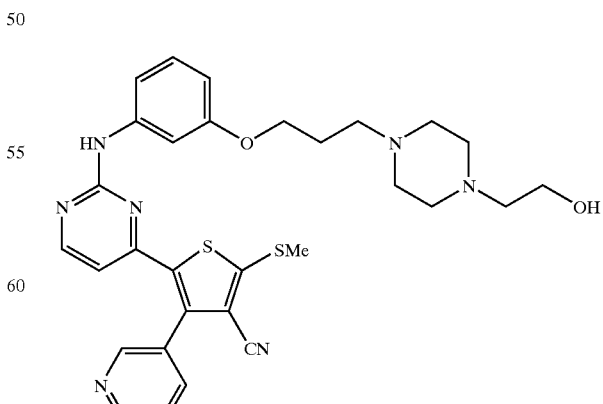
VI-25

TABLE 8-continued
Compounds of Formula VI
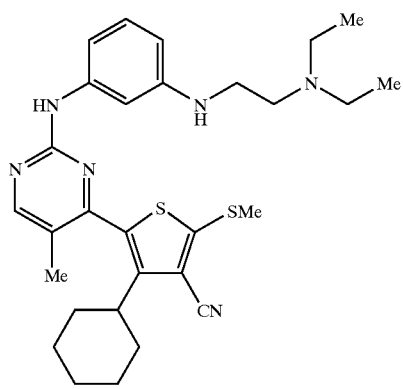
VI-26
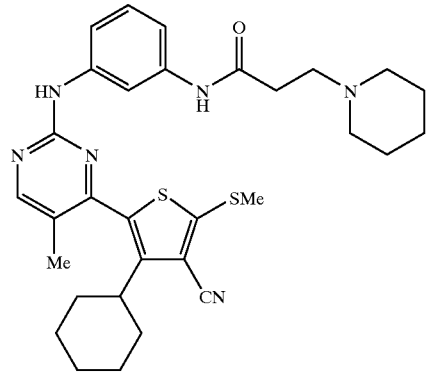
VI-27
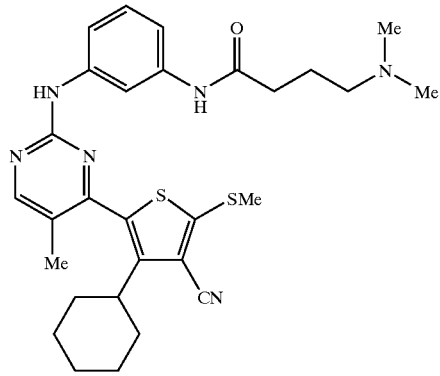
VI-28
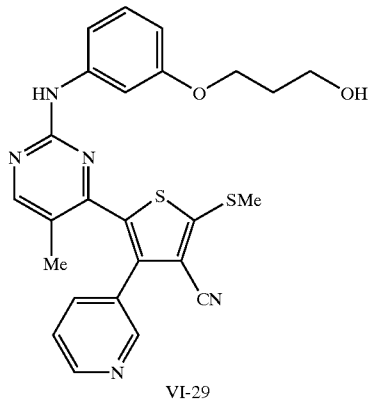
VI-29
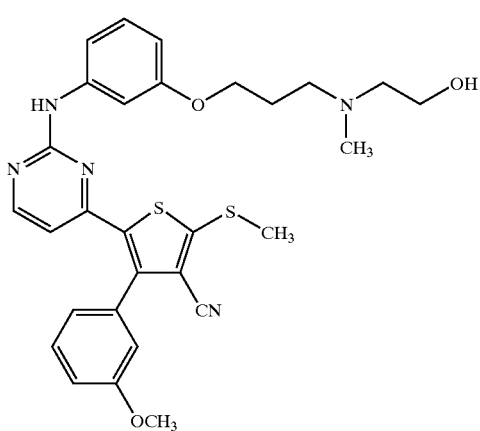
VI-30
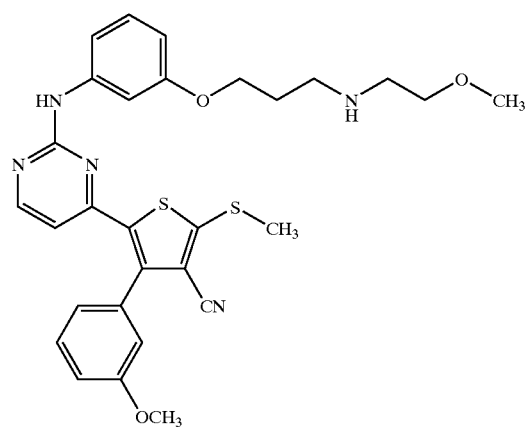
VI-31

TABLE 8-continued
Compounds of Formula VI
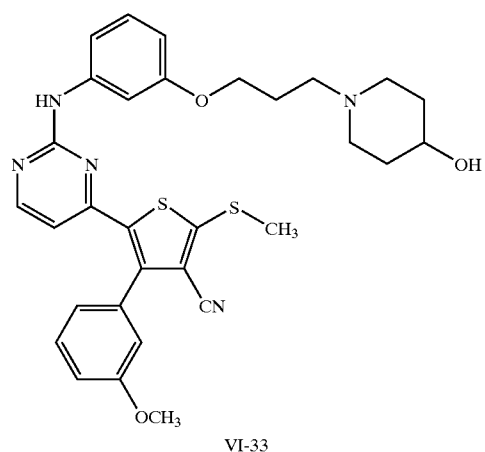
VI-32
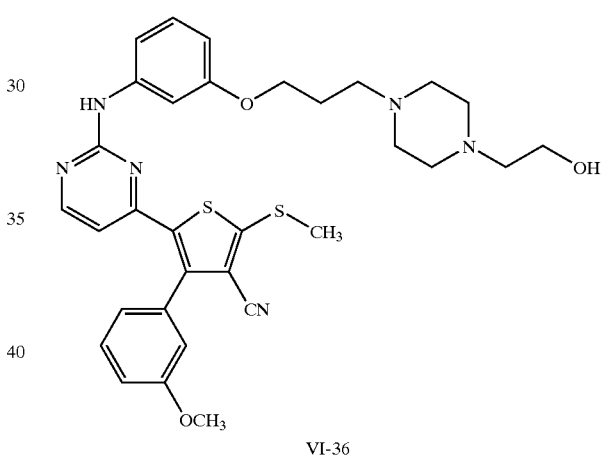
VI-35
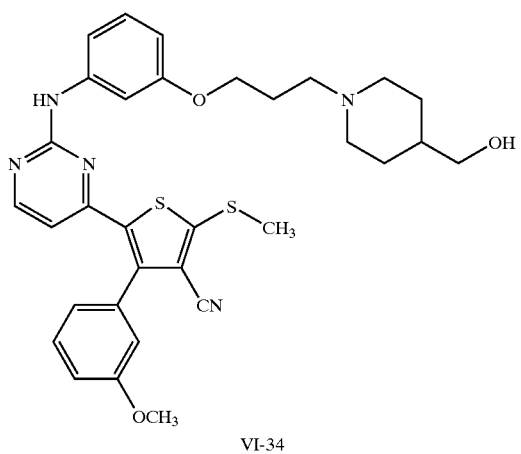
VI-33
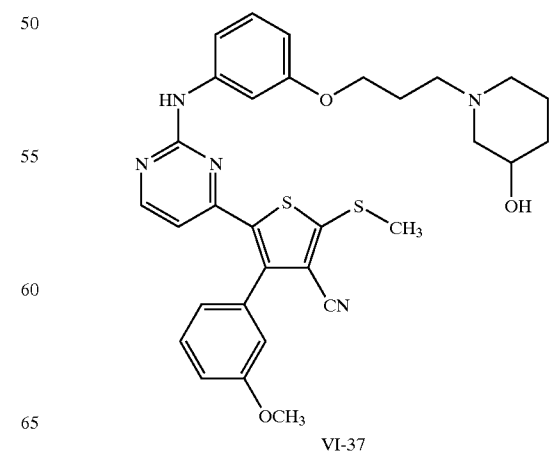
VI-36
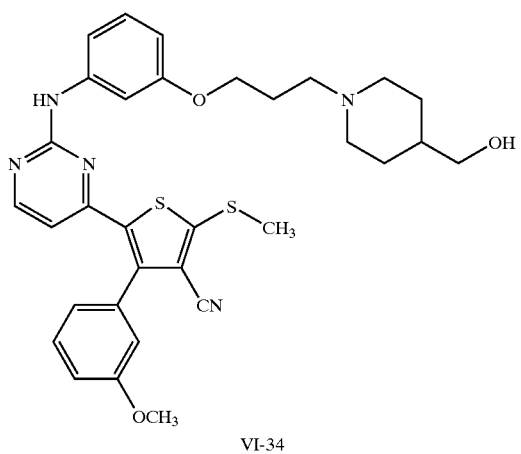
VI-34
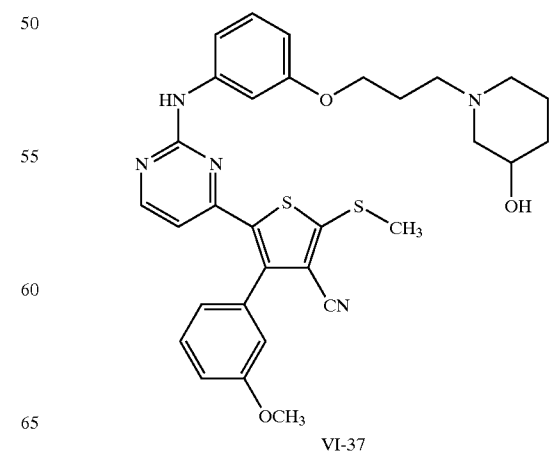
VI-37

TABLE 8-continued

Compounds of Formula VI

VI-38

VI-39

VI-40

VI-41

VI-42

VI-43

TABLE 8-continued
Compounds of Formula VI
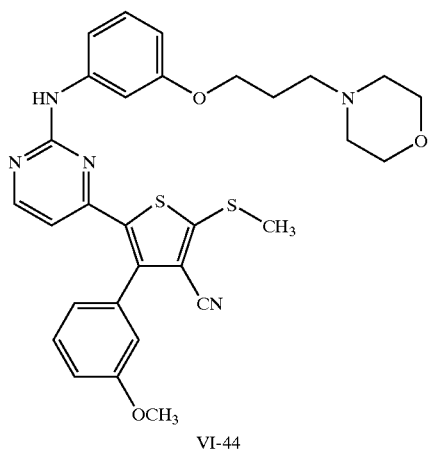
VI-44
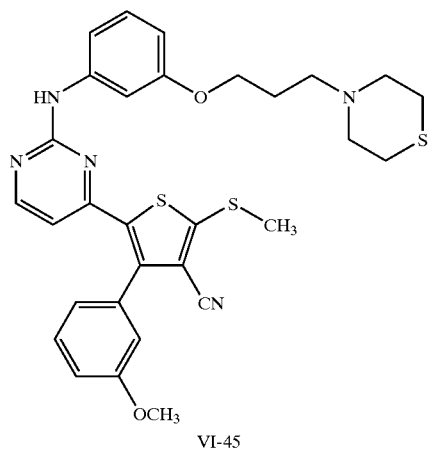
VI-45
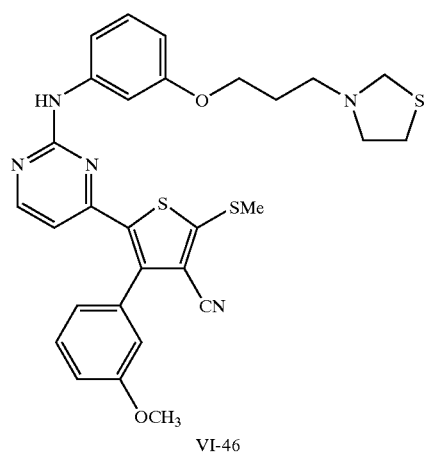
VI-46
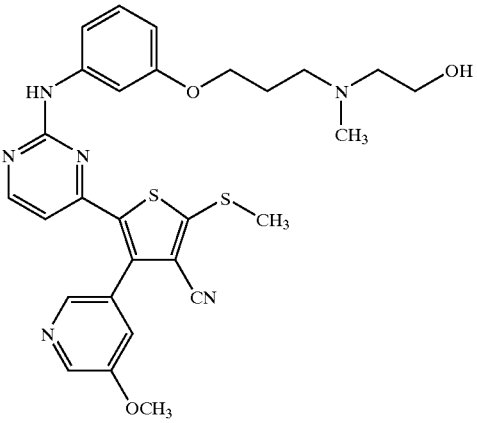
VI-47
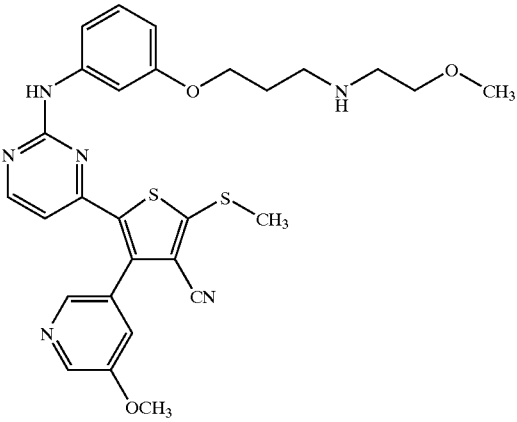
VI-48
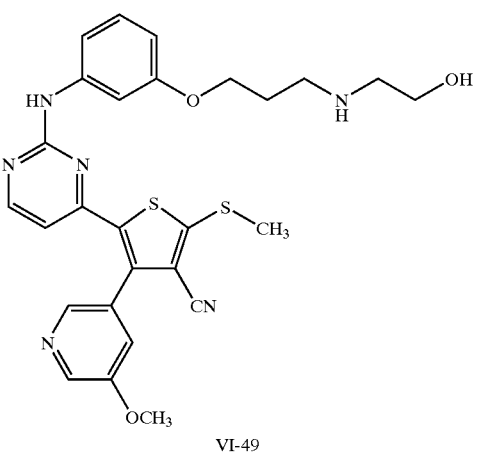
VI-49

TABLE 8-continued
Compounds of Formula VI
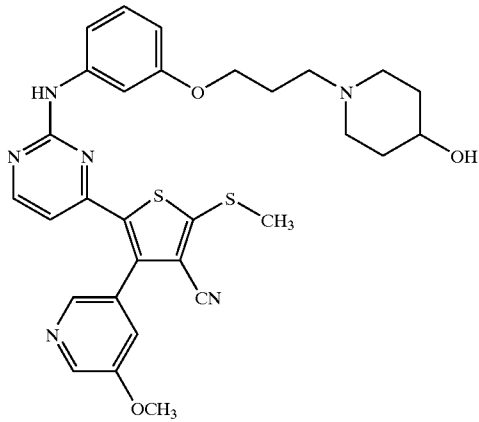
VI-50
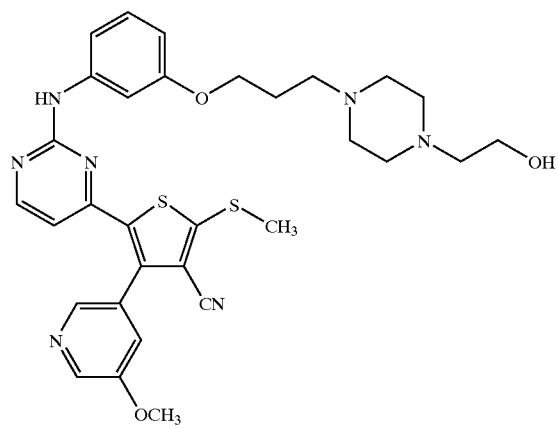
VI-53
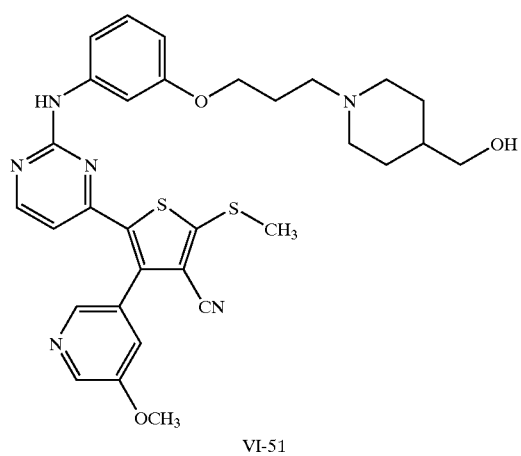
VI-51
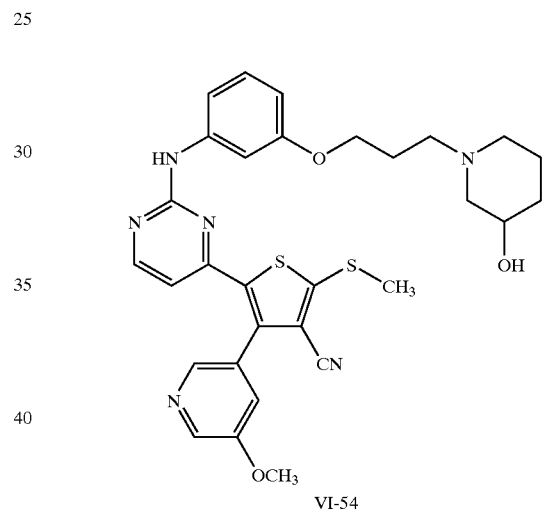
VI-54
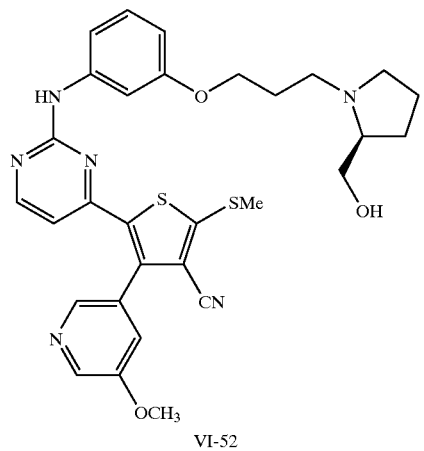
VI-52
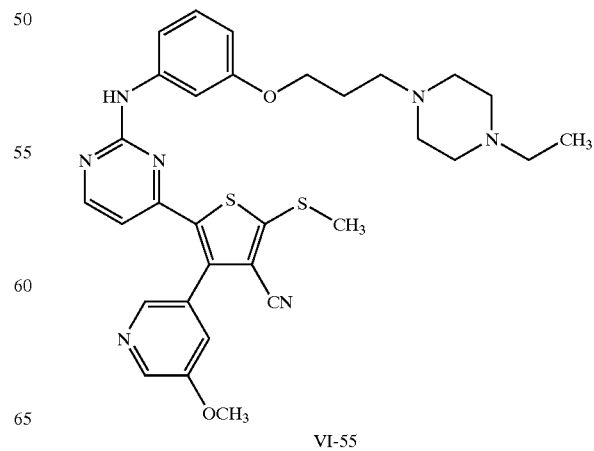
VI-55

TABLE 8-continued
Compounds of Formula VI
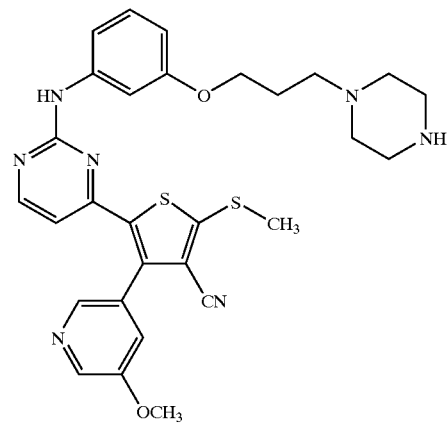
VI-56
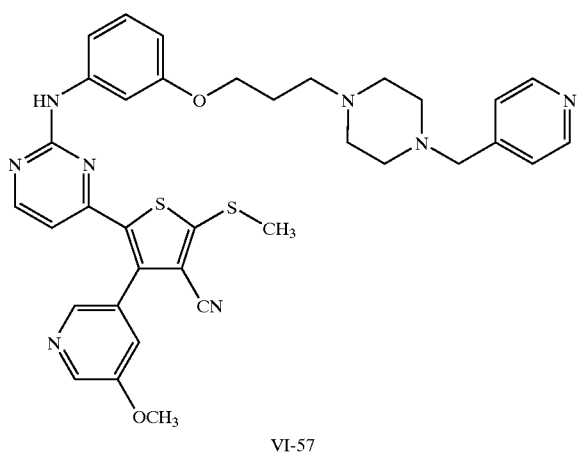
VI-57
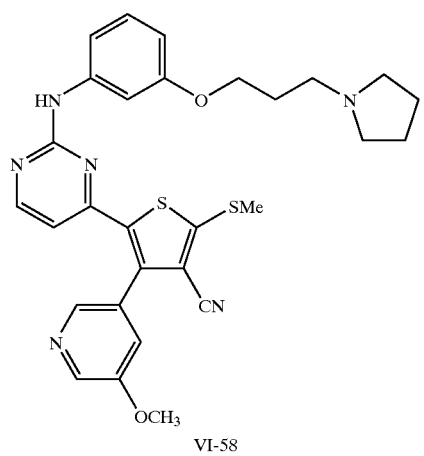
VI-58
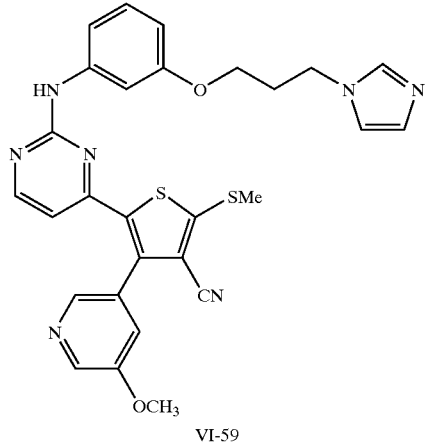
VI-59
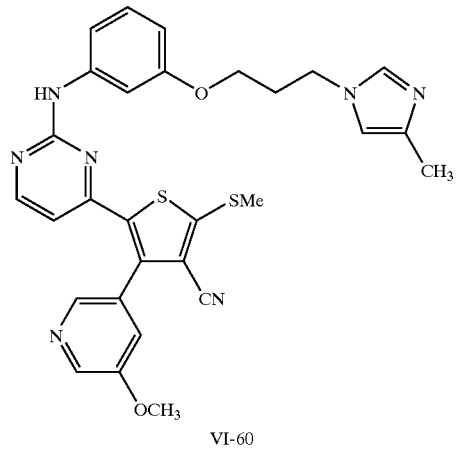
VI-60
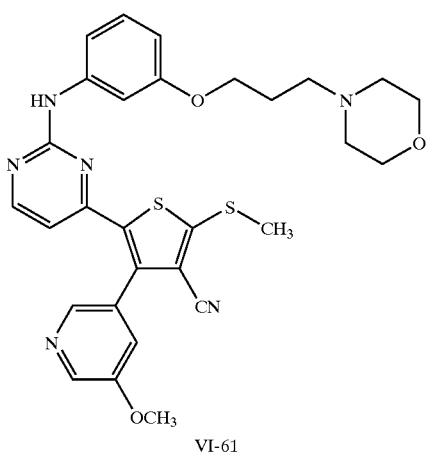
VI-61

TABLE 8-continued
Compounds of Formula VI
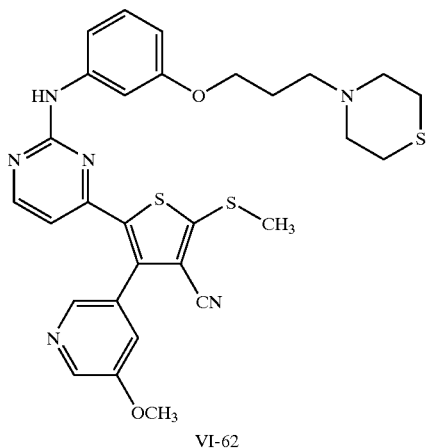
VI-62
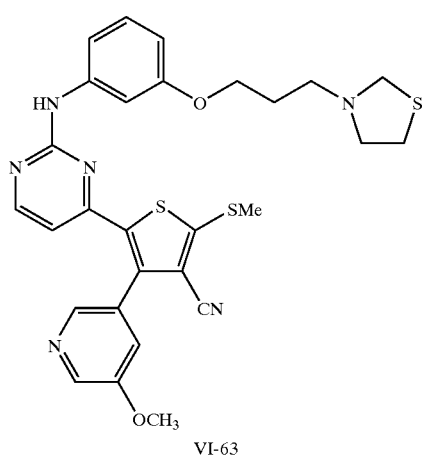
VI-63
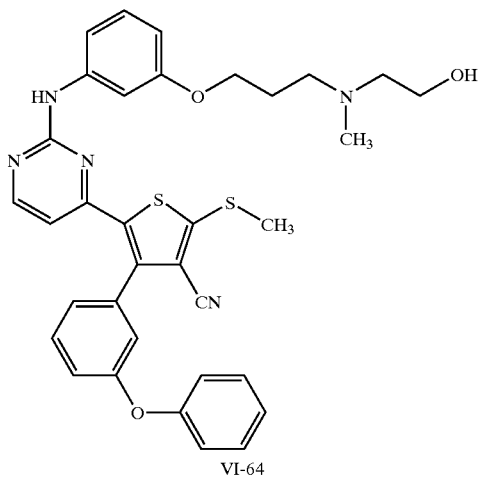
VI-64
TABLE 8-continued
Compounds of Formula VI
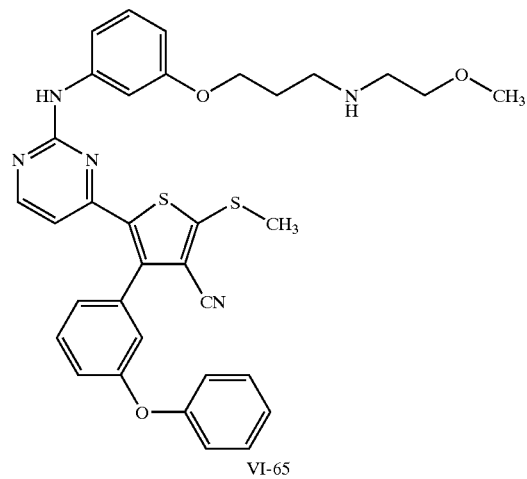
VI-65
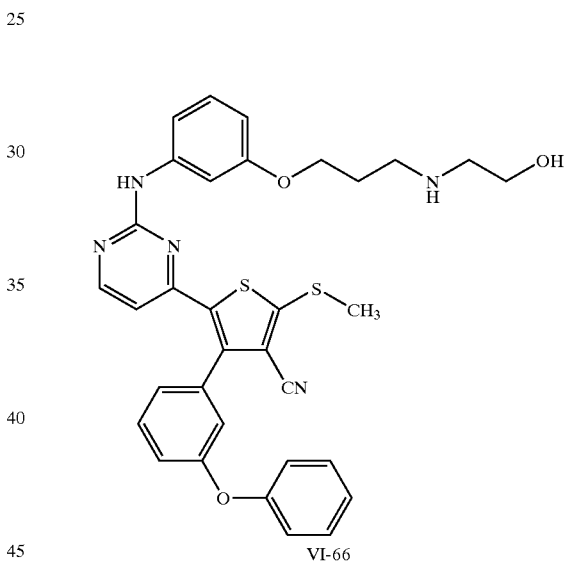
VI-66
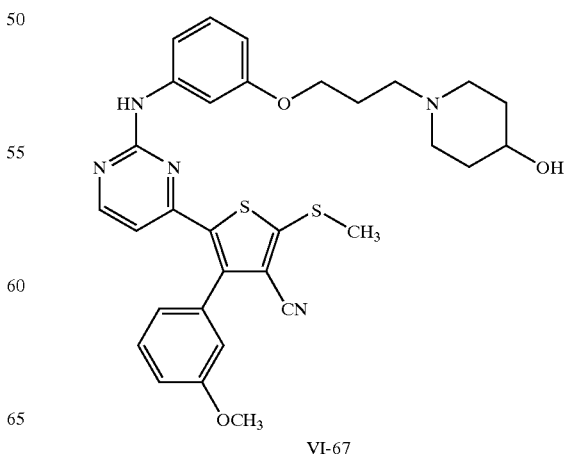
VI-67

TABLE 8-continued
Compounds of Formula VI
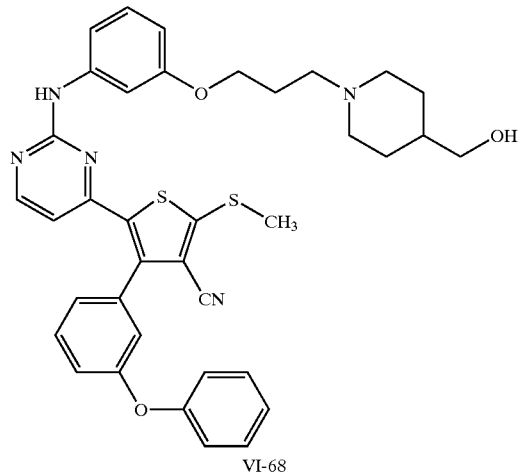
VI-68
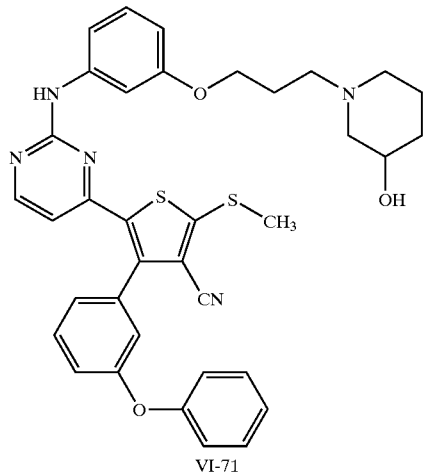
VI-71
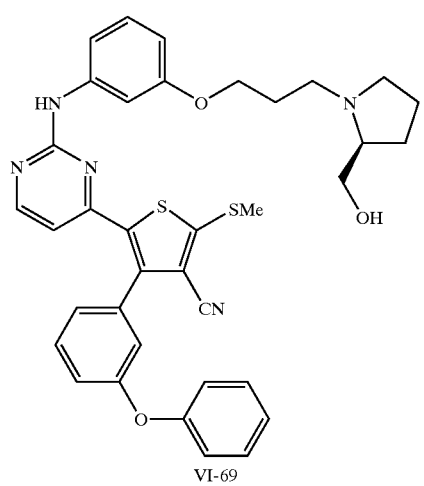
VI-69
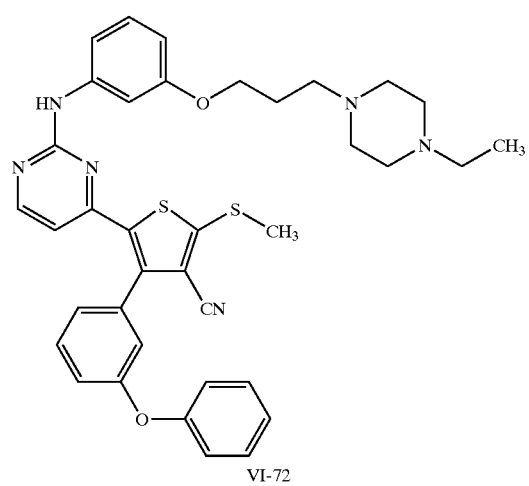
VI-72
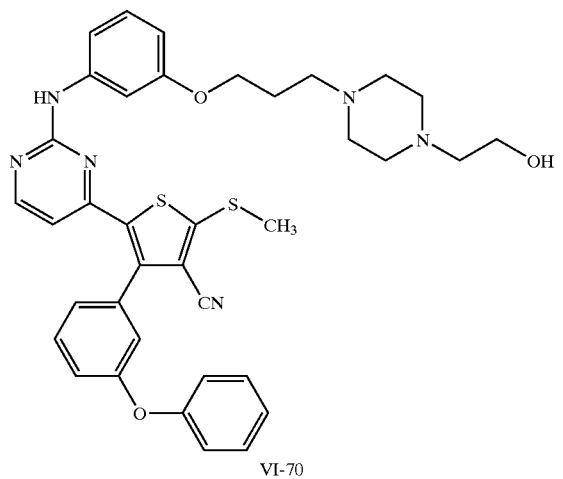
VI-70
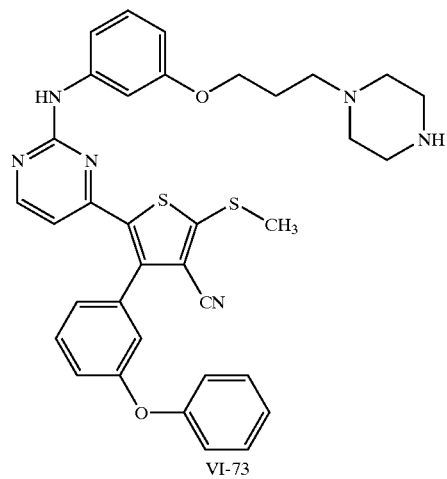
VI-73

TABLE 8-continued
Compounds of Formula VI
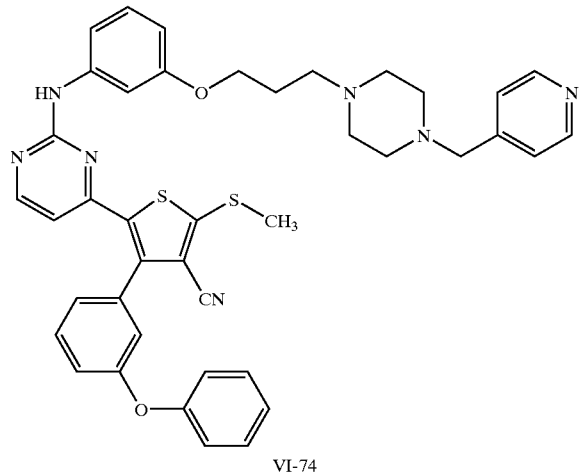
VI-74
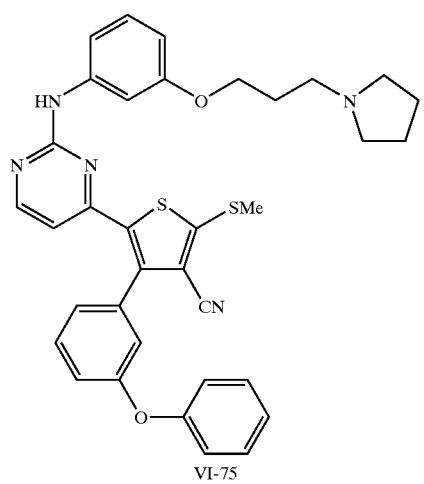
VI-75
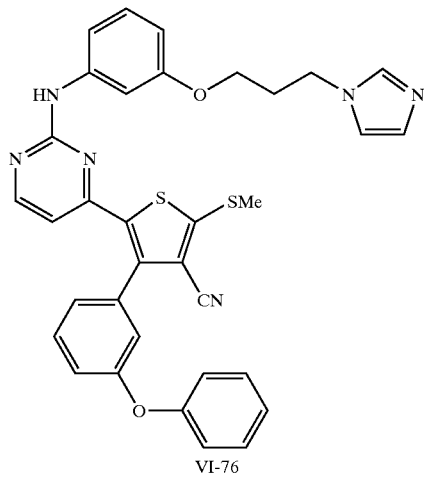
VI-76
TABLE 8-continued
Compounds of Formula VI
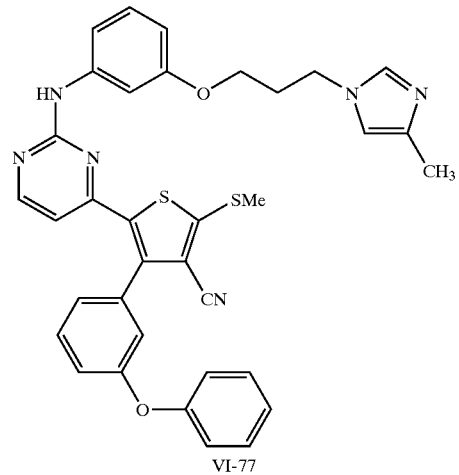
VI-77
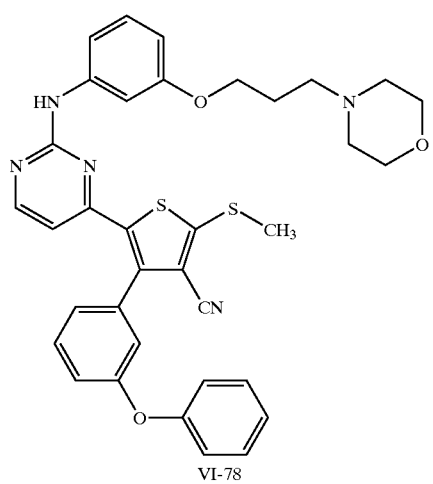
VI-78
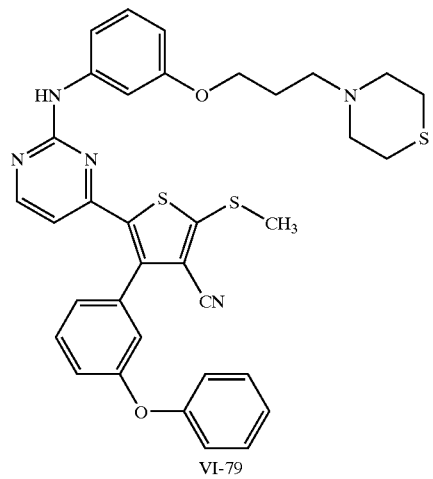
VI-79

TABLE 8-continued
Compounds of Formula VI
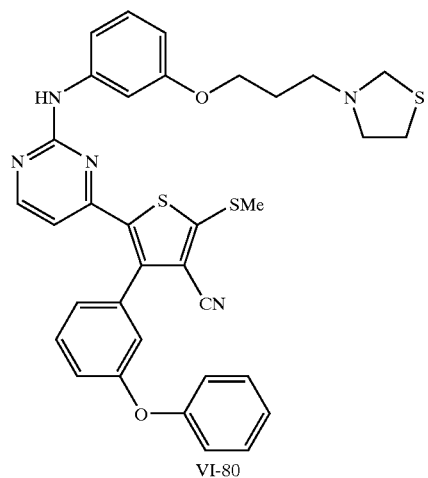
VI-80
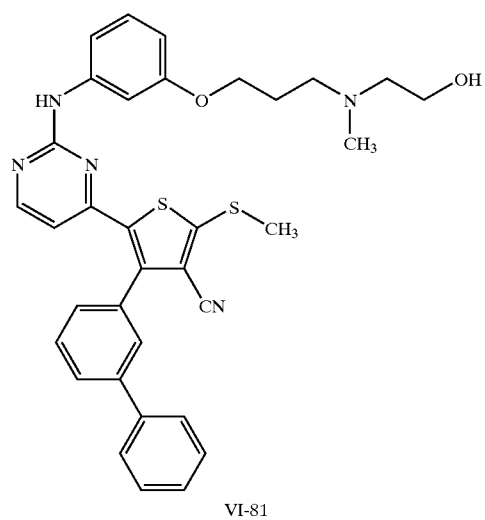
VI-81
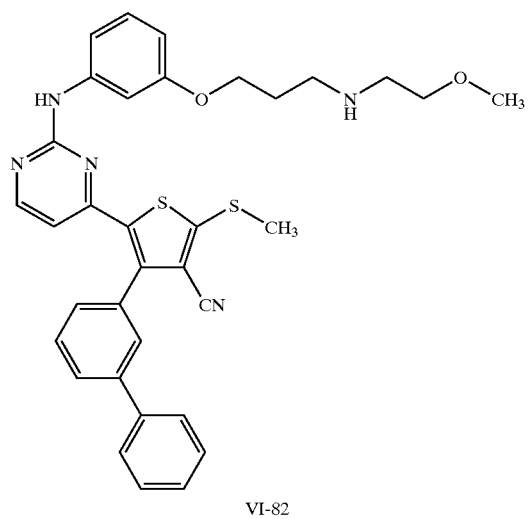
VI-82
TABLE 8-continued
Compounds of Formula VI
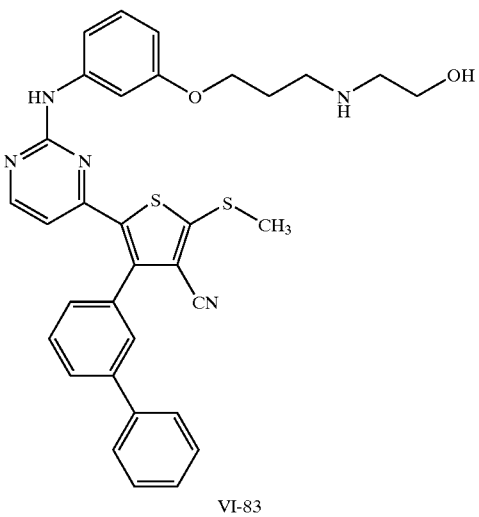
VI-83
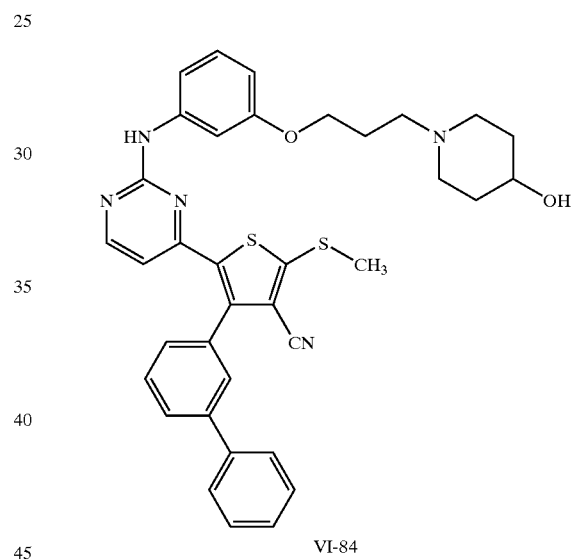
VI-84
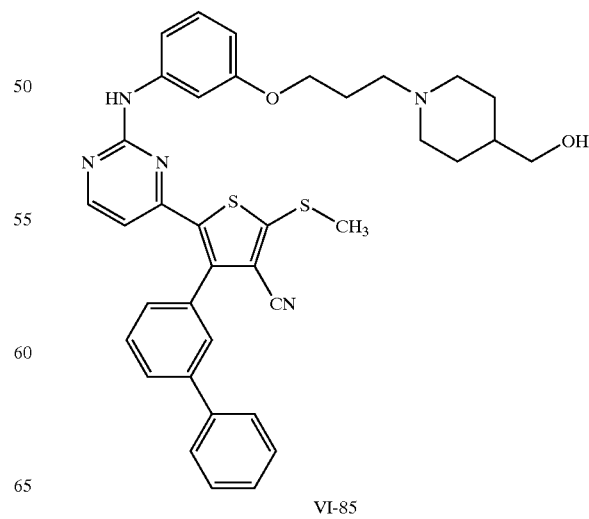
VI-85

TABLE 8-continued
Compounds of Formula VI
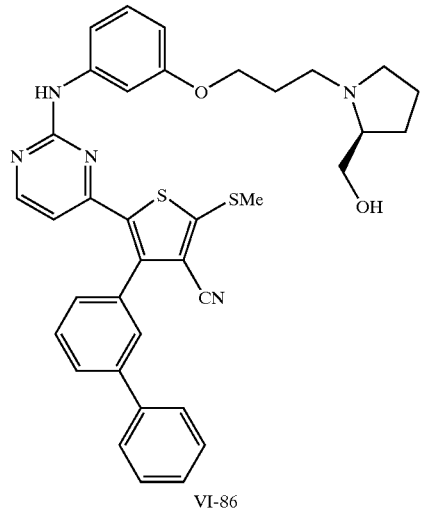
VI-86
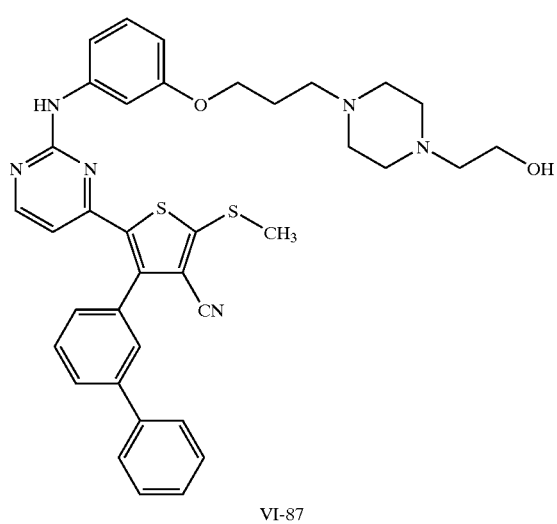
VI-87
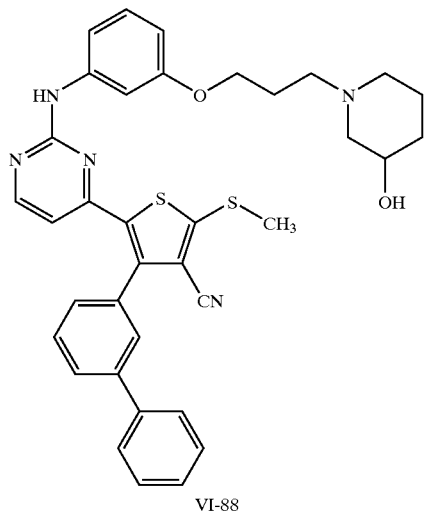
VI-88
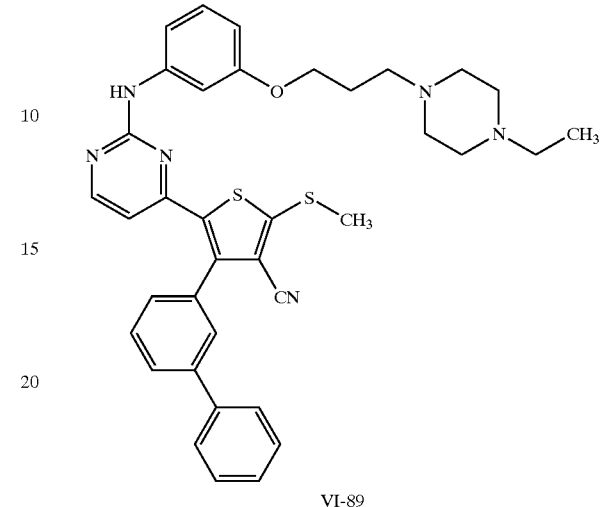
VI-89
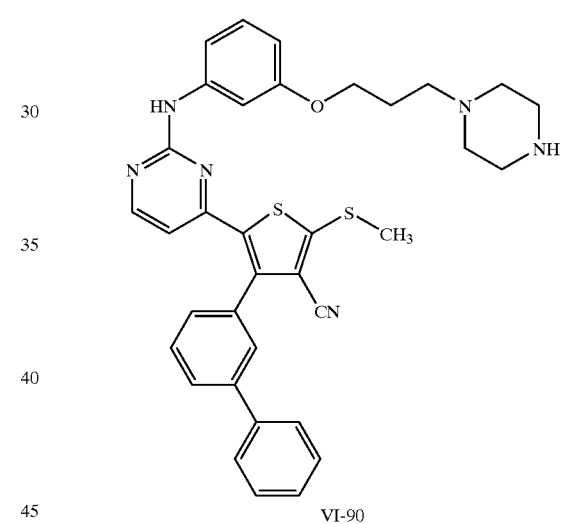
VI-90
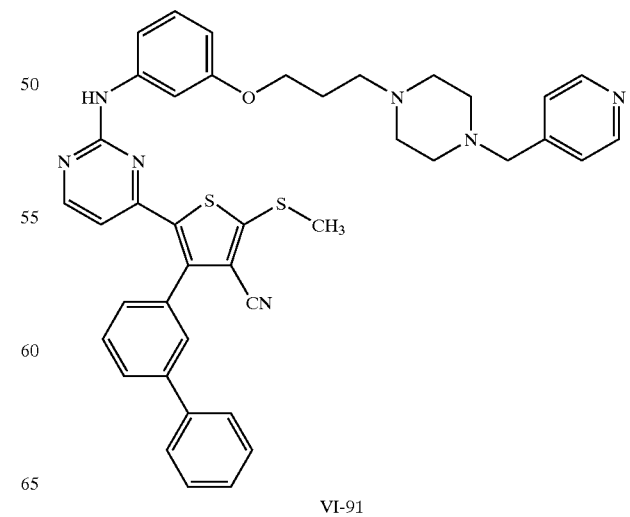
VI-91

TABLE 8-continued
Compounds of Formula VI
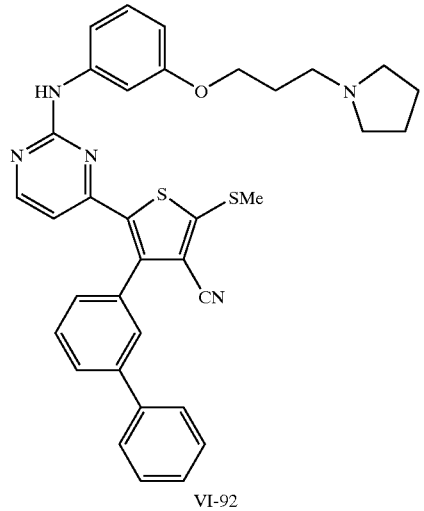
VI-92
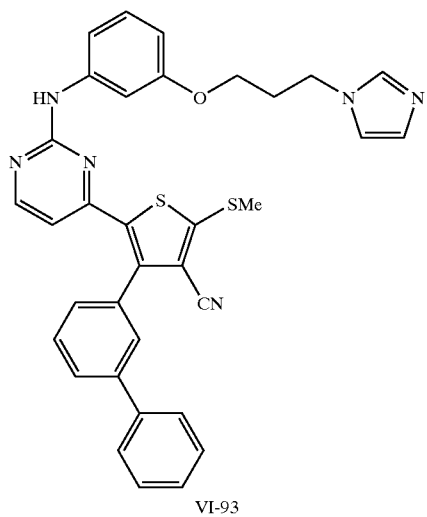
VI-93
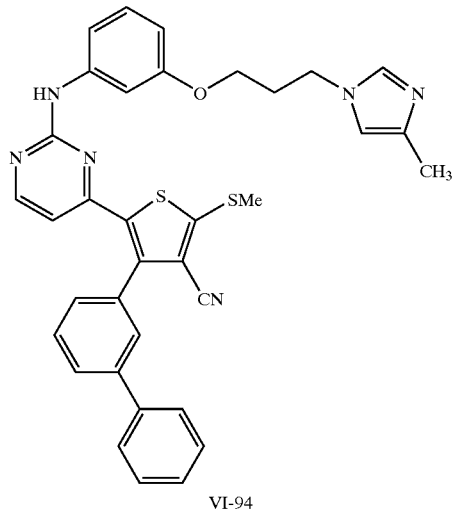
VI-94
TABLE 8-continued
Compounds of Formula VI
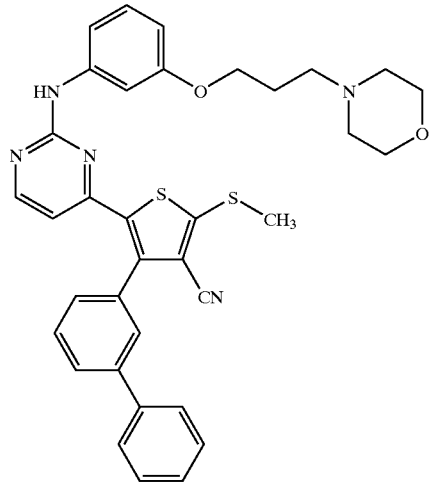
VI-95
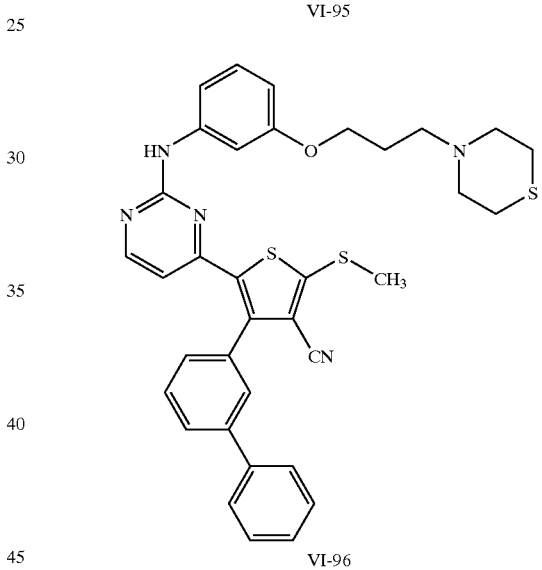
VI-96
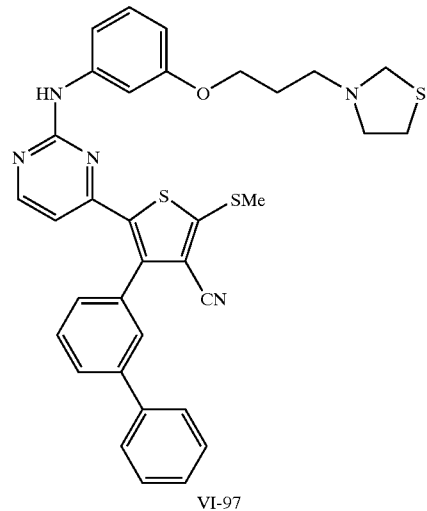
VI-97

TABLE 8-continued
Compounds of Formula VI
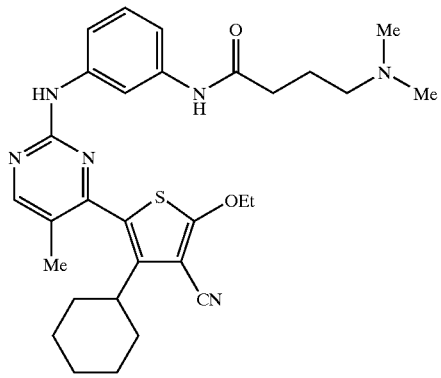
VI-98
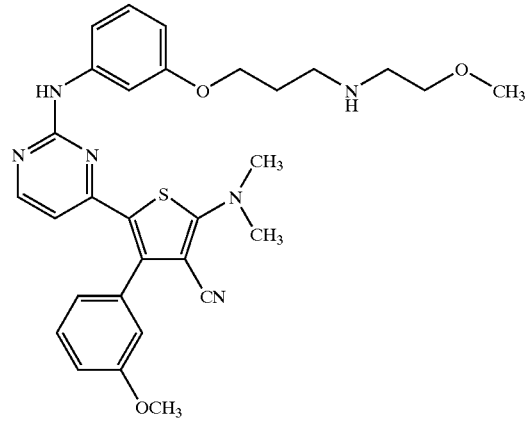
VI-101
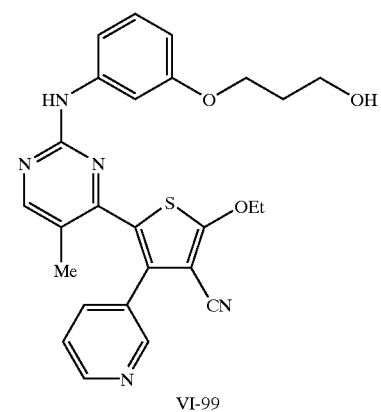
VI-99
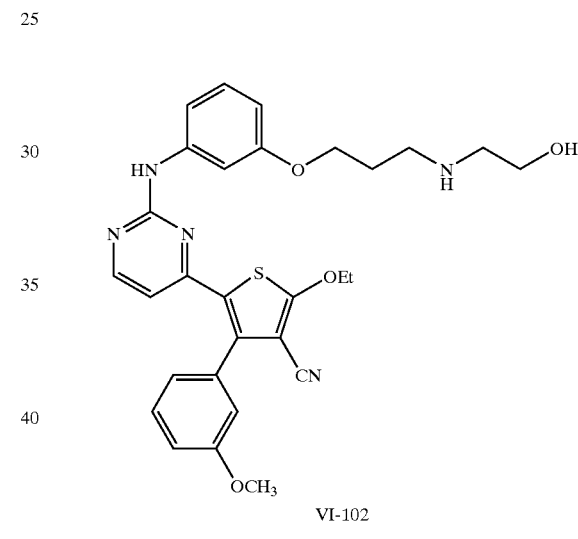
VI-102
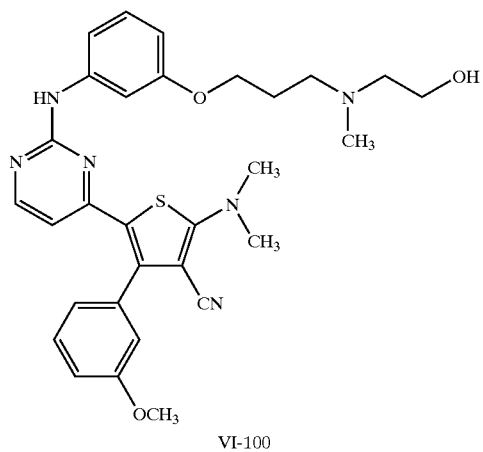
VI-100
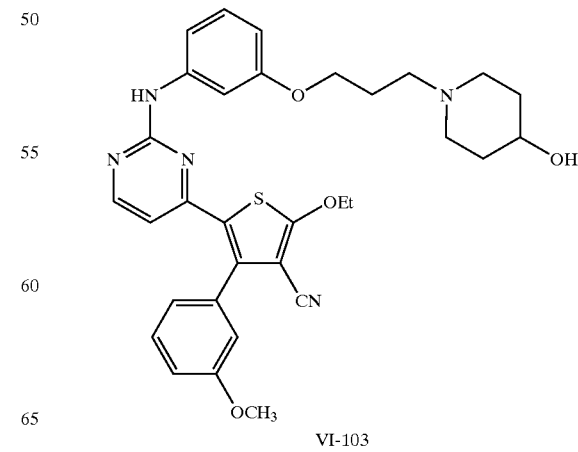
VI-103

TABLE 8-continued
Compounds of Formula VI
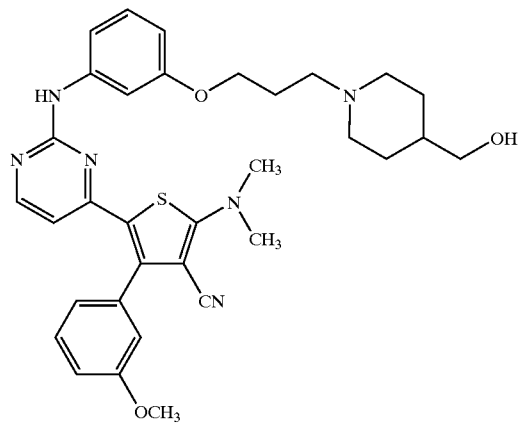
VI-104
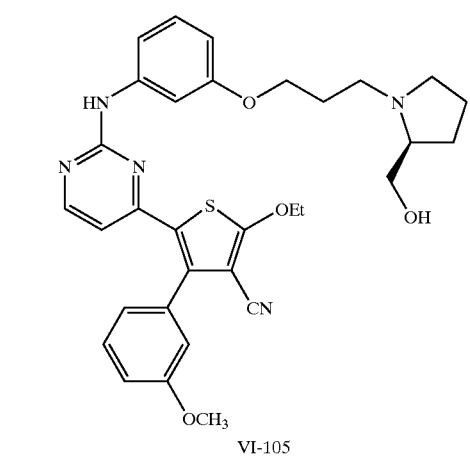
VI-105
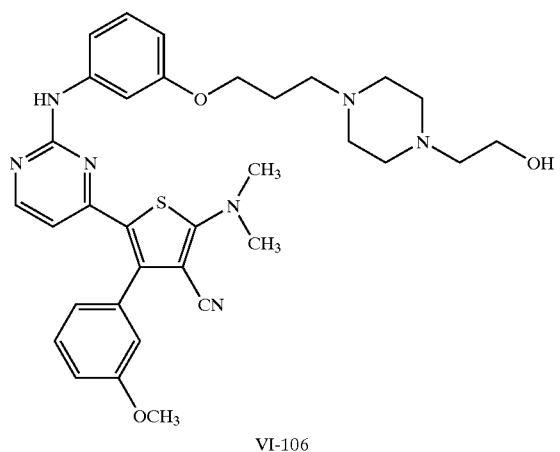
VI-106
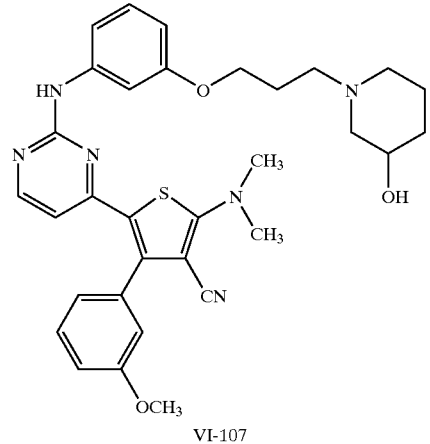
VI-107
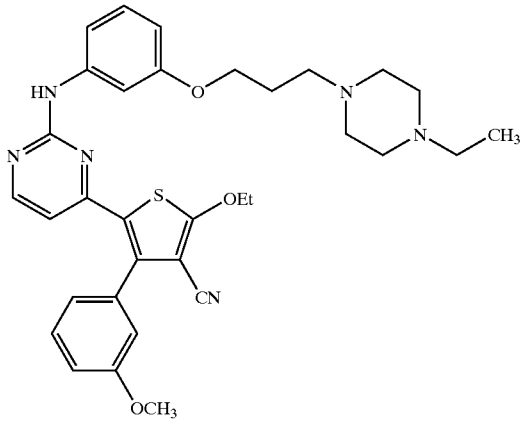
VI-108
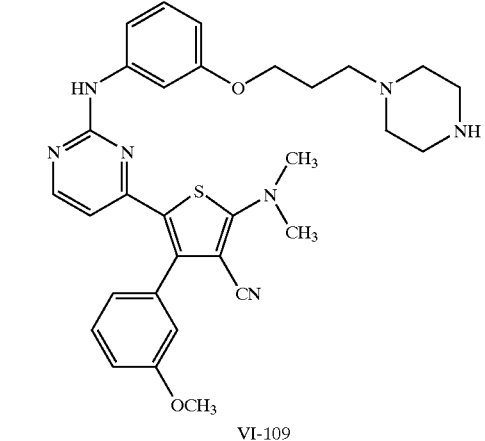
VI-109

TABLE 8-continued
Compounds of Formula VI
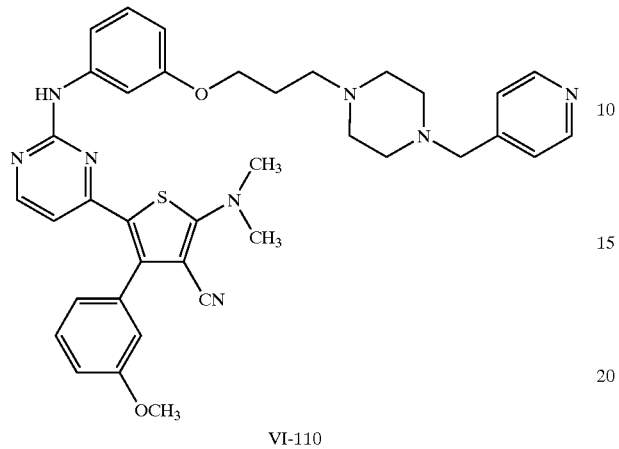
VI-110
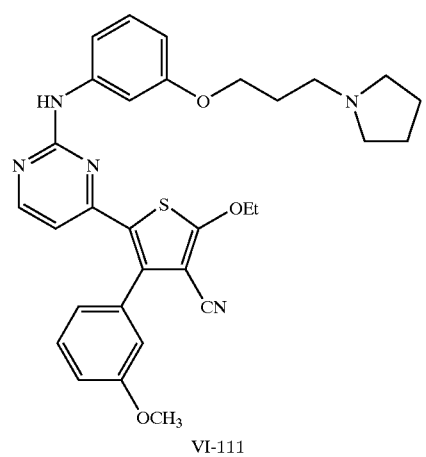
VI-111
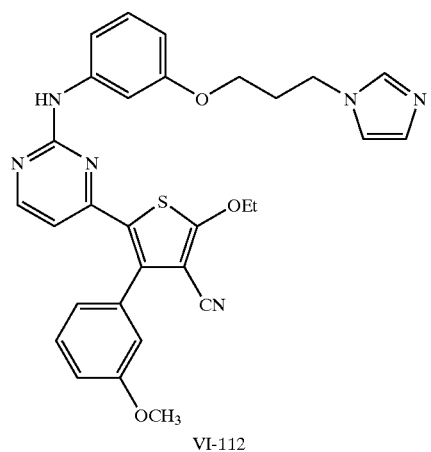
VI-112
TABLE 8-continued
Compounds of Formula VI
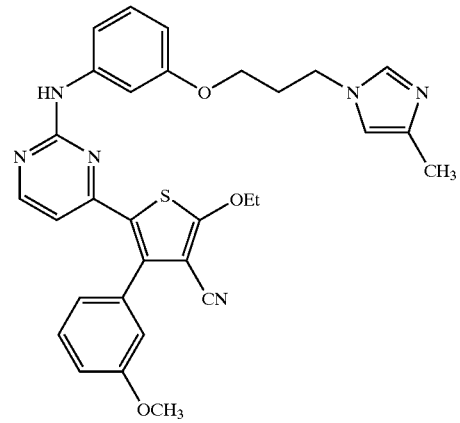
VI-113
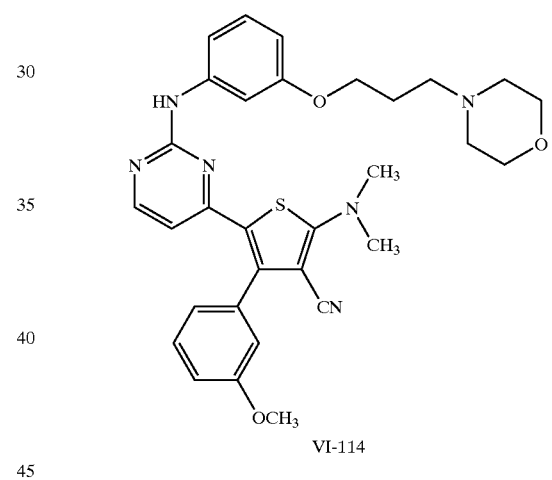
VI-114
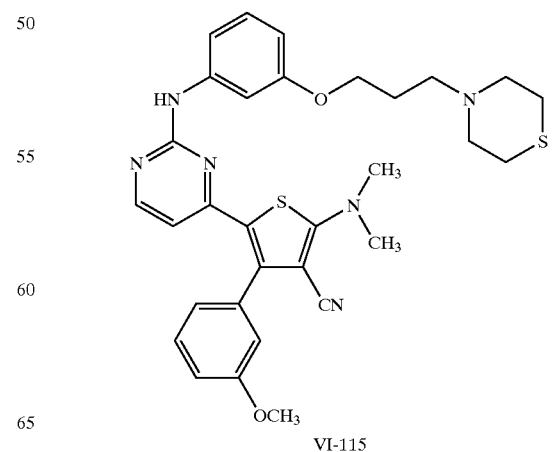
VI-115

TABLE 8-continued
Compounds of Formula VI
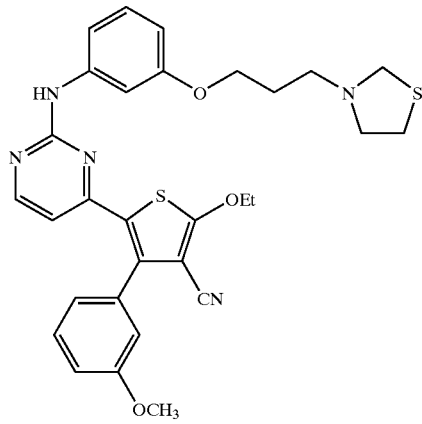
VI-116
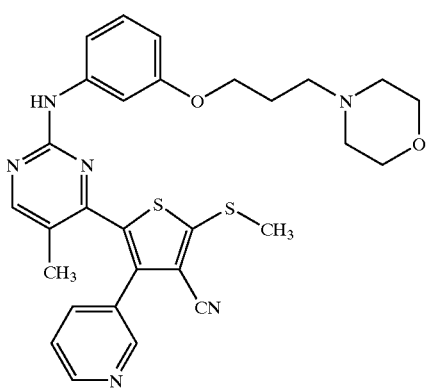
VI-117
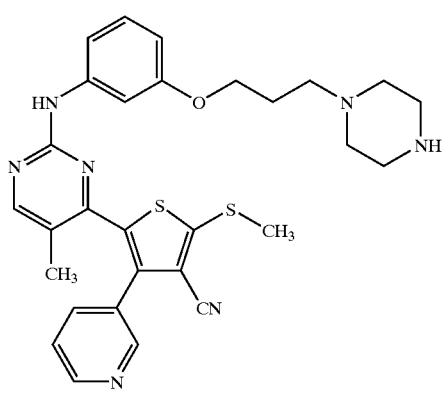
VI-118
TABLE 8-continued
Compounds of Formula VI
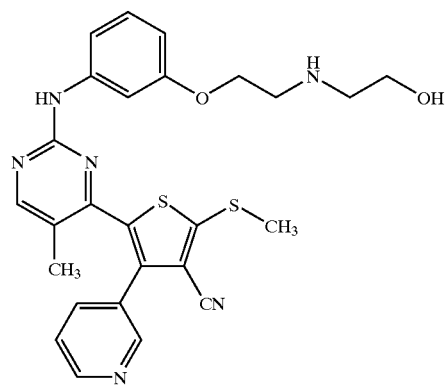
VI-119
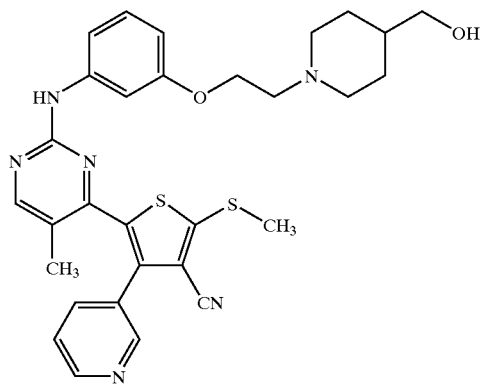
VI-120
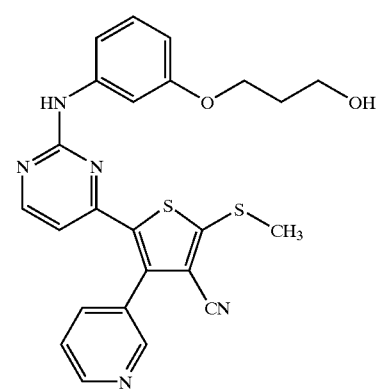
VI-121

TABLE 8-continued
Compounds of Formula VI
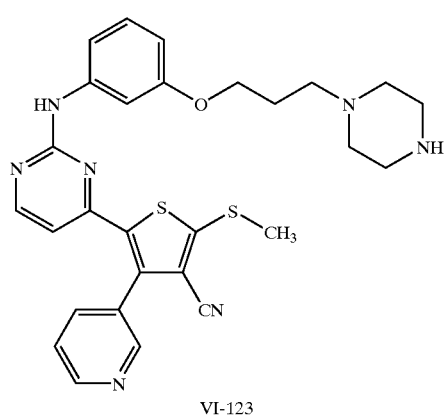
VI-122
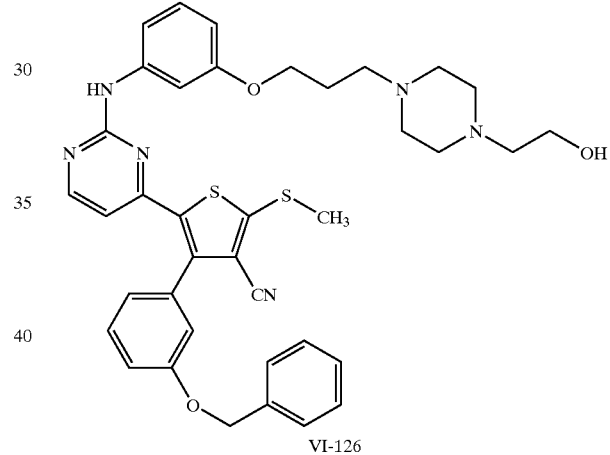
VI-125
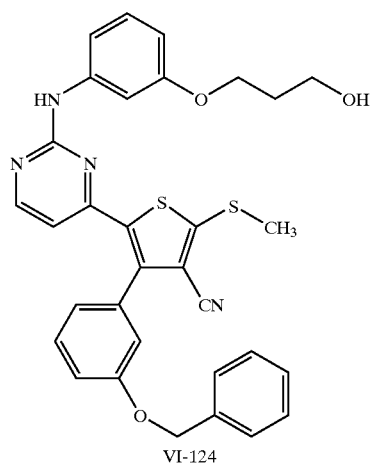
VI-123
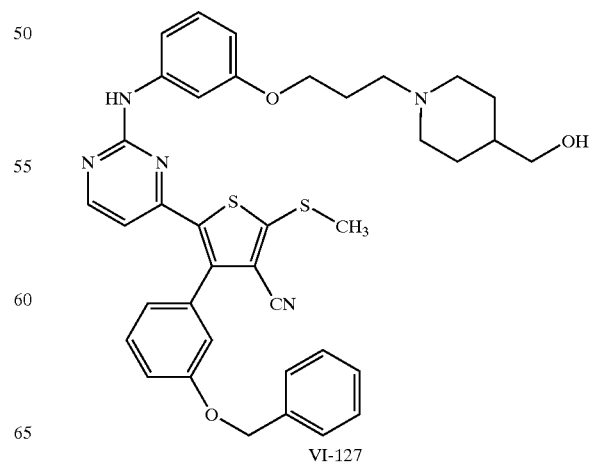
VI-126
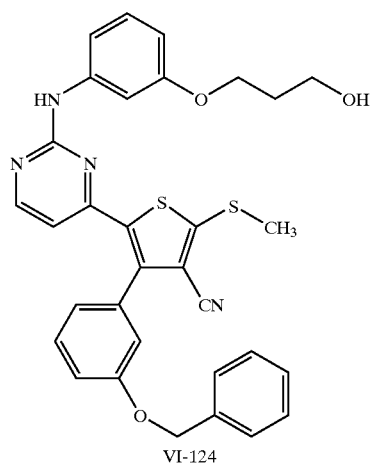
VI-124
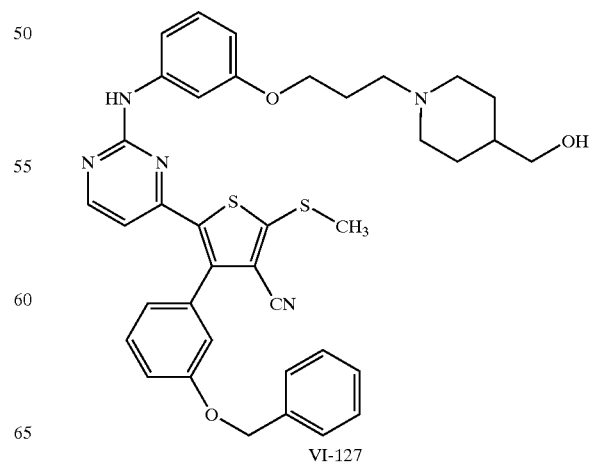
VI-127

TABLE 8-continued
Compounds of Formula VI
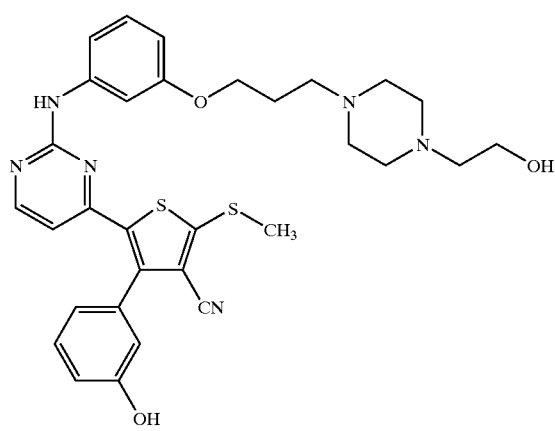
VI-128
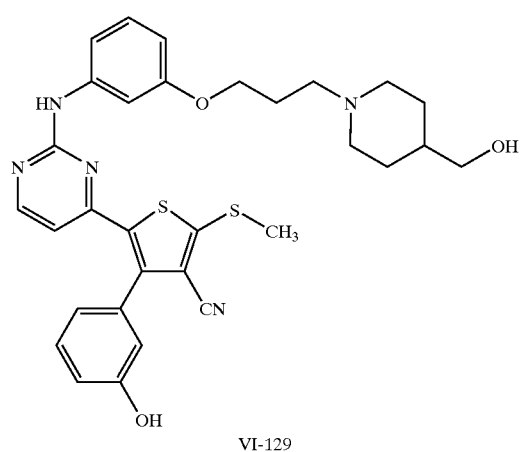
VI-129
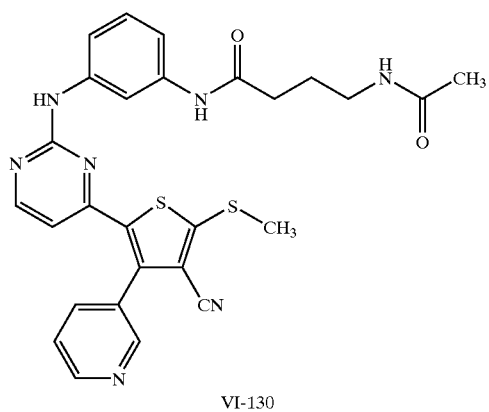
VI-130
TABLE 8-continued
Compounds of Formula VI
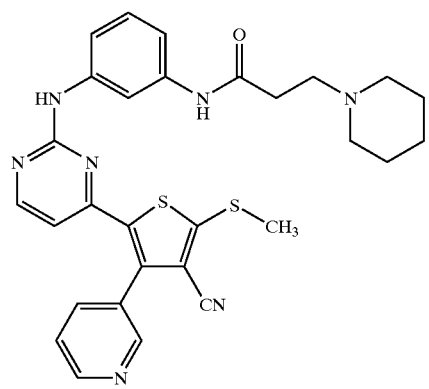
VI-131
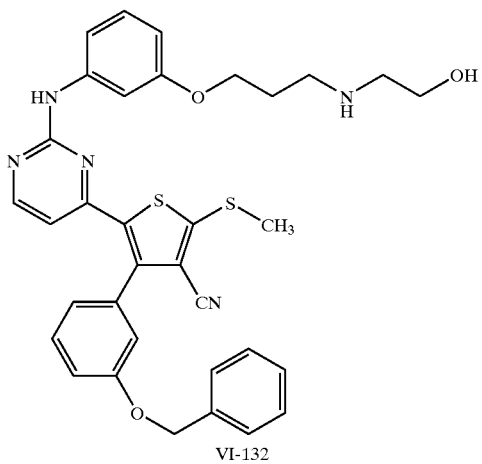
VI-132
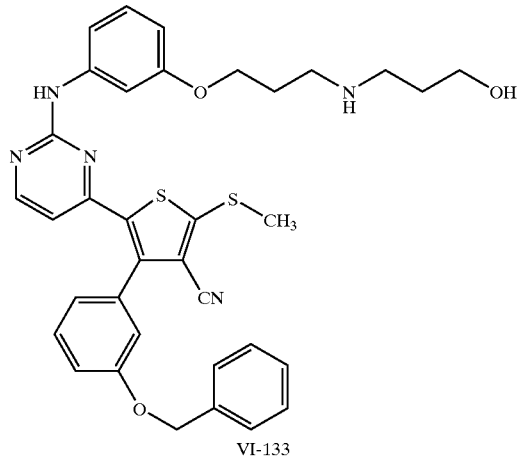
VI-133

TABLE 8-continued
Compounds of Formula VI
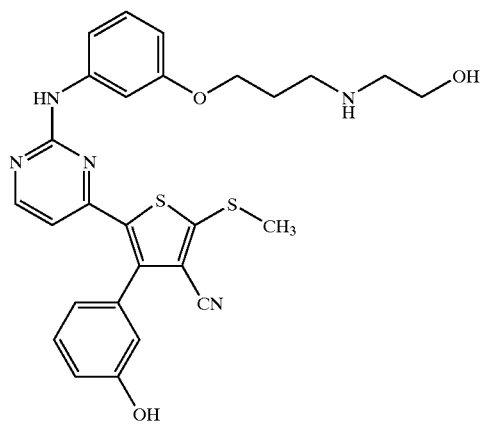
VI-134
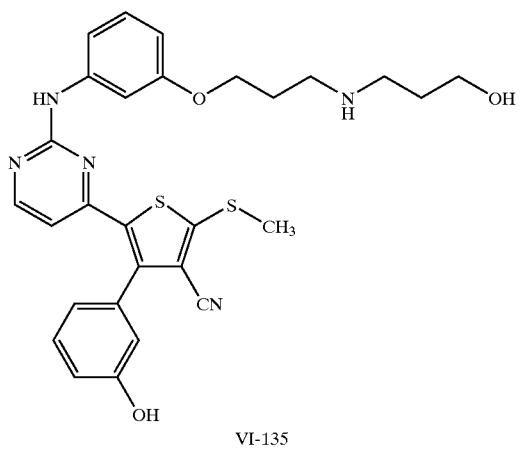
VI-135
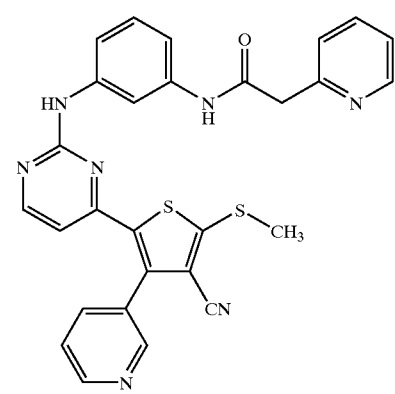
VI-136
TABLE 8-continued
Compounds of Formula VI
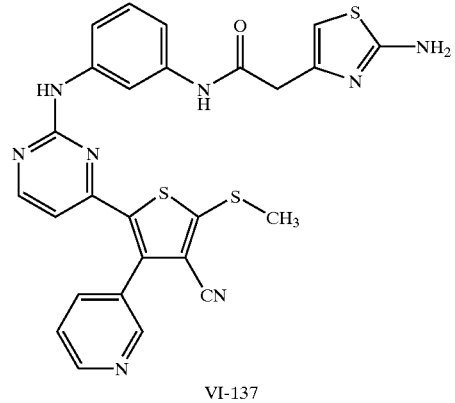
VI-137
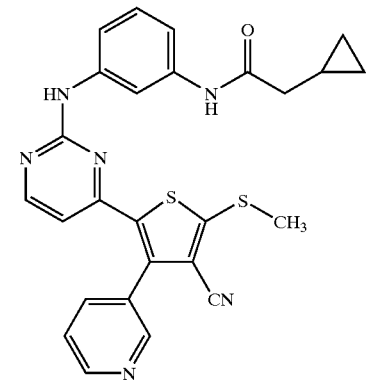
VI-138
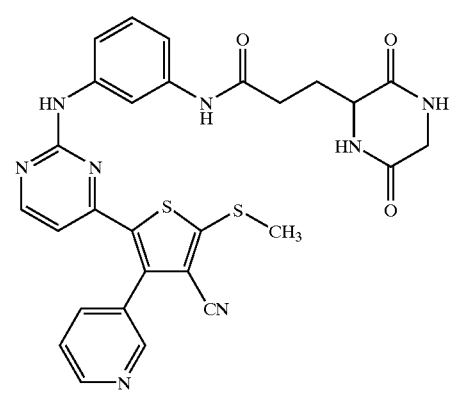
VI-139

TABLE 8-continued
Compounds of Formula VI
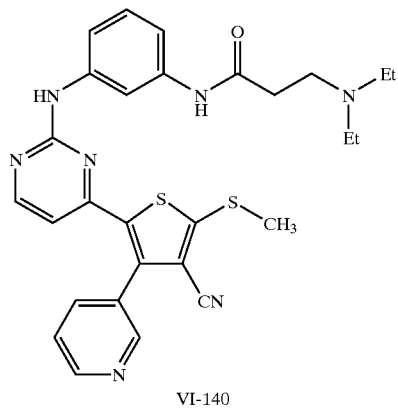
VI-140
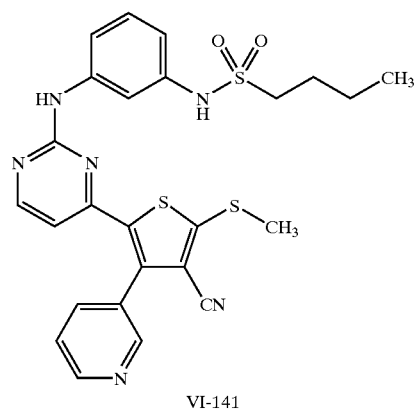
VI-141
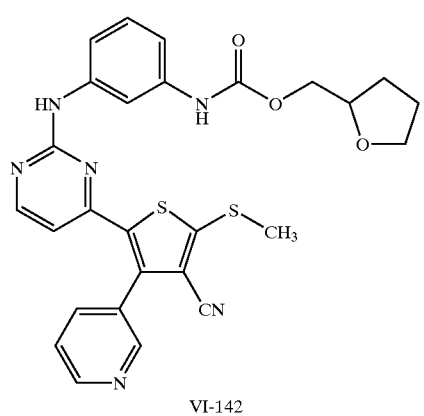
VI-142
TABLE 8-continued
Compounds of Formula VI
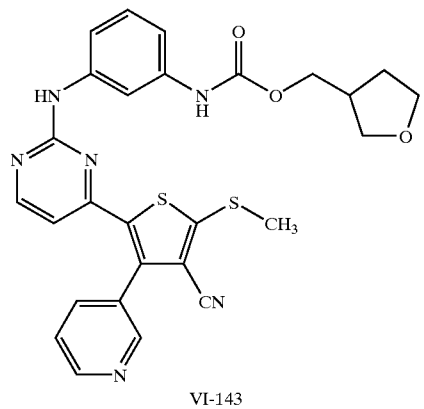
VI-143
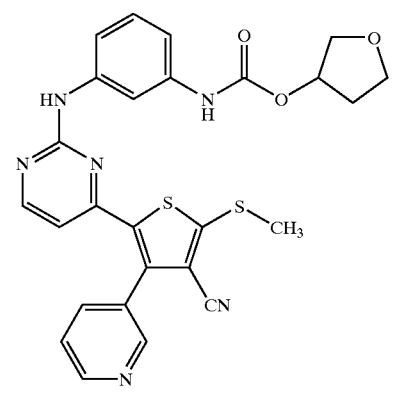
VI-144
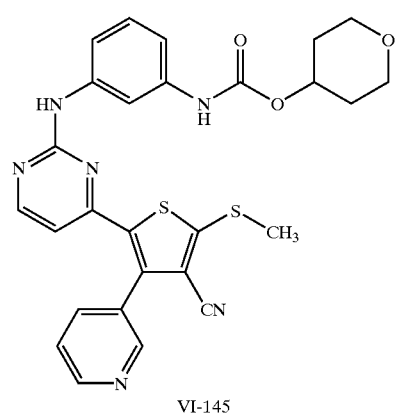
VI-145

TABLE 8-continued

Compounds of Formula VI

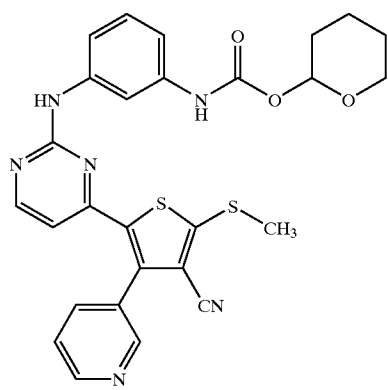
VI-146

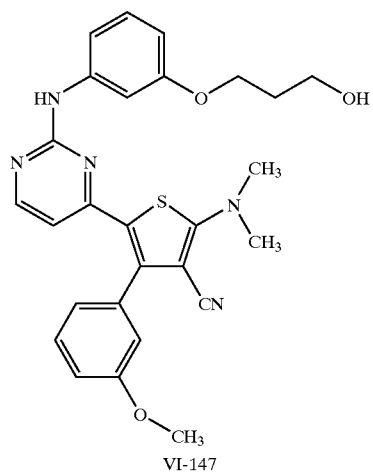
VI-147

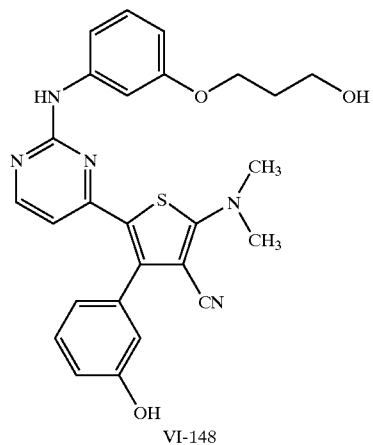
VI-148

TABLE 8-continued

Compounds of Formula VI

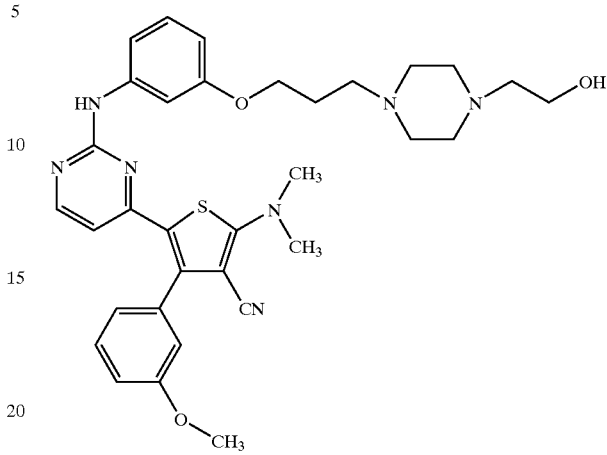
VI-149

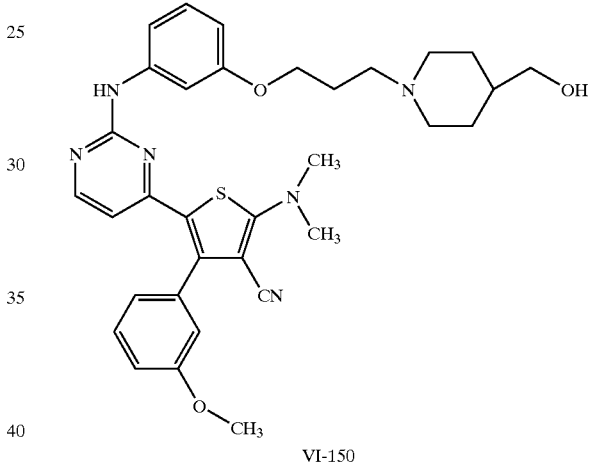
VI-150

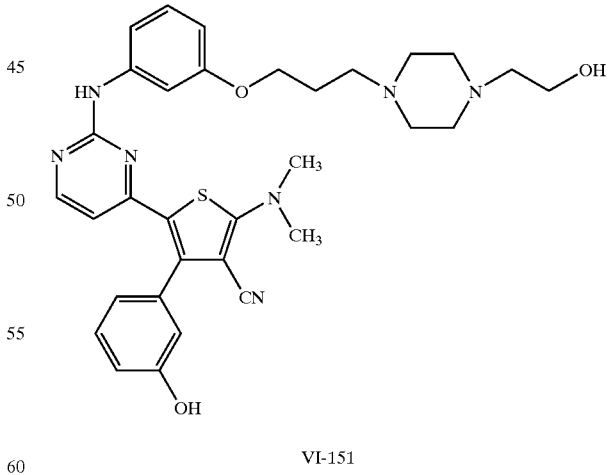
VI-151

The above formula VI compounds are those having a pyrimidine ring. Compounds of formula VI having a pyridine or triazine ring are otherwise structurally similar to the formula VI compounds and are represented by the following general formulae VII and VIII shown below:

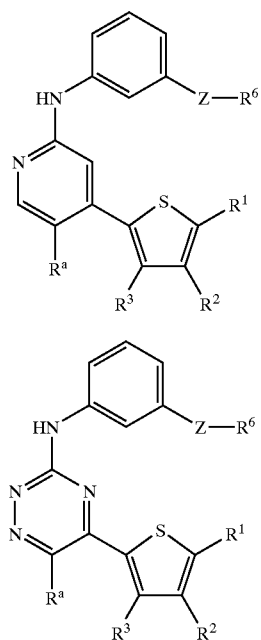

The compounds of formulae VII and VIII shown above are structurally similar to compounds of formula VI where the pyrimidine ring of formula VI is replaced by a pyridine (VII) or triazine ring (VIII). Accordingly, preferred $R^1$, $R^2$, $R^3$, and Z—$R^6$ groups of the compounds of formulae VII and VIII are as described above for the formula VI compounds.

The present compounds may be prepared in general by methods known to those skilled in the art for analogous compounds, as illustrated by the general Schemes I, II, III, IV, V, and VI, and the synthetic examples shown below.

Scheme I

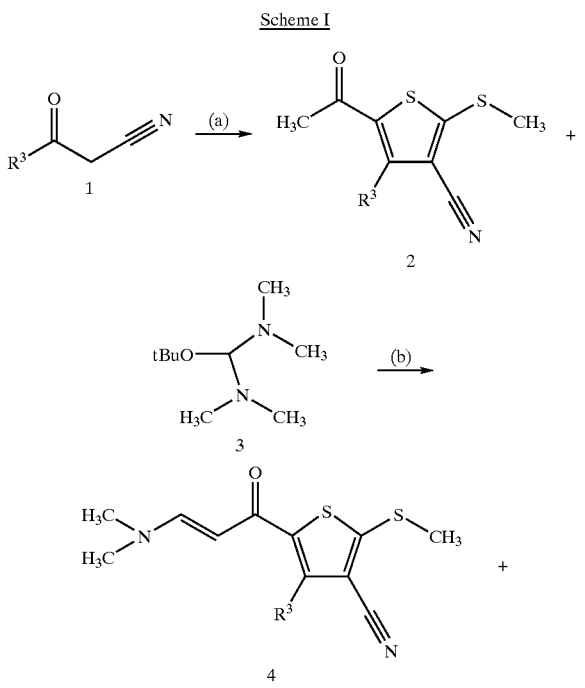

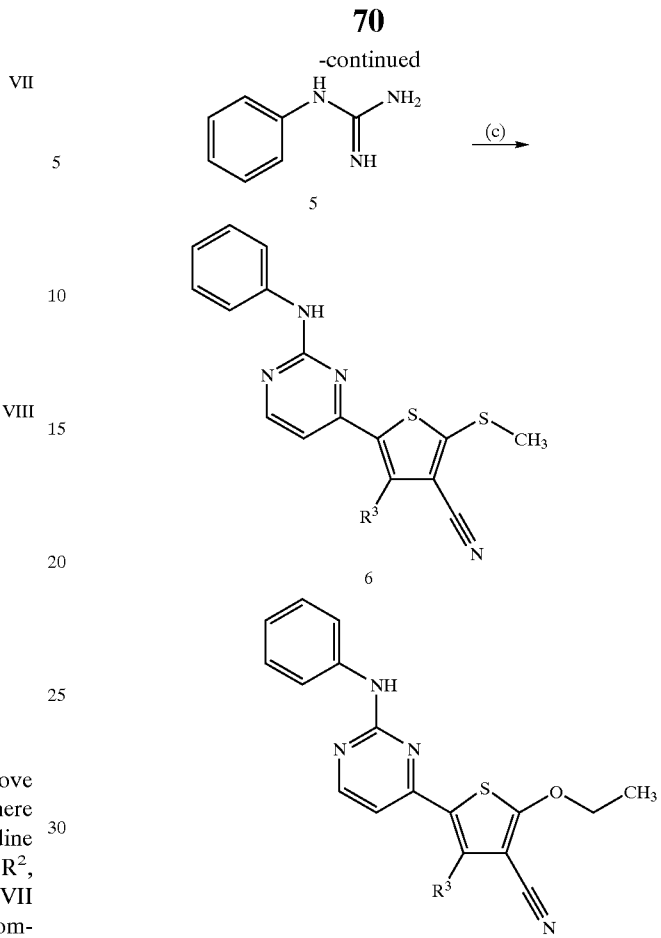

Reagents and conditions:
(a) $K_2CO_3$, DMF, $CS_2$, 1-chloro-propan-2-one, MeI, in DMF at r. t.;
(b) THF, r. t.;
(c) NaOEt, EtOH, 90° C.

Scheme I above shows a general synthetic route that is used for preparing the compounds of formula IIa where $R^2$ is CN. These compounds are prepared in a parallel fashion in the following manner. In step (a), α-cyanoacetophenone (1) is combined with $K_2CO_3$ (3 equivalents) in DMF and the mixture allowed to stir at room temperature. $CS_2$ (1.5 equivalents) is then added and the resulting mixture stirred at room temperature for an additional 10 minutes. A solution of 1-chloro-propan-2-one (1.0 equivalent) in DMF is added, then a solution of MeI (1.1 equivalents) in DMF is added in a dropwise fashion. After 30 minutes, the mixture is poured onto water and the resulting mixture stirred vigorously for 12–16 hours to afford a suspension of compound 2. The crude product 2 is isolated by filtration. This reaction may be used to obtain compounds of this invention derived from α-cyanoacetophenones having a wide variety of phenyl substituents. Examples of suitable $R^3$ groups include, but are not limited to, those set forth in Table 1 above.

In step (b), the crude product 2 is combined with t-butoxybisdimethylaminomethane (Brederick's reagent, 3) in THF and allowed to stir at room temperature for 12–16 hours. The reaction mixture is concentrated then used directly for step (c). The crude concentrate 4 is dissolved in EtOH. Compound 5 is added to the ethanolic solution and the resulting mixture heated to 90° C. for 4 hours. Although Scheme I uses phenyl guanidine at step (c), it would be obvious to one of skill in the art that other aryl guanidines may be used at step (c) to prepare compounds of the present invention where $R^4$ is a variety of optionally substituted aryl groups. The reaction mixture is concentrated then, after aqueous work-up, the product is purified by preparatory HPLC to afford compounds 6 and 7. The details of the conditions used for producing these compounds are set forth in the Examples.

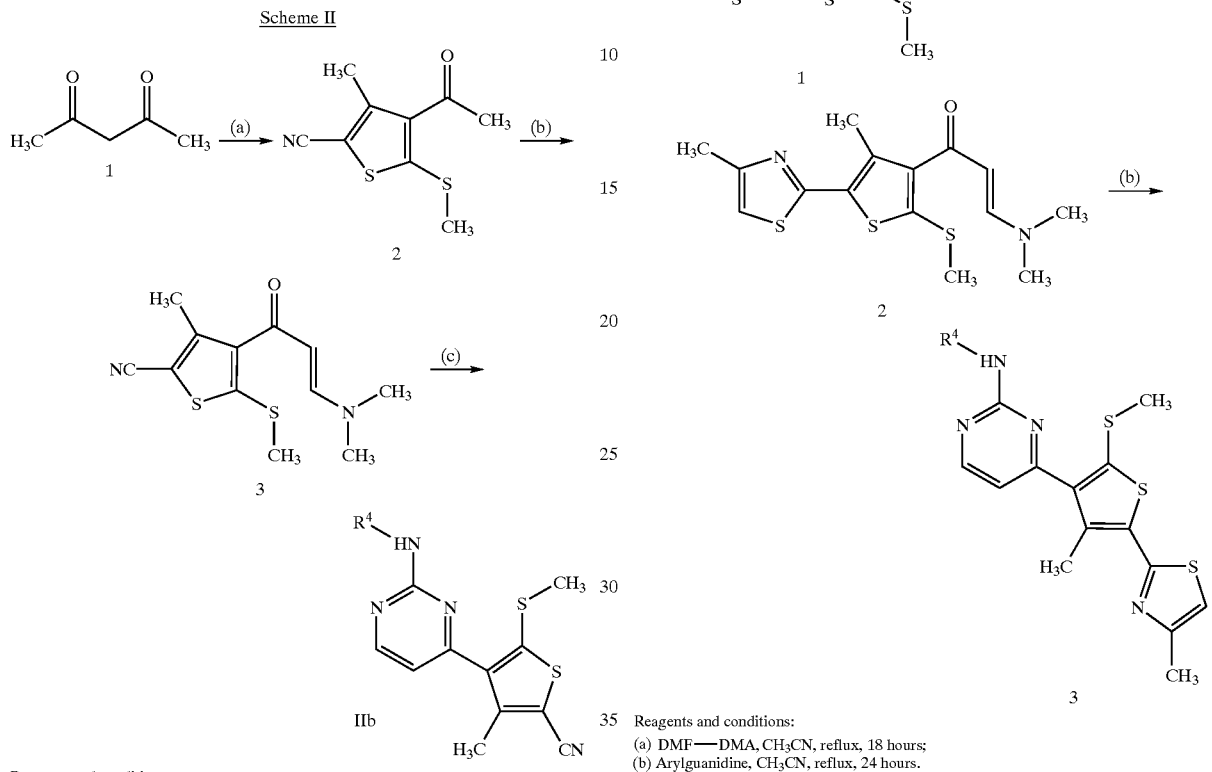

Reagents and conditions:
(a) (i) $K_2CO_3$, $CS_2$, DMF, $CH_3CN$, chloroacetonitrile, 0° C., 2 hours;
  (ii) MeI, room temperature 12 hours;
(b) DMF—DMA, $CH_3CN$, reflux, 18 hours;
(c) Arylguanidine, $CH_3CN$, reflux, 24 hours.

Scheme II above shows a general synthetic route that is used for preparing the compounds of formula IIb where $R^3$ is methyl and $R^4$ is an optionally substituted aryl group.

Intermediate 4 is prepared by treating 2,4-pentanedione (1) with potassium carbonate (3 equivalents), $CS_2$ (2) (1.5 equivalents) and chloroacetonitrile (1.0 equivalents) in DMF at room temperature for 2 hours. The mixture is cooled to 0° C. then methyl iodide (3) is added slowly and the resulting mixture stirred at room temperature for 12 hours. Water is added to precipitate the product which is isolated by filtration to afford 4.

Intermediate 5 is prepared by treating 4 with dimethylformamide-dimethyl acetal (DMF-DMA) in acetonitrile at reflux for 18 hours. The product 5 is isolated as a yellow solid from trituration with ether.

Compounds of formula IIb are prepared from 5 by combining 5 with an aryl guanidine in acetonitrile and heating the resulting mixture at reflux for 24 hours. Methanol is added to the reaction mixture to precipitate the product and the resulting suspension filterred to afford product IIb. The details of the conditions used for producing these compounds are set forth in the Examples.

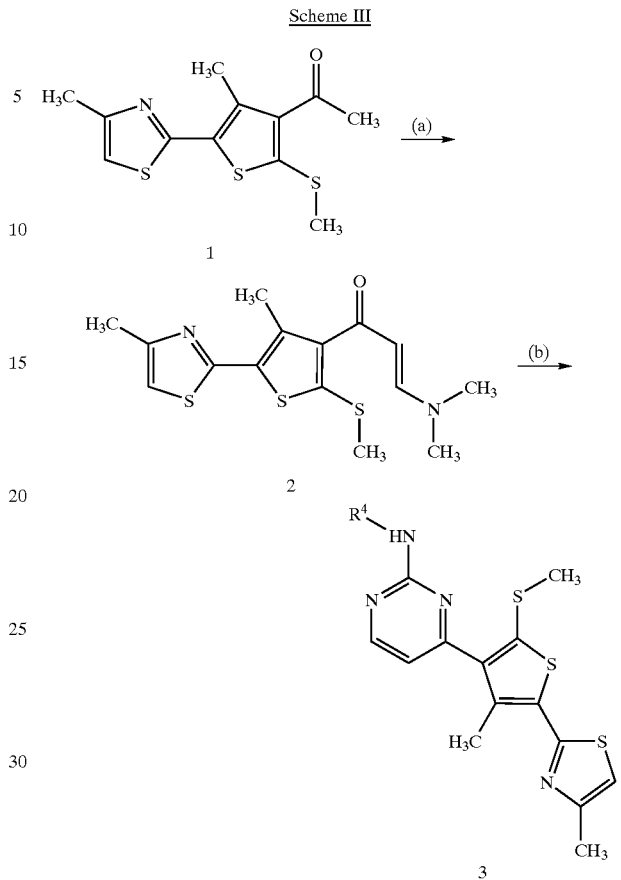

Reagents and conditions:
(a) DMF—DMA, $CH_3CN$, reflux, 18 hours;
(b) Arylguanidine, $CH_3CN$, reflux, 24 hours.

Scheme III above shows a general synthetic route that is used for preparing the compounds of formula IIb where $R^3$ is methyl, $R^4$ is an optionally substituted aryl group, and $R^2$ is 4-methylthiazol-2-yl.

1-[4-Methyl-2-methylsulfanyl-5-(4-methylthiazol-2-yl)-thiophen-3-yl]-ethanone (1) (Maybridge Chemicals) is treated with DMF-DMA in acetonitrile at reflux for 18 hours. The mixture is concentrated in vacuo and the residue triturated with diethyl ether to afford 2 as a yellow solid.

Intermediate 2 is combined with an aryl guanidine in acetonitrile and the resulting mixture heated at reflux for 24 hours. After cooling to room temperature, methanol is added to precipitate the product. The product 3 is isolated by filtration after methanol washes. The details of the conditions used for producing these compounds are set forth in the Examples.

Scheme IV

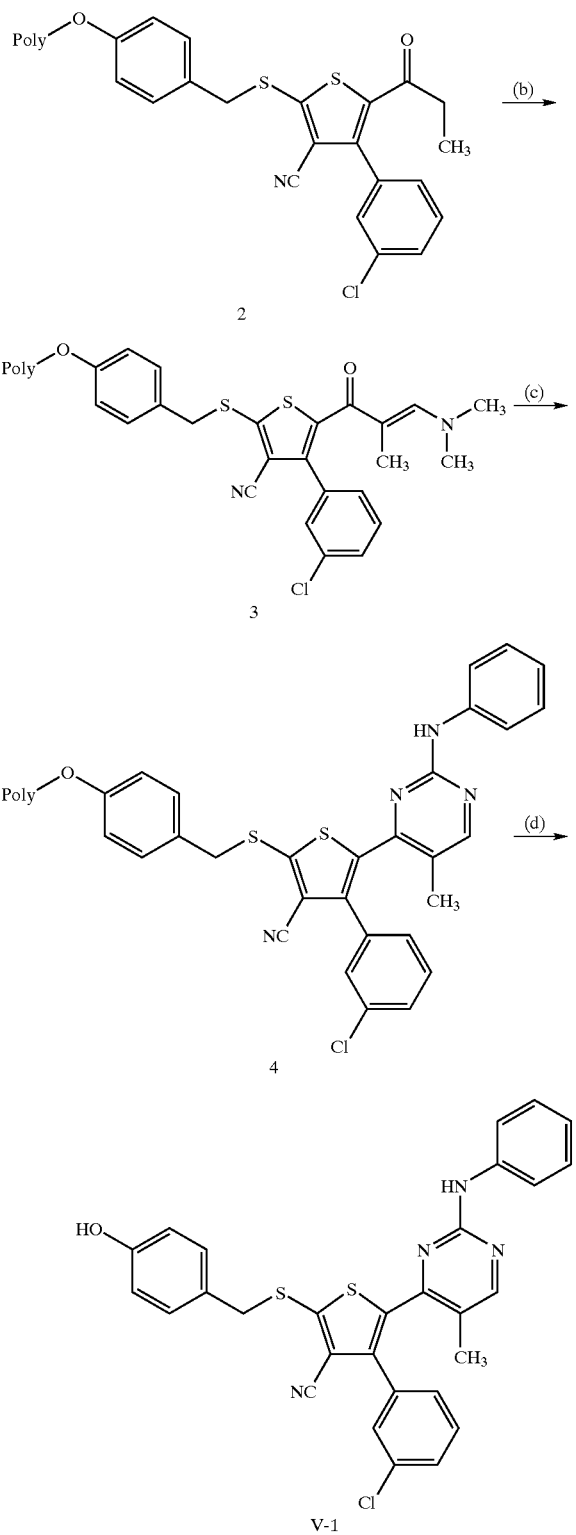

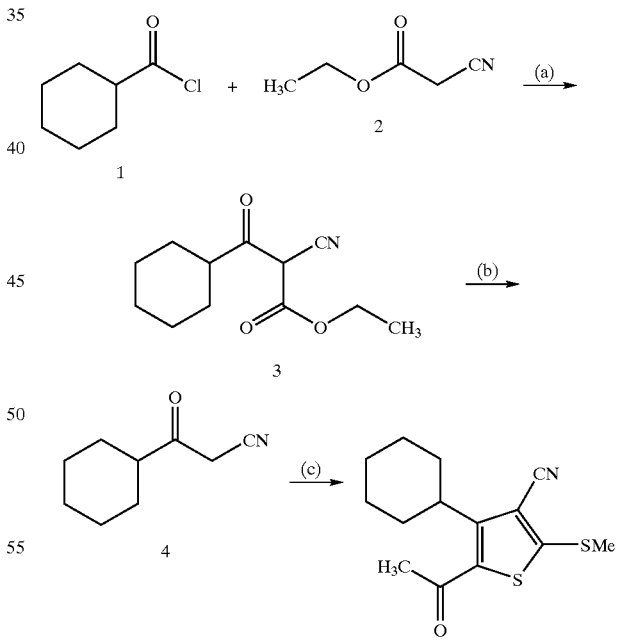

Using the preparation of compound V-1 as an example, Scheme IV above shows a general synthetic route that may be used to prepare compounds of formula V in parallel fashion in the following manner. In step (a), $CS_2$ is added to a slurry of 3-chlorobenzoylacetonitrile (1) and LiOH—$H_2O$ in DMF. The resulting mixture is treated with 1-bromopentan-2-one then to this mixture is then added bromo-Wang resin. The solvent is removed by filtration and the resin rinsed with solvent and dried under nitrogen to afford resin-bound compound 2.

In step (b), compound 2 is combined with THF and DMF-DMA and the resulting slurry heated at 60° C. for 18 hours. The solvent is removed by filtration and the resin washed with solvent then dried under nitrogen to afford resin-bound compound 3.

The pyrimidine ring is formed in step (c) by treating 3 with N-phenyl guanidine in THF at reflux for 24 hours. The solvent is removed by filtration and the resin washed several times with solvent. The resulting resin is again treated with N-phenyl guanidine in THF at reflux for another 24 hours. The solvent is again removed by filtration and the resin washed several times with solvent then dried under nitrogen to afford resin-bound compound 4.

The product V-1 is cleaved from the resin in step (d) by treating 4 with trifluoroacetic acid in dichloromethane and water for 3 hours at room temperature. The resin is filtered and washed with dichloromethane then treated with trifluoroacetic acid. The resulting mixture is allowed to sit for 14 hours at room temperature then filtered. The resin is washed with dichloromethane, the solvent concentrated, and the crude product purified by preparative HPLC to afford compound V-1. The details of the conditions used for producing these compounds are set forth in the Examples.

Reagents and conditions:
(a) i LiOH, DMF, $CS_2$, 0° C., 10 minutes;
   ii 1-bromo-butan-2-one, 0° C., 1 hour;
   iii Br-Wang resin, 0° C. → room temperature, 12 hours;
(b) DMF—DMA, THF, 60° C., 18 hours;
(c) N-phenyl guanidine, THF, reflux, 24 hours;
(d) TFA, $CH_2Cl_2$, water, room temperature, 14 hours.

Reagents and conditions:
(a) i ethylcyanoacetate, $MgCl_2$, $CH_3CN$, 0° C., 30 minutes;
   ii cyclohexanecarbonylchloride;
(b) DMSO/water, 120° C., 2 hours;
(c) i $CS_2$, $K_2CO_3$, DMF;
   ii chloroacetone;
   iii MeI.

Scheme V above shows a method for preparing the intermediate compound 5 which may be used to prepare compounds of formulae IIa, IIIa, IVa, V, and VI wherein $R^3$ is a cyclohexyl ring. Intermediate compound 5 may be readily transformed to compounds of formulae IIa, IIIa, IVa, V, and VI by the methods shown in Schemes I–IV above.

In step (a), a solution of ethyl cyanoacetate (2) in acetonitrile is treated with $MgCl_2$ and $Et_3N$ at 0° C., and the resulting suspension stirred at 0° C. for 30 minutes. To this suspension is added cyclohexanecarbonyl chloride (1) and the reaction mixture stirred at 0° C. Aqueous workup affords 3. A solution of compound 3 in $DMSO/H_2O$ is heated then aqueous work-up affords compound 4.

In step (c), compound 4 may be used to prepare thiophene compound 5 by using the method described in step (a) of Scheme II above.

Scheme VI

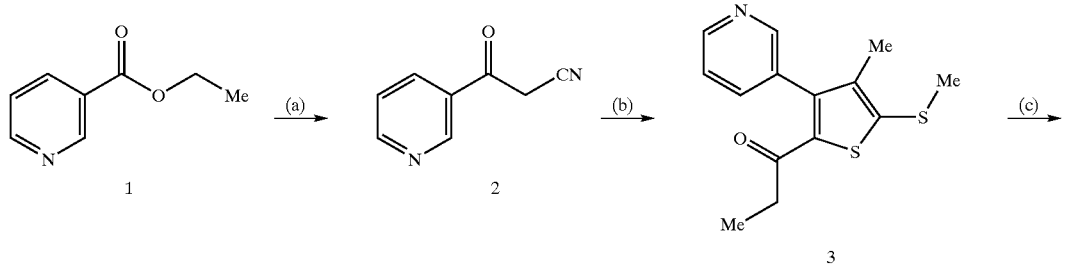

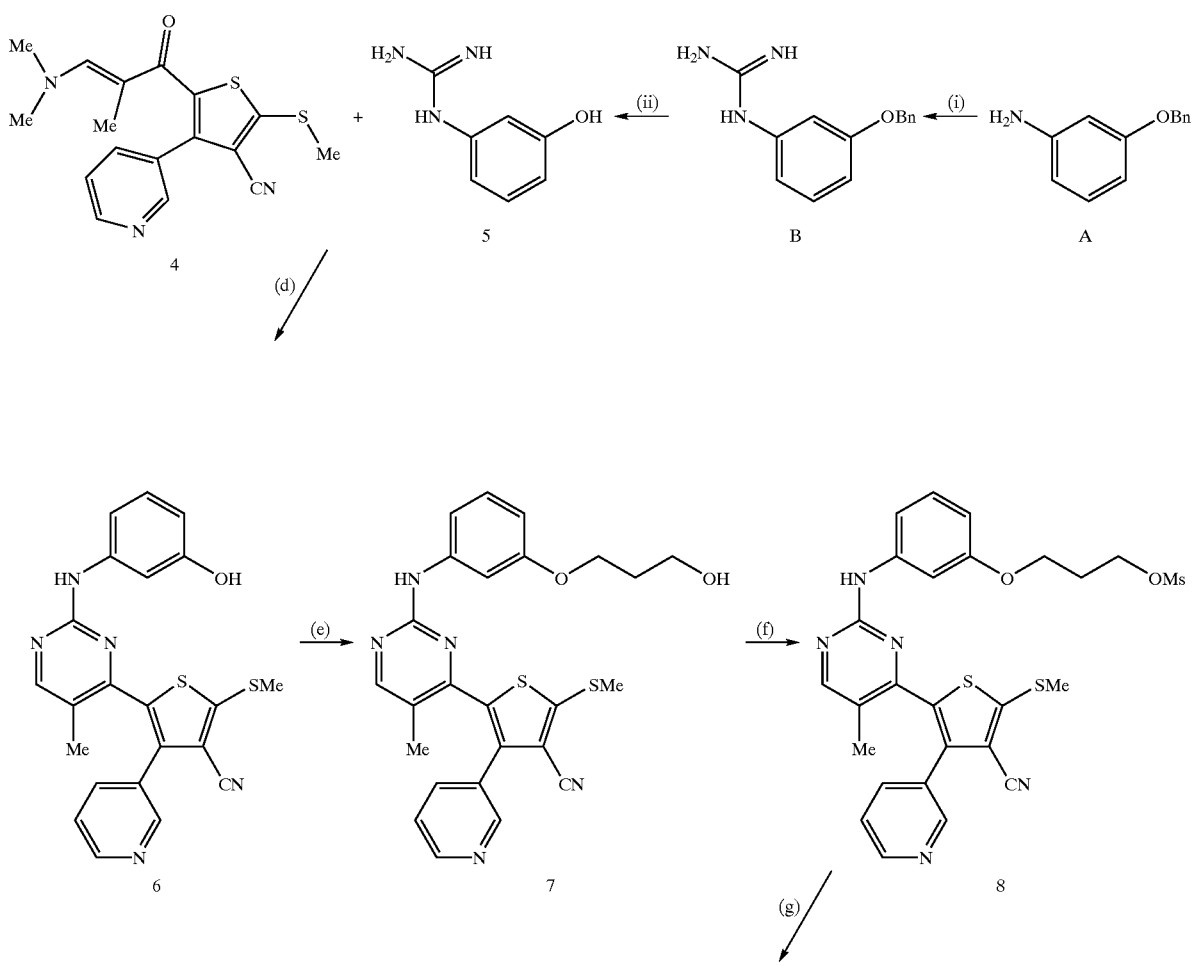

-continued

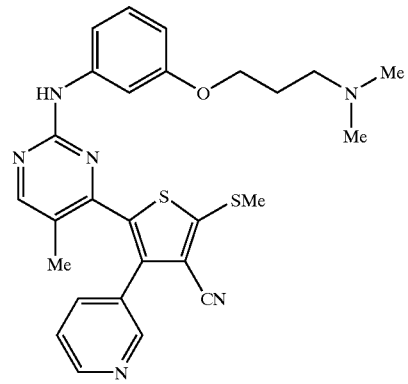

VI-18

Reagents and conditions:
(a) NaH, CH₃CN, toluene, reflux;
(b) i CS₂, K₂CO₃, DMF;
   ii 1-bromobutan-2-one;
   iii MeI;
(c) DMF—DMA, CH₃CN, reflux, 18 hours;
(d) N-(3-hydroxyphenyl)-guanidine, CH₃CN, reflux;
(e) 3-bromopropan-1-ol, K₂CO₃, DMF;
(f) MsCl, Et₃N, CH₂Cl₂, ambient temperature;
(g) Et₃N, dimethylamine, CH₂Cl₂, ambient temperature;
   (i) NH₂CN, HCl/dioxane, reflux;
   (ii) H₂, Pd/C.

Using the preparation of compound VI-18 as an example, Scheme VI above shows a method for preparing compounds of formula VI where $R^3$ is pyridin-3-yl and Z is a $C_{1-4}$ alkylidene chain wherein one methylene unit of Z is replaced by oxygen.

In step (a), a solution of ethyl nicotinate in toluene is treated with NaH and the resulting suspension heated at 90° C. while adding acetonitrile. After heating the reaction overnight, the reaction mixture is allowed to cool and the resulting solids collected by filtration.

Steps (b), (c), and (d) may be performed in a manner substantially similar to those described in step (a) of Scheme II, step (b) of Scheme IV, and step (c) of Schemes I and II. The resulting compound 6 may be used to prepare a variety of compounds of formula VI by using methods known in the art. Compound VI-18 was prepared, via steps (e) through (g), from compound 6 by alkylating the phenol with 3-bromopropanol at step (e). One of skill in the art would recognize that the compound 6 phenol group may be readily derivatized in a number of ways to form other compounds of formula VI. In step (f), the propanol —OH is treated with MsCl to form the mesylate which is displaced with dimethyl amine at step (g) to form compound VI-18. One of skill in the art would recognize that other leaving groups may be utilized to allow for further derivatization of the —OH group and that this leaving group may be displaced with a variety of amines to form other compounds of formula VI. The details of the conditions used to prepared the compounds of Scheme VI are set forth in the Examples.

Scheme VII

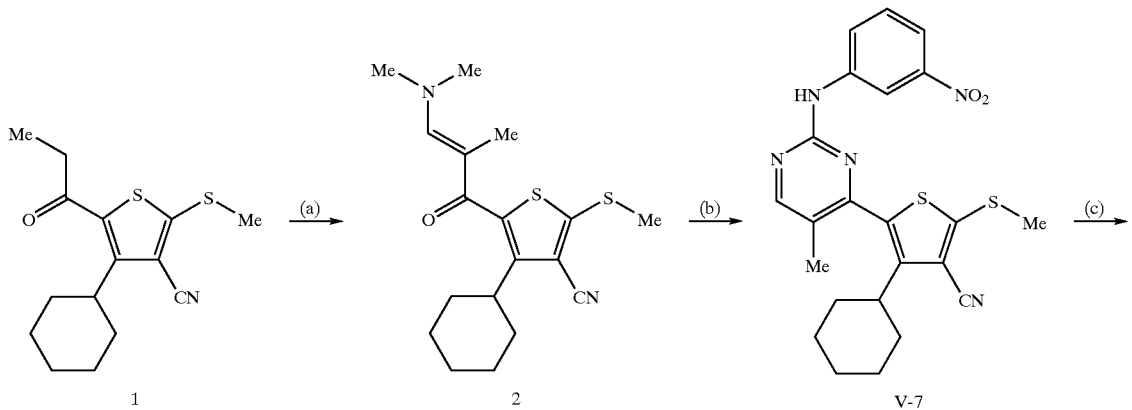

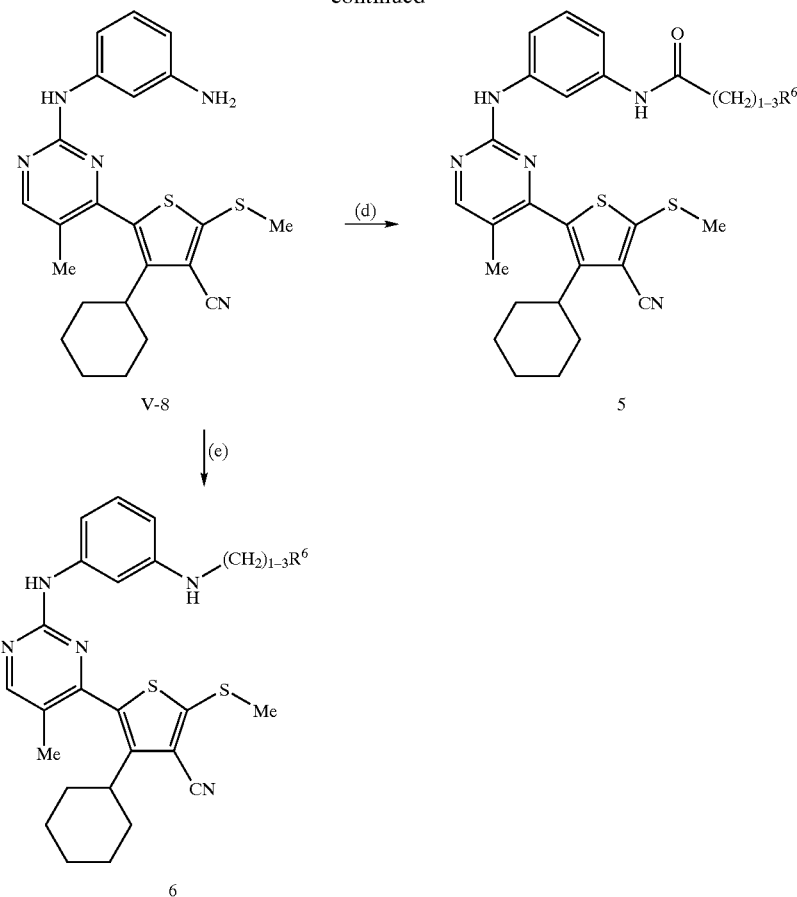

Reagents and conditions:
(a) DMF—DMA, toluene, reflux;
(b) 3-nitrophenylguanidine, DMF;
(c) H$_2$, 10% Pd/C, methanol;
(d) R$^6$—Z—COOH, EDC, HOBt, DIPEA, CH$_2$Cl$_2$;
(e) R$^6$—Z—Br, NaOtBu, THF.

Scheme VII above shows a general method for preparing compounds of formula VI where Z is a C$_{1-4}$ alkylidene chain wherein one methylene unit of Z is replaced by NH or NHCO. Compound 1 may be prepared according to the general methods described above. Compound V-7 may be prepared by steps (a) and (b) according to the methods described above. In step (c), the nitro group is hydrogenated in the presence of palladium on carbon to form the amino compound V-8. Compound V-8 may be used to prepare a variety of compounds of formula VI. For example, compound V-8 may be coupled with a carboxylic acid in order to form amide compounds 5. Alternatively, compound V-8 may be alkylated to form compounds 6. One of skill in the art would recognize that compound V-8 may be treated with a variety of reagents to form other compounds of formula VI.

According to another embodiment, the invention provides a method of inhibiting JNK, Src, or Lck kinase activity in a biological sample. This method comprises the step of contacting said biological sample with a compound of formula I. According to a preferred embodiment, the invention relates to a method of inhibiting JNK, Src, or Lck kinase activity in a biological sample comprising the step of contacting said biological sample with a compound of formula IIa, IIb, V, or VI. A more preferred embodiment relates to contacting said biological sample with a compound of formula IIa or VI.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of JNK, Src, or Lck kinase activity in a biological sample is useful for a variety of purposes which are known to one of skill in the art. Examples of such purposes include, but are not limited to, blood transfusion, organ-transplantation, biological specimen storage, and biological assays.

Compounds of formula I or salts thereof may be formulated into compositions. In a preferred embodiment, the composition is a pharmaceutically acceptable composition. In one embodiment, the composition comprises an amount of compound effective to inhibit a protein kinase, particularly JNK, Src, or Lck, in a biological sample or in a patient. In another embodiment, compounds of this invention and pharmaceutical compositions thereof, which comprise an amount of the compound effective to treat or prevent an JNK, Src, or Lck-mediated condition and a pharmaceutically acceptable carrier, adjuvant, or vehicle, may be formulated for administration to a patient.

The amount effective to inhibit protein kinase, for example, JNK, Src, or Lck, is one that measurably inhibits the kinase activity where compared to the activity of the enzyme in the absence of an inhibitor. Any method may be used to determine inhibition.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, favoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to a preferred embodiment, the pharmaceutical compositions of this invention are orally administered.

According to another embodiment, the present invention relates to a pharmaceutically acceptable derivative of a compound of formula I. In a preferred embodiment, said pharmaceutically acceptable derivative is of a compound of formula IIa, V, or VI. More preferably, said pharmaceutically acceptable derivative is of a preferred compound of formula IIa, V, or VI.

In addition to the compounds of this invention, pharmaceutically acceptable derivatives of the compounds of this invention may also be employed in compositions to treat or prevent the above-identified diseases or disorders.

A "pharmaceutically acceptable derivative" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. The methods for preparing salts or esters of a compound of this invention are known to one of skill in the art. Particularly favored derivatives are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable derivatives of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+$ $(C_{1-4}$ $alkyl)_4$ salts. This invention also envisions the quaternization of any basic nitrogen-containing groups of the compounds disclosed herein. Water or oil-soluble or dispersible products may be obtained by such quaternization.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The dosage of compound will also depend upon which particular compound is in the composition The compounds of this invention are inhibitors of JNK, Src, or Lck kinase as determined by enzymatic assay. Accordingly, these compounds are useful for treating JNK-, Src-, or Lck-mediated diseases or conditions.

Another aspect of this invention relates to a method for treating a JNK-, Src-, or Lck-mediated disease in a patient, which method comprises administering to a patient in need thereof, a therapeutically effective amount of a compound of formula I, or a pharmaceutically acceptable composition comprising said compound. According to a preferred embodiment, the invention relates to administering a compound of formula IIa, IIb, IIIa, IIIb, IVa, IVb, V, or VI, or a pharmaceutically acceptable composition comprising said compound. A more preferred embodiment relates to administering a compound of formula IIa, V, or VI, or a pharmaceutically acceptable composition comprising said compound.

Yet another aspect of this invention relates to a method for lessening the severity of a JNK-, Src-, or Lck-mediated disease in a patient, which method comprises administering to a patient in need thereof, a therapeutically effective amount of a compound of formula I, or a pharmaceutically acceptable composition comprising said compound. According to a preferred embodiment, the invention relates to administering a compound of formula IIa, IIb, IIIa, IIIb, IVa, IVb, V, or VI, or a pharmaceutically acceptable composition comprising said compound. A more preferred embodiment relates to administering a compound of formula IIa, V, or VI, or a pharmaceutically acceptable composition comprising said compound.

The activity of the compounds of this invention as kinase inhibitors may be assayed in vitro, in vivo or in a cell line. In vitro assays include assays that determine inhibition of either the kinase activity or ATPase activity of activated enzyme, for example JNK, Lck, or Src. Alternate in vitro assays quantitate the ability of the inhibitor to bind to JNK, Lck, or Src and may be measured either by radiolabelling the inhibitor prior to binding, isolating the inhibitor/JNK, inhibitor/Lck, or inhibitor/Src complex and determining the amount of radiolabel bound, or by running a competition experiment where new compounds are incubated with JNK, Lck, or Src bound to known radioligands. One may use any type or isoform of JNK, Lck, or Src, depending upon which JNK, Lck, or Src type or isoform is to be inhibited. The details of the conditions used for the enzymatic assays are set forth in the Examples hereinbelow.

The term "JNK-mediated disease" or "condition", as used herein means any disease or other deleterious condition in which JNK is known to play a role. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders which may be treated or prevented by the compounds of this invention include solid tumors, ocular neovasculization, infantile haemangiomas. Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

"JNK-mediated disease" or "condition" also includes ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, JNK inhibitors of the present invention may be capable of inhibiting the expression of inducible pro-inflammatory proteins. Therefore, other "JNK-mediated diseases" or "conditions" which may be treated by the compounds of this invention include edema, analgesia, fever and pain, such as neuromuscular pain, headache, cancer pain, dental pain and arthritis pain.

The compounds of this invention are also useful as inhibitors of Src-family kinases, especially Src. For a general review of these kinases see Thomas and Brugge, *Annu. Rev. Cell Dev. Biol.* (1997) 13, 513; Lawrence and Niu, Pharmacol. Ther. (1998) 77, 81; Tatosyan and Mizenina, Biochemistry (Moscow) (2000) 65, 49. Accordingly, these compounds are useful for treating Src-mediated diseases or conditions.

The term "Src-mediated disease" or "condition" as used herein means any disease or other deleterious condition that is known to be affected by the activity of one or more Src-family kinases. Such diseases or conditions include hypercalcemia, restenosis, hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-Cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease.

The term "Lck-mediated disease" or "condition" as used herein means any disease or other deleterious condition that is known to be affected by the activity of Lck kinase. Such diseases or conditions include autoimmune diseases, allergies, rheumatoid arthritis, and leukemia.

A preferred embodiment relates to the method used to treat or prevent a JNK-mediated disease selected from inflammatory diseases, autoimmune diseases, destructive bone disorders, neurodegenerative diseases, allergies, reperfusion/ischemia in stroke, heart attacks, angiogenic disorders, organ hypoxia, vascular hyperplasia, cardiac hypertrophy, or thrombin-induced platelet aggregation.

Another preferred embodiment relates to the method used to treat or prevent a Src-mediated disease selected from hypercalcemia, osteoperosis, osteoarthritis, or sympomatic treatment of bone metastasis.

Another preferred embodiment relates to the method used to treat or prevent a Lck-mediated disease selected from autoimmune diseases, rheumatoid arthritis, and leukemia.

Depending upon the particular protein kinase-mediated condition to be treated or prevented, additional therapeutic agents, which are normally administered to treat or prevent that condition, may be administered together with the compounds of this invention. For example, in the treatment of cancer other chemotherapeutic or anti-proliferative agents may be combined with the compounds of this invention to treat cancer. These agents include, without limitation, adriamycin, dexamethasone, vincristine, cyclophosphamide, fluorouracil, topotecan, taxol, interferons, and platinum derivatives.

Other examples of agents the compounds of this invention may also be combined with include, without limitation, anti-diabetic agents including insulin or insulin analogues in injectable or inhalation form, glitazones, alpha glucosidase inhibitors, biguanides, insulin sensitizers, and sulfonyl ureaschemotherapeutic agents; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01–100 mg/kg body weight/day of a compound of formula I can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01–100 μg/kg body weight/day of the additional therapeutic agent can be administered.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Suitable coatings and the general preparation of coated implantable devices are described in U.S. Pat Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

Each of the aforementioned methods directed to the inhibition of JNK, Lck, or Src, or the treatment of a disease alleviated thereby, is preferably carried out with a preferred compound of formula I, IIa, V, or VI, as described above. More preferably, each of the aforementioned methods is carried out with a preferred compound of formula I, IIa, V, or VI, and most preferably with a compound of formula IIa, V, or VI.

In order that the invention described herein may be more fully understood, the following examples are set forth. It should be understood that these examples are for illustrative purposes only and are not to be construed as limiting this invention in any manner.

EXAMPLES

As used herein, the term "$R_t$(min)" refers to the HPLC retention time, in minutes, associated with the compound using the HPLC method specified. Unless otherwise indicated, the HPLC methods utilized to obtain the reported retention times are as follows:

Method-A:
  Column: YMC ODS-AQ, 30×100 mm
  Gradient: 10%→90% $CH_3CN$/water (0.2% TFA) over 5 minutes
  Flow rate: 1 mL/minute
Method-B:
  Column: YMC ODS-AQ, 30×100 mm
  Gradient: 10%→90% $CH_3CN$/water (0.01% TFA)
  Flow rate: 1 mL/minute
  Detection: 210, 220, 254, 280, and 300 nm.
Method-C:
  Column: Lightning, 2.1×50 mm
  Gradient: 100% water (0.1% TFA)→100% $CH_3CN$ (0.1% TFA)
  Flow rate: 0.8 mL/minute Example 1

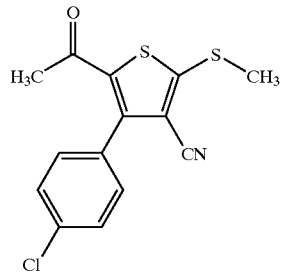

5-Acetyl-2-methylsulfanyl-4-(4-chloro-phenyl)-thiophene-3-carbonitrile 3-(4-chloro-phenyl)-3-oxo-propionitrile (5 mmol) was added to a suspension of $K_2CO_3$ (3 equivalents, 15 mmol) in DMF (4.5 mL) and allowed to stir at room temperature. After 10 minutes, $CS_2$ (1.25 equivalents, 7.5 mmol) was added in one portion and the resulting mixture stirred at room temperature for an additional 10 minutes then a solution of 1-chloro-propan-2-one (1.0 equivalent, 5 mmol) in DMF (5 mL) was added. After 1 hour, a solution of MeI (1.1 equivalents, 5.5 mmol) in DMF (2 mL) was added in a dropwise fashion then, after 30 minutes, the mixture was poured onto water and the resulting mixture was stirred vigorously for 12–16 hours to afford a suspension of the desired product. The crude product was isolated by filtration.

Example 2

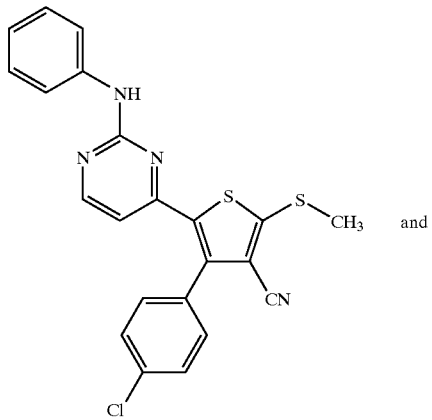

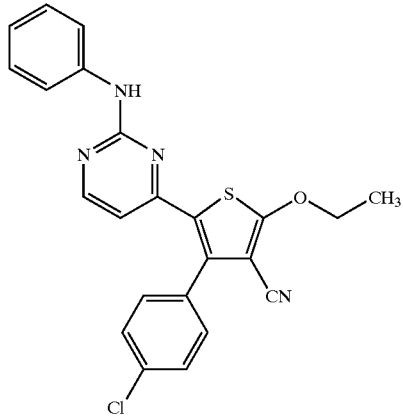

2-Methylsulfanyl-5-(2-phenylamino-pyrimidin-4-yl)-4-(4-chloro-phenyl)-thiophene-3-carbonitrile (IIa-10) and 2-Ethoxy-5-(2-phenylamino-pyrimidin-4-yl)-4-(4-chloro-phenyl)-thiophene-3-carbonitrile (IIa-11)

The crude 5-acetyl-2-methylsulfanyl-4-(4-chloro-phenyl)-thiophene-3-carbonitrile (1 mmol) was combined with Brederick's reagent (150 μL) in THF (10 mL) and allowed to stir at room temperature for 12–16 hours. The reaction mixture was concentrated and crude concentrate was dissolved in EtOH (10 mL). N-Phenyl guanidine (1.2 equivalent, 1.2 mmol) and sodium acetate (1 equivalent, 1 mmol) were added to the ethanolic solution and the resulting mixture was heated to 90° C. for 4 hours. The reaction mixture was concentrated then the residue was dissolved in ethyl acetate. The resulting organic solution was washed sequentially with water and brine. The organic layer was concentrated then the crude residue was purified by preparatory HPLC to afford compounds IIa-10 and IIa-11.

Example 3

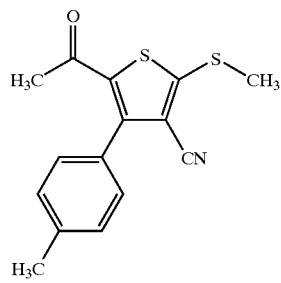

5-Acetyl-2-methylsulfanyl-4-(4-methyl-phenyl)-thiophene-3-carbonitrile 3-(4-Methyl-phenyl)-3-oxo-propionitrile (5 mmol) was added to a suspension of $K_2CO_3$ (3 equivalents, 15 mmol) in DMF (4.5 mL) and allowed to stir at room temperature. After 10 minutes, $CS_2$ (1.25 equivalents, 7.5 mmol) was added in one portion and the resulting mixture stirred at room temperature for an additional 10 minutes. A solution of 1-chloro-propan-2-one (1.0 equivalent, 5 mmol) in DMF (5 mL) was added. After 1 hour, a solution of MeI (1.1 equivalents, 5.5 mmol) in DMF (2 mL) was added in a dropwise fashion. After 30 minutes, the mixture was poured onto water and the resulting mixture was stirred vigorously for 12–16 hours to afford a suspension of the desired product. The crude product was isolated by filtration.

Example 4

2-Methylsulfanyl-5-(2-phenylamino-pyrimidin-4-yl)-4-p-tolyl-thiophene-3-carbonitrile (IIa-14) and 2-Ethoxy-5-(2-phenylamino-pyrimidin-4-yl)-4-p-tolyl-thiophene-3-carbonitrile (IIa-15)

The crude 5-acetyl-2-methylsulfanyl-4-(4-methyl-phenyl)-thiophene-3-carbonitrile (1 mmol) was combined with Brederick's reagent (150 µL) in THF (10 mL) and allowed to stir at room temperature for 12–16 hours. The reaction mixture was concentrated and crude concentrate was dissolved in EtOH (10 mL). N-Phenyl guanidine (1.2 equivalent, 1.2 mmol) and sodium acetate (1 equivalent, 1 mmol) were added to the ethanolic solution and the resulting mixture was heated to 90° C. for 4 hours. The reaction mixture was concentrated then the residue was dissolved in ethyl acetate. The resulting organic solution was washed sequentially with water and brine. The organic layer was concentrated then the crude residue was purified by preparative HPLC to afford compounds IIa-14 and IIa-15.

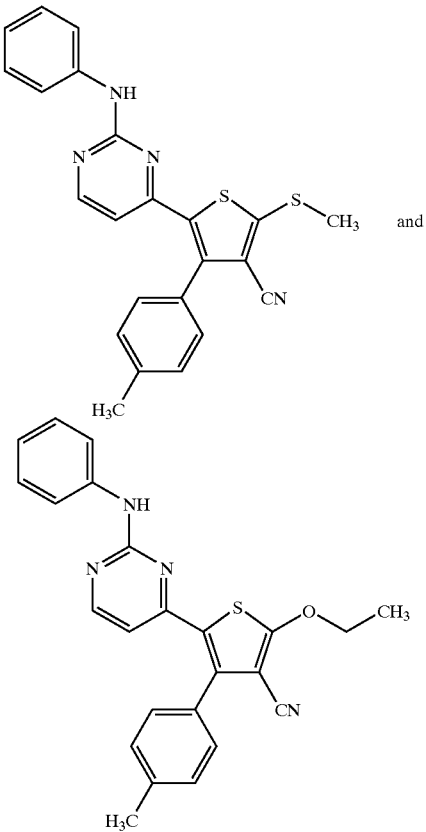

IIa-14 and

IIa-15

Example 5

IIa-37

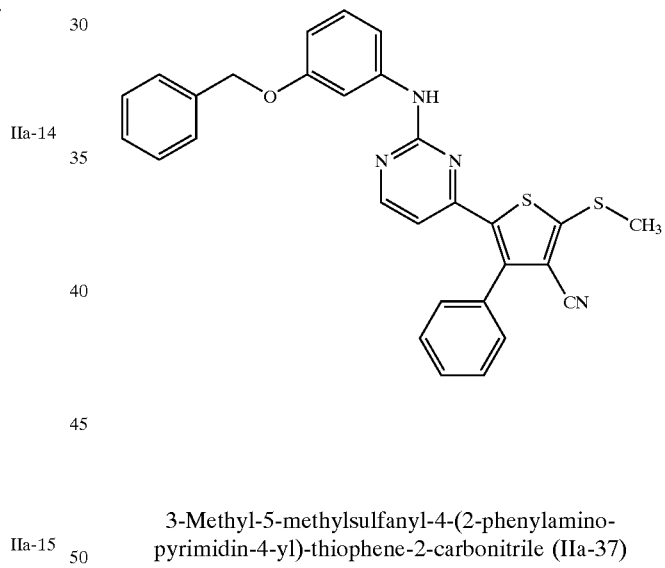

3-Methyl-5-methylsulfanyl-4-(2-phenylamino-pyrimidin-4-yl)-thiophene-2-carbonitrile (IIa-37)

4-(3-Dimethylamino-acryloyl)-3,4-dimethyl-5-methylsulfanyl-4,5-dihydro-thiophene-2-carbonitrile (0.2 mmol) was combined with N-phenyl-guanidine (0.2 mmol) in acetonitrile (0.25 mL) and the resulting mixture heated at reflux for 24 hours. The reaction mixture was diluted with methanol (3mL) and the resulting slurry filtered and the solid was washed with methanol (2 mL) then dried under nitrogen to afford IIa-37. M+H=507.1, HPLC: $R_t$=6.196 minutes, $^1$H NMR (500 Mz, DMSO) 9.77(s, 1H), 8.25(d, 1H, J=5.3 Hz), 7.69(s, 1H), 7.48(m, 2H), 7.48(m, 4H), 7.41(t, 2H, J=7.3 Hz), 7.34(t, 1H, J=7.2 Hz), 7.25(d, 1H, J=8.3 Hz), 7.21 (t, 1H, J=8.0 Hz), 6.67(d, 1H, J=6.7 Hz), 6.01(d, 1H, J=5.3 Hz), 5.11(s, 2H), 3.32(s, 3H, CH3), 2.68(s, 3H, CH3).

Example 6

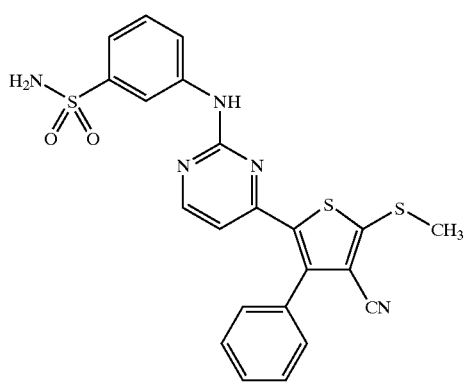

3-[4-(4-cyano-5-methylsulfanyl-3-phenyl-thiophen-2-yl)-pyrimidin-2-ylamino]-benzenesulfonamide (IIa-38)

M+H=480.1, HPLC $R_t$=5.018 minutes, $^1$H NMR (500 Mz, DMSO) 10.12(s, 1H), 8,64(s, 1H), 8.28(d, 1H, J=5.3 Hz), 7.69(d, 1H, J=7.7 Hz), 7.60–7.58(m, 3H), 7.51(d, 1H, J=7.7 Hz), 7.49–7.47(m, 4H), 7.32(br s, 1H), 7.00(br s, 1H), 6.06(d, 1H, J=5.3 Hz), 2.90(s, 3H).

Example 8

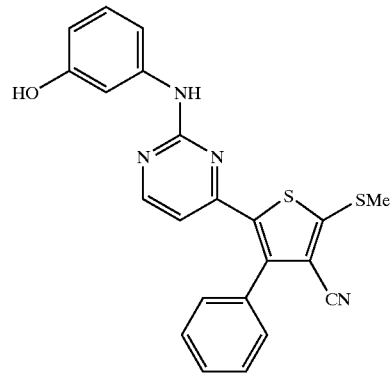

5-[2-(3-Hydroxy-phenylamino)-pyrimidin-4-yl]-2-methylsulfanyl-4-phenyl-thiophene-3-carbonitrile (IIa-40)

M+H=417.1, HPLC: $R_t$=4.682 minutes, $^1$NMR (500 Mz, DMSO) 9.62(s, 1H), 9.26(s, 1H), 8.22(d, 1H, J=5.3 Hz), 7.58(m, 3H), 7.48(m, 2H), 7.30(t, 1H, J=1.9 Hz), 7.16(d, 1H, J=8.1 Hz), 7.07(t, 1H, J=8.0 Hz), 6.40(dd, 1H, J=7.9, 2.2 Hz), 5.99(d, 1H, J=5.2 Hz), 2.84(s, 3H).

Example 7

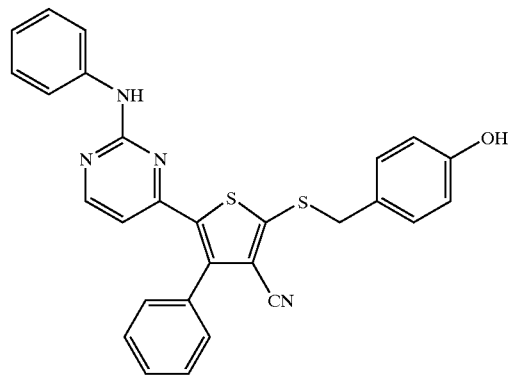

2-(4-Hydroxy-benzylsulfanyl)-4-phenyl-5-(2-phenylamino-pyrimidin-4-yl)-thiophene-3-carbonitrile (IIa-39)

M+H=493.2, HPLC: $R_t$=5.812 minutes, $^1$NMR (500 Mz, DMSO) 9.75(s, 1H), 8.24(d, 1H, J=5.2 Hz), 7.73(d, 2H, J=8.0 Hz), 7.57(m, 3H), 7.44(m, 2H), 7.34(t, 2H, J=7.9 Hz), 7.26(d, 2H, J=8.5 Hz), 7.01(t, 1H, 7.2 Hz), 6.74(d, 2H, J=8.5 Hz), 6.01(d, 1H, J=5.2 Hz), 4.43(s, 2H).

Example 9

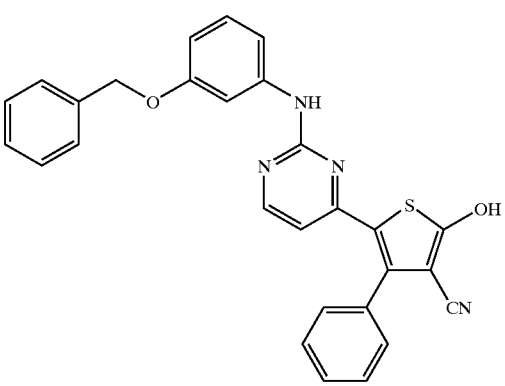

5-[2-(3-Benzyloxy-phenylamino)-pyrimidin-4-yl]-2-hydroxy-4-phenyl-thiophene-3-carbonitrile (IIa-42)

M+H=477.2, HPLC: Rt=4.530 minutes, $^1$NMR (500 Mz, DMSO) 10.13(s, 1H), 7.55(m, 4H), 7.48–7.38(m, 5H), 7.34 (t, 1H, J=7.2 Hz), 7.29(t, 1H, J=8.2 Hz), 7.12(d, 1H, J=7.8 Hz), 6.79(dd, 1H, J=8.2, 2.1 Hz), 5.63(d, 1H, J=7.1 Hz), 5.18(s, 2H).

Example 10

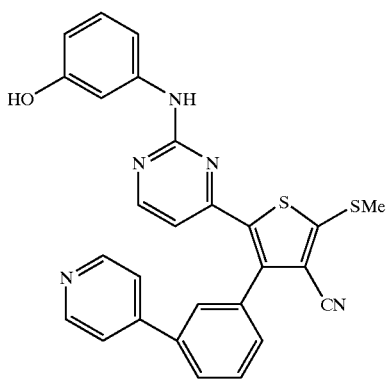

IIa-105

5-[2-(3-Hydroxy-phenylamino)-pyrimidin-4-yl]-2-methylsulfanyl-4-(3-pyridin-4-yl-phenyl)-thiophene-3-carbonitrile (IIa-105)

To 2 ml DME in a 10 ml tube was added I (50 mg, 0.10 mmol), 4-(4,4,5,5-tetramethyl-[1,3,2]dioxaborolan-2-yl)pyridine (25 mg, 0.12 mmol) and tetrakis(triphenylphosphine)palladium(0) (11.5 mg, 0.01 mmol). The mixture was stirred at ambient temperature under nitrogen for 30 minutes then 0.3 ml saturated $NaHCO_3$ aqueous solution was added to the reaction mixture and the reaction was stirred at 45° C. in a sealed tube for 6 hours. The reaction was cooled to ambient temperature then was diluted with 2 ml water. The mixture was extracted with ethyl acetate (5 ml×3) and combined organic layers were dried over $Na_2SO_4$. The solvent was removed under reduced pressure and the residue purified by chromatography using ethyl acetate and hexane (1:1) on silica gel to afford 23 mg of the desired compounds in 47% yield. $^1$NMR δ (Acetone-d6): 8.96 (s, 1H), 8.92(d, 2H), 8.20(m, 5H), 7.88(dd, 1H), 7.80(dd, 1H), 7.53(d, 1H), 7.32(d, 1H), 7.22(dd, 1H), 6.56(d, 1H), 6.26(d, 1H), 2.92(s, 3H)

Example 11

We have prepared other compounds of formula IIa by methods substantially similar to those described in the above Examples 1–10 and those illustrated in Scheme I. The characterization data for these compounds is summarized in Table 9 below and includes LC/MS (observed) and $^1$HNMR data. "Y" designates $^1$HNMR data was obtained and found to be consistant with the assigned structure. Compound numbers correspond to the compound numbers listed in Table 1.

TABLE 9

Characterization Data for Selected Compounds of Formula IIa

| Compound No | M + 1 (obs) | $R_t$ | Method | $^1$H NMR |
|---|---|---|---|---|
| IIa-1 | 368.04 | — | — | Y |
| IIa-2 | 358.01 | — | — | Y |
| IIa-3 | 392.03 | — | — | Y |
| IIa-4 | 338.06 | — | — | — |
| IIa-5 | 358.01 | — | — | Y |
| IIa-6 | 354.06 | — | — | — |
| IIa-7 | 451.00 | — | — | — |
| IIa-8 | 417.00 | — | — | — |
| IIa-9 | 413.01 | — | — | — |
| IIa-10 | — | 4.935 | B | Y |
| IIa-11 | — | 4.732 | B | Y |
| IIa-12 | 468.00 | 4.969 | B | Y |
| IIa-13 | 466.00 | 4.784 | B | Y |
| IIa-14 | 414.01 | 4.888 | B | Y |
| IIa-15 | 412.01 | 4.627 | B | Y |
| IIa-16 | 324.05 | — | — | Y |
| IIa-37 | 507.1 | 6.193 | B | Y |
| IIa-38 | 479.9 | 5.018 | B | Y |
| IIa-39 | 493.0 | 5.812 | B | Y |
| IIa-40 | 447.1 | 4.682 | B | Y |
| IIa-42 | 477.2 | 4.530 | B | Y |
| IIa-43 | 481.3 | 5.10 | A | Y |
| IIa-44 | 586.2 | 4.18 | A | Y |
| IIa-45 | 513.0 | 5.82 | A | Y |
| IIa-46 | 407.0 | 6.28 | A | Y |
| IIa-47 | 479.0 | 5.51 | A | Y |
| IIa-48 | 403.1 | 4.42 | A | Y |
| IIa-49 | 476 | 2.62 | A | Y |
| IIa-50 | 446.08 | 2.99 | A | Y |

Example 12

4-Acetyl-3-methyl-5-methylsulfanyl-thiophene-2-carbonitrile

To a slurry of 2,4-pentanedione (20 mmol) and $K_2CO_3$ (3 equivalents, 60 mmol) in DMF (10 mL) was added $CS_2$ (1.2 equivalents, 24 mmol) and the resulting mixture stirred for 10 minutes. The mixture was cooled to 0° C. then chloroacetonitrile (1.0 equivalent, 20 mmol) was added and the reaction stirred 1 hour then warmed to room temperature and stirred for an additional 2 hours. The reaction mixture was again cooled to 0° C. and methyl iodide (1.05 equivalents, 22 mmol) was added slowly. The resulting mixture was warmed to room temperature. After 12 hours, water was added and the resulting suspension was stirred overnight. The desired product was isolated by filtration after washing with water.

Example 13

4-(3-Dimethylamino-acryloyl)-3-methyl-5-methylsulfanyl-thiophene-2-carbonitrile To a solution of 4-acetyl-3-methyl-5-methylsulfanyl-thiophene-2-carbonitrile (10 mmol) in acetonitrile (5 mL)

Example 14

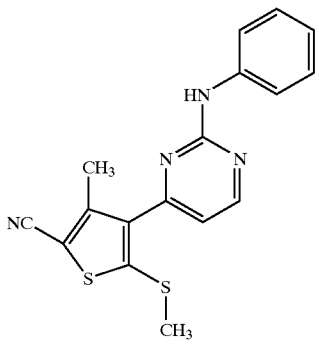

IIb-7

3-Methyl-5-methylsulfanyl-4-(2-phenylamino-pyrimidin-4-yl)-thiophene-2-carbonitrile (IIb-7)

To a solution of 4-(3-dimethylamino-acryloyl)-3-methyl-5-methylsulfanyl-thiophene-2-carbonitrile (0.2 mmol) in acetonitrile (0.25 mL) was added N-phenyl guanidine (1 equivalent, 0.2 mmol) and the reaction heated at reflux for 24 hours. The resulting mixture was cooled to room temperature then diluted with methanol (3 mL). The resulting slurry was filterred washed with methanol to afford IIb-7.

Example 15

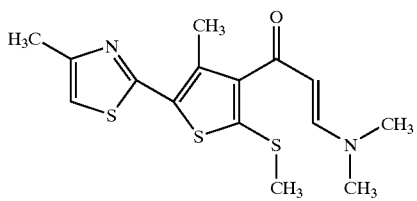

3-Dimethylamino-1-[4-methyl-2-methylsulfanyl-5-(4-methyl-thiazol-2-yl)-thiophen-3-yl]-propenone To a solution of 1-[4-methyl-2-methylsulfanyl-5-(4-methyl-thiazole-2-yl)-thiophen-3-yl]-ethanone (10 mmol, Maybridge Chemicals) in acetonitrile (5 mL) was added DMF-DMA (2 mL) and the resulting mixture heated at reflux for 18 hours. The reaction was concentrated and the residue triturated with diethyl ether (20 mL). The suspension was filtered and washed with ether to afford the desired product as a yellow solid.

Example 16

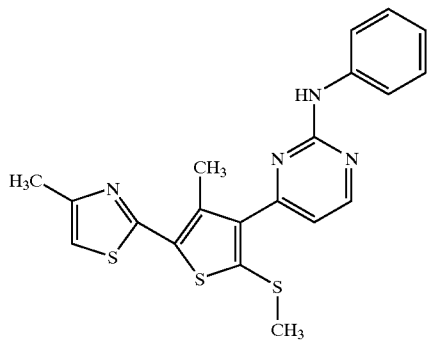

IIb-1

{4-[4-methyl-2-methylsulfanyl-5-(4-methyl-thiazol-2-yl)-thiophen-3-yl]-pyrimidin-2-yl}-phenylamine (IIb-1)

To a solution of 3-dimethylamino-1-[4-methyl-2-methylsulfanyl-5-(4-methyl-thiazol-2-yl)-thiophen-3-yl]-propenone (0.2 mmol) in acetonitrile (0.25 mL) was added N-phenyl guanidine (1 equivalent, 0.2 mmol) and the reaction heated at reflux for 24 hours. The resulting mixture was cooled to room temperature then diluted with methanol (3 mL). The resulting slurry was filterred washed with methanol to afford IIb-1.

Example 17

We have prepared other compounds of formula IIb by methods substantially similar to those described in the above Examples 12–16 and those illustrated in Schemes II and III. The characterization data for these compounds is summarized in Table 10 below and includes ah LC/MS (observed) data. Compound numbers correspond to the compound numbers listed in Table 2.

TABLE 10

Characterization Data for Selected Compounds of Formula IIb

| Compound No | M + 1 (obs) | Compound No | M + 1 (obs) |
|---|---|---|---|
| IIb-1 | 410.9 | IIb-7 | 339.1 |
| IIb-2 | 428.9 | IIb-8 | 357.2 |
| IIb-3 | 445.9 | IIb-9 | 374.1 |
| IIb-4 | 444.9 | IIb-10 | 373.1 |
| IIb-5 | 440.9 | IIb-11 | 369.2 |
| IIb-6 | 516.9 | IIb-12 | 445.1 |

Example 18

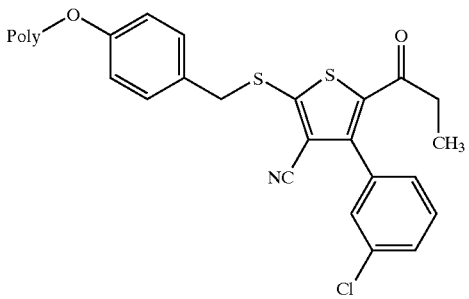

Resin-bound 4-(3-chloro-phenyl)-2-(4-resin-oxy-benzylsulfanyl)-5-propionyl-thiophene-3-carbonitrile To a stirring slurry of 3-chlorobenzoylacetonitrile (Maybridge, 1 equivalent, 15 mmol) and LiOH-H$_2$O (3 equivalents, 45 mmol) in DMF (30 mL) was added CS$_2$ (1.2 equivalents, 18 mmol) and the resulting mixture stirred for 10 minutes at 0° C. 1-bromo-2-butanone (1.0 equivalent, 15 mmol) was added to the mixture at 0~5° C. and stirred for one hour. Bromo-Wang resin (Novabiochem, 3 g, 3.9 mmol, 1.3 mmol/g loading) was then added at 0~5° C. and the resulting mixture was stirred at room temperature for 12 hours. The solvent was removed by filtration and the resin rinsed with DMF (30 mL,×3), THF (30 mL,×3), water (30 mL×3), DMF (30 mL×3), DCM (30 mL×3) and diethyl ether (30 mL×3) then dried under nitrogen to afford the title compound.

Example 19

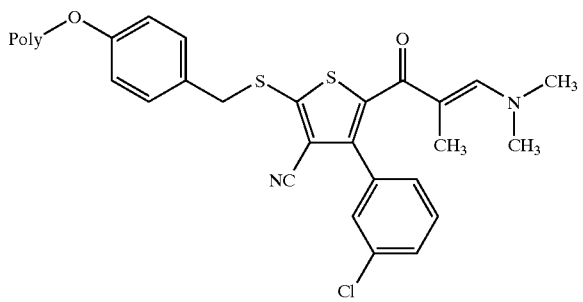

Resin bound 4-(3-chloro-phenyl)-5-(3-dimethylamino-2-methyl-acryloyl)-2-(4-hydroxy-benzylsulfanyl)-thiophene-3-carbonitrile The above resin bound compound formed in Example 18 above was slurried in dry THF (20 mL) and treated with DMF-DMA (2 mL) then the resulting mixture was heated at 60° C. for 18 hours. The solvent was removed by filtration and the resin was rinsed with THF (30 mL×5), DCM (30 mL×3), and diethyl ether (30 mL×3) then dried under nitrogen to afford the title compound.

Example 20

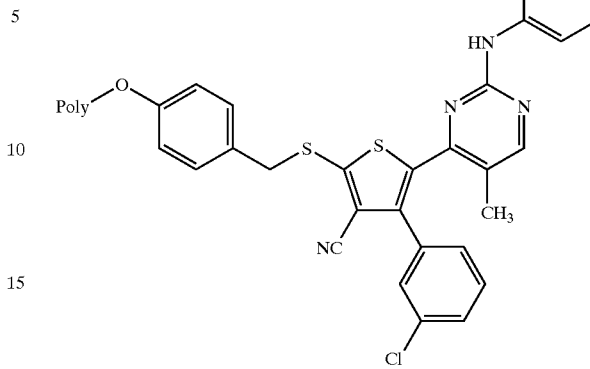

Resin bound 4-(3-chloro-phenyl)-2-(4-resin bounded hydroxy-benzylsulfanyl)-5-(5-methyl-2-phenylamino-pyrimidin-4-yl)-thiophene-3-carbonitrile The resin bound compound formed in Example 19 above (1 g) and N-phenyl-guanidine (4 mmol) were combined in dry THF (10 mL). The resulting mixture was heated to reflux for 24 hours then the solvent was removed by filtration and the resin rinsed with THF (30 mL×5), DMF (30mL×3), DCM (30 mL×3), and diethyl ether (30 mL×3) then dried under nitrogen. The resin was treated once again with N-phenyl-guanidine (4 mmol) in dry THF (10 mL) for 24 hours. Solvent was again removed by filtration and the resin rinsed with THF (30 mL×5), DMF (30 mL×3), DCM (30 mL×3), and diethyl ether (30 mL×3) then dried under nitrogen to afford the title compound.

Example 21

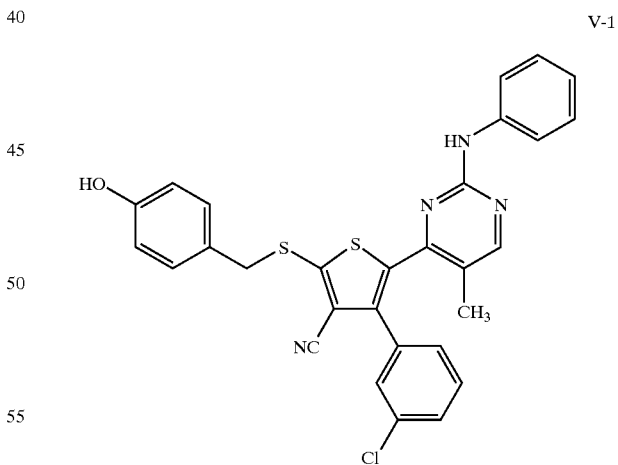

V-1

4-(3-chloro-phenyl)-2-(4-hydroxy-benzylsulfanyl)-5-(5-methyl-2-phenylamino-pyrimidin-4-yl)-thiophene-3-carbonitrile (V-1)

The resin bound compound formed at Example 20 above (100 mg, 0.1 mmol) was slurried in DCM (1 mL) and treated with TFA (1 mL) and one drop of water for 3 hours. The resin was filtered and washed with DCM (2 mL×3). The resin was then treated with 50% TFA in DCM-water (1 mL:1 mL: 0.02 mL). The mixture was set aside for 14 hours then filtered. The resin was washed with dichloromethane (2 mL×3), the combined organic layers were concentrated, and the crude product was purified by preparative HPLC [YMC ODS-AQ column, gradient 10%→90% B (solvent A: 0.01% TFA in water; solvent B: 0.01% TFA in $CH_3CN$) over 6.5 minutes at 1 mL/min] to afford compound V-1 (10 mg). [M+H]=541.1.

Example 22

We have prepared other compounds of formula V by methods substantially similar to those described in the above Examples 18–21 and those illustrated in Scheme IV. The characterization data for these compounds is summarized in Table 11 below and includes HPLC, LC/MS (observed) and $^1$NMR data.

$^1$H NMR data is summarized in Table 11 below wherein "Y" designates $^1$H NMR data is available and was found to be consistant with structure.

Compound numbers correspond to the compound numbers listed in Table 7.

TABLE 11

Characterization Data for Selected Compounds of Formula V

| Compound No | M + 1 (obs) | $R_t$(min) | Method | $^1$H NMR |
|---|---|---|---|---|
| V-4 | 521.2 | 6.063 | B | Y |
| V-5 | 494.1 | 5.114 | B | Y |
| V-6 | 431.1 | 4.97 | B | Y |
| V-7 | 460.1 | 5.930 | B | Y |
| V-8 | 430.1 | 3.987 | B | — |
| V-9 | 489.1 | 4.711 | C | Y |
| V-10 | 499.0 | 4.024 | C | Y |
| V-11 | 541.1 | — | — | — |
| V-13 | 445.1 | 5.197 | B | — |
| V-14 | 430.1 | 4.115 | B | — |
| V-15 | 522.2 | 6.75 | B | Y |
| V-16 | 416.1 | 3.67 | A | Y |
| V-17 | 446.1 | 3.69 | A | Y |
| V-18 | 476.1 | 3.73 | A | Y |
| V-19 | 494.0 | 4.18 | A | Y |
| V-20 | 547.2 | 2.51 | A | Y |
| V-21 | 474.1 | 3.74 | A | Y |
| V-22 | 451.0 | 3.44 | A | Y |
| V-23 | 430.1 | 3.61 | A | Y |
| V-24 | 432.1 | 5.47 | B | Y |
| V-25 | 406.1 | 4.893 | B | — |
| V-26 | 421.1 | 4.749 | B | Y |
| V-27 | 511.0 | 6.608 | B | Y |
| V-28 | 450.0 | 5.923 | B | — |

Example 23

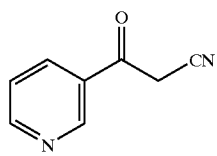

3-oxo-3-pyridin-3-yl-propionitrile

To a solution of ethyl nicotinate (30.24 g, 0.20 mol) in toluene (anhydrous, 200 mL) was added NaH (18.64 g, 0.47 mol, 60% in mineral oil). The resulting suspension was heated at 90° C. and acetonitrile (anhydrous, 24.74 ml, 0.47 mol) was added into this suspension via syringe under nitrogen and the reaction was heated at 90° C. overnight. The reaction mixture was cooled to ambient temperature and the resulting solid material was collected by filtration. The crude product was dried in vacuo and used directly in the next step. For analytical purposes, the solid was dissolved in water. The pH was adjusted to 5 by aqueous HCl and the solution extracted with DCM. The organic layer was dried over $Na_2SO_4$ and the solvent was removed in vacuo to afford a sample of the product for characterization. $^1$H NMR ($CDCl_3$): δ9.2(s, 1H), 8.8(d, 1H), 8.2(d, 1H), 7.5(dd, 1H), 4.1 (s, 2H)

Example 24

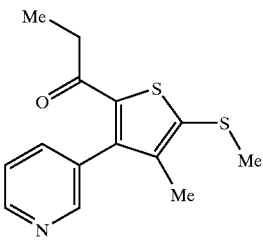

1-(4-Methyl-5-methylsulfanyl-3-pyridin-3-yl-thiophen-2-yl)-propan-1-one

To a solution of 3-oxo-3-pyridin-3-yl-propionitrile (11.9 mmol) in DMF (100 mL) was added $CS_2$ (0.90 ml, 15.0 mmol) at 0° C. The reaction was stirred at 0° C. for 45 minutes under nitrogen then 1-bromo-butan-2-one (1.79 g, 11.8 mmol) was added via a syringe at 0° C. The reaction was stirred for another 30 minutes then methyl iodide (1.69 g, 11.8 mmol) was added via syringe at 0° C. The resulting mixture was stirred for another 30 minutes then warmed to ambient temperature and poured into saturated aqueous $NH_4Cl$ solution (300 mL). The solution was extracted with ethyl acetate (200 mL×3) and the combined organic layers were dried over $Na_2SO_4$ then concentrated in vacuo. Purification by chromatography (Silica Gel, 3:1 hexanes:ethyl acetate) afforded 1.05 g desired product. $^1$H NMR (CDCl3): δ8.8(d, 1H), 8.6 (s, 1H), 7.8 (d, 1H), 7.5 (dd, 1H), 2.8 (s, 3H), 2.3 (q, 2H), 1.0 (t, 3H).

Example 25

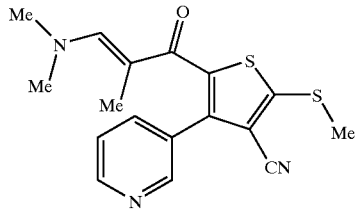

5-(3-Dimethylamino-2-methyl-acryloyl)-2-methylsulfanyl-4-pyridin-3-yl-thiophene-3-carbonitrile A solution of 1-(4-methyl-5-methylsulfanyl-3-pyridin-3-yl-thiophen-2-yl)-propan-1-one (1.0 g, 3.48 mmol) in DMF-DMA (10 mL) in a 50 ml sealed tube was stirred at 90° C. overnight. The reaction was cooled to ambient temperature and the excess dimethylformamide dimethyl acetal was removed in vacuo. The purification of the crude by chromatography, eluting with ethyl acetate, afforded 964 mg (81%) desired product. $^1$H NMR ($CDCl_3$): δ8.6(m, 2H), 7.7 (d, 1H), 7.3 (d, 1H), 6.7 (s, 1H), 2.8 (s, 6H), 2.7 (s, 3H), 1.9 (s, 3H).

Example 26

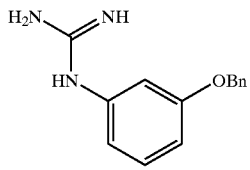

N-(3-Benzyloxy-phenyl)guanidine

To a suspension of 3-benzyloxyphenylamine (20.0 g, 100.35 mmol) in 1,4-dioxane (150 mL) was added cyanamide (7.39 g, 175.95 mmol followed by 4M HCl in 1,4-dioxane (44 ml, 176.00 mmol).

The resulting suspension was heated at 80° C. overnight then cooled to ambient temperature and 6N NaOH (35 ml, 210.00 mmol) was added. The volume of solution was reduced to 50 ml in vacuo and the resulting precipitate was collected by filtration. The solid product was dried under vacuum overnight to afford 23.8 g in 98.4% yield. $^1$H NMR (MeOH-d4) δ6.4–7.5 (m, 9H), 5.1 (s, 2H).

Example 27

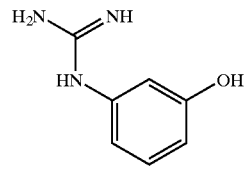

N-(3-Hydroxy-phenyl)-guanidine (5)

To a solution of N-(3-benzyloxy-phenyl)guanidine (5.0 g, 20.6 mmol) in EtOH (150 mL) was added palladium on carbon (10%, wet, 50% water, 0.5 g)). The mixture was stirred under hydrogen atmosphere overnight. The reaction was filtered through a plug of celite and the filtrate concentrated in vacuo. with toluene azeotroping to affored the desired material (2.83 g, 91%). $^1$H NMR (MeOH-d4) δ6.4–7 (m, 4H)

Example 28

V-24

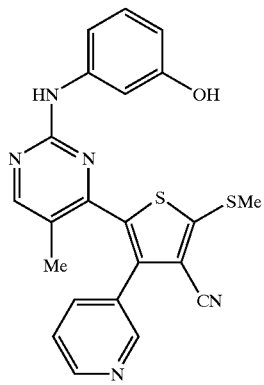

5-[5-(3-Hydroxy-phenylamino)-2-methyl-phenyl]-2-methylsulfanyl-4-pyridin-3-yl-thiophene-3-carbonitrile (V-24)

To a solution of 5-(3-dimethylamino-2-methyl-acryloyl)-2-methylsulfanyl-4-pyridin-3-yl-thiophene-3-carbonitrile (45 mg, 0.13 mmol) in CH$_3$CN (anhydrous, 2 mL) was added N-(3-hydroxy-phenyl)-guanidine (38 mg, 0.16 mmol). The reaction was stirred at 90° C. in a sealed tube overnight then cooled to ambient temperature and the solvent removed in vacuo. The crude product was purified by chromatography (Silica Gel, 2:1 hexanes:ethyl acetate) to afford compound V-24 (51 mg, 75%). $^1$H NMR (CDCl$_3$): δ8.6(d, 1H), 8.5 (s, 1H), 8.2 (s, 1H), 7.8 (d, 1H),7.6 (s, 1H), 7.5–7.1 (m, 8H), 7.0 (d, 1H), 6.7 (d, 1H), 5.1 (s, 2H), 2.6 (s, 3H), 1.5 (s, 3H).

Example 29

VI-29

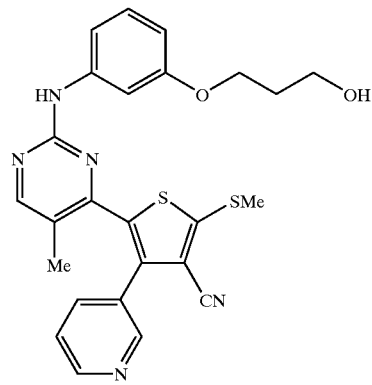

5-{5-[3-(3-Hydroxy-propoxy)-phenylamino]-2-methyl-phenyl}-2-methylsulfanyl-4-pyridin-3-yl-thiophene-3-carbonitrile (VI-29)

To a solution of 5-[5-(3-hydroxy-phenylamino)-2-methyl-phenyl]-2-methylsulfanyl-4-pyridin-3-yl-thiophene-3-carbonitrile (330 mg, 0.77 mmol) in DMF (anhydrous, 5 mL) was added 3-bromo-propan-1-ol (214 mL, 1.54 mmol). The reaction was stirred at 70° C. in the presence of excess K$_2$CO$_3$ overnight then cooled to ambient temperature and partitioned between water and DCM. The mixture was extracted with DCM (30 ml×3) and the combined organic layers were dried over Na$_2$SO$_4$ and concentrated in vacuo. Purification by chromatography (2% MeOH-DCM) afforded desired product (370 mg, 99%). $^1$H NMR (CDCl3): δ8.6(d, 1H), 8.5 (d, 1H), 8.1 (s, 1H), 7.7 (d, 1H), 7.4 (s, 1H), 7.3–7.2 (m, 3H), 7.0 (d, 1H), 6.6 (d, 1H), 4.1 (t, 2H), 3.9 (t, 2H), 2.7 (s, 3H), 2.0 (m, 2H), 1.5 (s, 3H)

Example 30

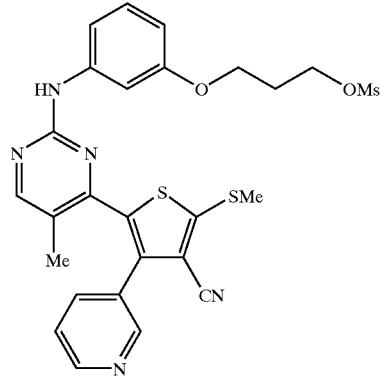

Methanesulfonic acid 3-{3-[3-(4-cyano-5-methylsulfanyl-3-pyridin-3-yl-thiophene-2-yl)-4-methyl-phenylamino]-phenoxyl}-propyl ester To a solution of 5-{5-[3-(3-hydroxy-propoxy)-phenylamino]-2-methyl-phenyl}-2-methylsulfanyl-4- pyridin-3-yl-thiophene-3-carbonitrile (370 mg, 0.76 mmol) in DCM (10 mL) was added Et₃N (155 mg, 0.15 mmol) followed by MsCl (130 mg, 1.15 mmol). The resulting mixture was stirred at ambient temperature for 10 min under nitrogen then poured into 20 ml water and extracted with DCM (20 ml×3). The combined organic layers were dried over Na₂SO₄ and concentrated in vacuo. The desired product was obtained (391 mg, 91%) and confirmed by LC/MS (Calculated: 565.12; observed: 565.1+1, ES+).

Example 31

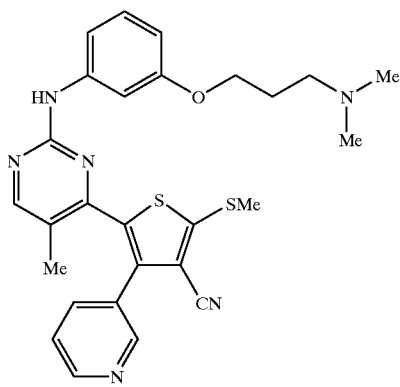

VI-18

5-{5-[3-(3-Dimethylamino-propoxy)-phenylamino]-2-methyl-phenyl}-2-methylsulfanyl-4-pyridin-3-yl-thiophene-3-carbonitrile (VI-18)

To a solution of methanesulfonic acid 3-{3-[3-(4-cyano-5-methylsulfanyl-3-pyridin-3-yl-thiophene-2-yl)-4-methyl-phenylamino]-phenoxyl}-propyl ester (20 mg, 0.035 mmol) in DCM (1 mL) was added excess dimethylamine and excess triethylamine. The reaction was stirred at ambient temperature for 3 hours then water (2 ml) was added and the product extracted with DCM (3 mL×3). The combined organic layer were concentrated to afford the crude product as an oil. Purification by chromatography (2% MeOH—CH₂Cl₂) afforded the desired product (17 mg, 95%). ¹H NMR (CDCl3): δ8.6(d, 1H), 8.5 (s, 1H), 8.1 (s, 1H), 7.7 (d, 1H), 7.4 –7.0 (m, 4H), 7.0(d, 1H), 6.5 (d, 1H), 4.1 (t, 2H), 2.9 (m, 2H), 2.7 (s, 3H), 2.6 (s, 6H), 2.1 (m, 2H), 1.6 (s, 3H).

Example 32

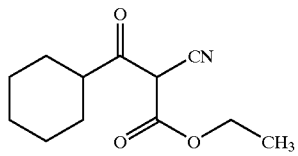

2-cyano-3-cyclohexyl-3-oxo-propionic acid ethyl ester

To a solution of ethyl cyanoacetate in acetonitrile was added MgCl₂ and Et₃N at 0° C. The resulting suspension was stirred at 0° C. for 30 minutes then cyclehexanecarbonyl chloride was added over 20 minutes and the reaction mixture stirred at 0° C. for 1 hour. The reaction mixture was partitioned between 1N HCl and ether, the organic phase was dried with MgSO₄ then concentrated under reduced pressure.

Example 33

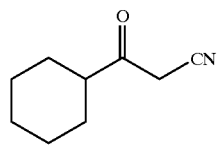

3-cyclohexyl-3-oxo-propionitrile

A solution of 2-cyano-3-cyclohexyl-3-oxo-propionic acid ethyl ester in DMSO:water (10:1) was stirred at 120° C. for 2 hours. The reaction mixture was partitioned between ether and 1N HCl, the organic phase was dried with MgSO₄ and the solvent removed under reduced pressure.

Example 34

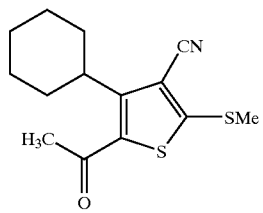

5-Acetyl-4-cyclohexyl-2-methylsulfanyl-thiophene-3-carbonitrile

To a solution of 3-cyclohexyl-3-oxo-propionitrile in DMF:CS₂ (1:1) was added K₂CO₃ at 0° C. and the reaction mixture stirred at ambient temperature for 2 hours. To the resulting reaction mixture was added chloroacetone (1 equivalent) and the reaction mixture stirred at ambient temperature for 3 hours. Iodomethane was then added and the resulting mixture was stirred at ambient temperature overnight. The reaction mixture was partitioned between ethyl acetate and brine, the organic phase dried with MgSO₄ and the solvent was removed under reduced pressure. The crude product was purified by silica gel chromatography.

Example 35

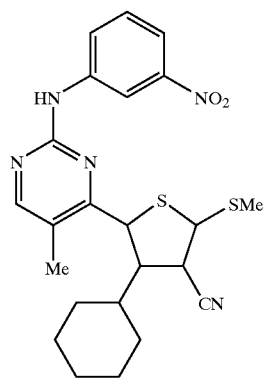

V-7

5-[2-(3-Nitrophenylamino)-5-methyl-pyrimidin-4-yl]-4-cyclohexyl-2-methylsulfanyl-thiophene-3-carbonitrile (V-7)

To a solution of 4-cyclohexyl-5-(3-dimethylamino-2-methyl-acryloyl)-2-methylsulfanyl-thiophene-3-carbonitrile (0.5 g, 1.7 mmol) in toluene (3 ml) was added DMF-DMA and the reaction was heated at 90° C. overnight resulting in conversion to product as determined by TLC (40% EtOAc:hexanes). The crude product was combined with DMF (10 ml) and 3-Nitrophenylguanidine (0.5 g, 2.78 mmol) in a sealed tube and heated at 120° C. overnight resulting in conversion to product as determined by TLC (40% EtOAc:hexanes). The reaction was partitioned between EtOAc and water, the organics were dried over sodium sulfate then concentrated in vacuo. The crude product was purified by chromatography (silica gel, 10% EtOAC:hexanes) to afford 0.334 g (3.05 umol) of V-7 in 42% yield for 2 steps. $^1$H NMR (CDCl$_3$) δ1.0–2.0 (m, 10H), 2.1 (s, 3H), 2.6(s, 3H), 7.4(m, 1H), 7.7 (d, 1H), 7.8 (d, 1H), 8.3 (s, 1H), 8.7 (s, 1H).

Example 36

V-8

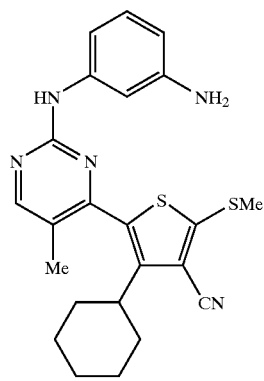

5-[2-(3-Aminophenylamino)-5-methyl-pyrimidin-4-yl]-4-cyclohexyl-2-methylsulfanyl-thiophene-3-carbonitrile (V-8)

A suspension of 5-[2-(3-Nitrophenylamino)-5-methyl-pyrimidin-4-yl]-4-cyclohexyl-2-methylsulfanyl-thiophene-3-carbonitrile (0.187 g, 402 umol) and 10% palladium on carbon in methanol was stirred under a hydrogen atmosphere overnight resulting in complete conversion to product as determined by TLC (40% EtOAc:hexanes). The reaction was filtered through celite and concentrated in vacuo to afford the desired amine V-8 (0.186 g, 426 umol) in quantitative yield. $^1$NMR (CDCl$_3$) δ1.0–1.1(m, 10H), 2.1 (s, 3H), 2.6 (s, 3H), 6.2 (d, 1H), 6.8 (d, 1H), 6.9–7.0 (m, 3H), 8.2 (s, 1H).

Example 37

VI-26

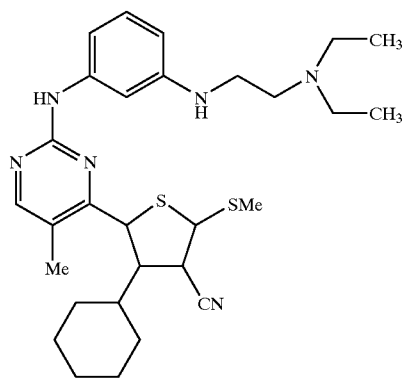

4-cyclohexyl-5-{2-(3-(2-diethylamino-ethylamino)-phenylamino)-5-methyl-pyrimidin-4-yl}2-methylsulfanyl-thiophene-3-carbonitrile (VI-26)

To a solution of 5-[2-(3-aminophenylamino)-5-methyl-pyrimidin-4-yl]-4-cyclohexyl-2-methylsulfanyl-thiophene-3-carbonitrile (20 mg, 45.91 micromol) and N,N-diethyl-2-amino-bromoethane.HBr (12 mg, 45.91 micromol) in THF was added sodium t-butoxide (9 mg, 91.82 micromol) and the eaction was stirred at ambient temperature overnight. TLC indicated conversion to product (10% MeOH:CH$_2$Cl$_2$). The reaction was partitioned between EtOAc and water, the organics were dried over sodium sulfate then concentrated in vacuo. The crude product was purified by chromatography (silica gel, 5% MeOH:CH$_2$Cl$_2$) to afford VI-26 in 33% yield. δ0.95 (bs, 6H), 1.0–1.8 (m, 10H), 2.0 (s, 3H), 2.6 (s, 3H), 2.75 (bs, 2H), 3.4 (s, 1H), 3.6 (bs, 2H), 4.0 (bs, 2H), 5.2 (s, 1H), 6.5 (d, 1H), 6.55 (s, 1H), 6.6 (d, 1H), 7.0 (t, 1H), 8.1 (s, 1H).

Example 38

VI-138

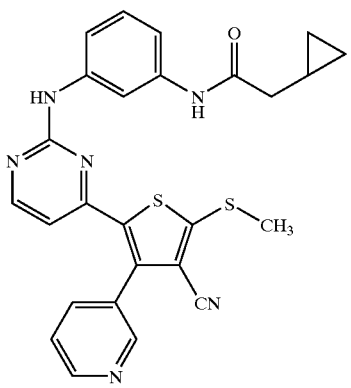

3-cyano-4-(3-pyridyl)-5-[2-(3-N-cyclopropylacetamido)-aminophenylamino]-pyrimidin-4-yl-2-thiomethyl thiophene (VI-138)

Placed together in a small vial were: 5-[2-(3-aminophenylamino)-pyrimidin-4-yl]-3-cyano-4-(3-pyridyl)-2-methylthio-thiophene (25 mg; 60 umol), cyclopropylacetic acid ( 25 mg; 240 umol), 1-(3-dimethylaminopropylo-3-ethylcarbodiimide hydrochloride [EDCI] (25 mg; 130 umol); and a catalytic amount (10% w/w) of N-hydroxy-benzatriazole [HOBT]. One milliliter of a 2.5 mM solution of diisopropylethylamine in dry DMF was added to the vial and the resulting solution was stirred for 18 hours at ambient temperature. Reaction was monitored by reverse phase HPLC and determined to be complete. Removal of the solvent via high vacuum and subsequent purification via preparative reverse phase HPLC on C18 silica with a gradient of water/acetonitrile containing 0.1% trifluoroacetic acid afforded eight milligrams of the title compound as a medium yellow powder; a 25.8% yield. $^1$NMR in methanol-d4: δ0.25 (mult; 2H), 0.6 (mult; 2H), 1.15 (mult; 1H), 2.3 (d; 2H), 2.85 (s; 3H), 6.4 (d; 1H), 7.15 (mult; 1H), 7.21 (mult; 2H), 7.85 (mult; 1H), 8.25 (d; 1H), 8.35 (d; 1H), 8.75 (mult; 1H), 8.82 (mult; 1H). m/e (ES+) 499.0

Example 39

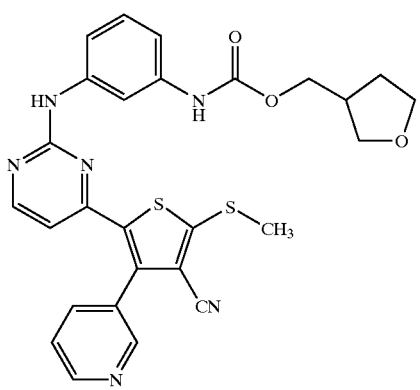

VI-143

3-cyano-4-(3-pyridyl)-5-(-2-(3-tetrahydrofuran-3-methyleneoxycarbamoyl) aminophenylamino)-pyrimidin-4-yl-2-thiomethyl thiophene (VI-143)

5-[2-(3-Aminophenylamino)-pyrimidin-4-yl]-3-cyano-4-(3-pyridyl)-2-thiomethyl thiophene (50 mg, 120 uM) was suspended/dissolved in 2.0 mL of a 0.25 M solution of diisopropylethylamine in p-dioxane. Added to this suspension/solution was (200 uL, 120 uM) of a 0.55 M solution of 2-hydroxymethyltetetrahydrofuran chloroformate in dry p-dioxane (The chloroformate was made previously according to a literature procedure and utilized as a stock solution.). The resulting solution was stirred at ~35 C. for 4 hrs. The reaction was determined to be complete by analytical reverse phase HPLC. The solvent was removed under reduced pressure and the resulting residue was dissolved in DMSO. This crude material was purified via preparative reverse phase HPLC on C18 silica utilizing a gradient of water/acetonitrile containing 0.1% TFA. This resulted in 10 mg of the title compound as a yellow amorphous powder, in 15.2% yield. $^1$NMR in methanol d4: δ1.75 (mult, 1H), 2.15 (mult; 1H), 2.85 (s; 3H), 3.65 (mult; 1H), 3.76 (mult; 1H), 3.86 (mult; 2H), 4.07 (mult; 1H), 4.16 (mult; 1H), ), 6.4 (d; 1H), 7.15 (mult; 1H), 7.21 (mult; 2H), 7.85 (mult; 1H), 8.25 (d; 1H), 8.35 (d; 1H), 8.75 (mult; 1H), 8.82 (mult; 1H) m/e (ES+) 545.

Example 40

We have prepared other compounds of formula VI by methods substantially similar to those described in the above Examples 22–39 and those illustrated in Schemes I–VII. The characterization data for these compounds is summarized in Table 12 below and includes $^1$NMR and HPLC data.

$^1$H NMR data is summarized in Table 12 below wherein "Y" designates $^1$NMR data is available and was found to be consistant with structure. Compound numbers correspond to the compound numbers listed in Table 8.

TABLE 12

Characterization Data for Selected Compounds of Formula VI

| Compound No | M + 1 | R$_t$ | Method | $^1$H NMR |
|---|---|---|---|---|
| VI-1 | 538.16 | 3.18 | A | Y |
| VI-2 | 538.17 | 3.28 | A | Y |

TABLE 12-continued

Characterization Data for Selected Compounds of Formula VI

| Compound No | M + 1 | R$_t$ | Method | $^1$H NMR |
|---|---|---|---|---|
| VI-3 | 524.14 | 3.15 | A | Y |
| VI-4 | 564.2 | 3.23 | A | Y |
| VI-5 | 578.21 | 3.23 | A | Y |
| VI-6 | 564.20 | 3.24 | A | Y |
| VI-7 | 593.20 | 2.90 | A | Y |
| VI-8 | 564.18 | 3.22 | A | Y |
| VI-9 | 577.21 | 2.98 | A | Y |
| VI-10 | 549.17 | 2.76 | A | Y |
| VI-11 | 640.19 | 2.703 | A | Y |
| VI-12 | 534.18 | 3.35 | A | Y |
| VI-13 | 531.15 | 3.28 | A | Y |
| VI-14 | 545.13 | 3.36 | A | Y |
| VI-15 | 551.15 | 3.25 | A | Y |
| VI-16 | 566.13 | 3.35 | A | Y |
| VI-17 | 552.11 | 3.43 | A | Y |
| VI-18 | 517.2 | 4.81 | B | Y |
| VI-19 | 547.2 | 4.57 | B | Y |
| VI-20 | 547.2 | 2.51 | A | Y |
| VI-21 | 533.2 | 2.36 | A | Y |
| VI-22 | 573.2 | 2.40 | A | Y |
| VI-23 | 587.2 | 4.64 | B | Y |
| VI-24 | 573.2 | 2.47 | A | Y |
| VI-25 | 602.2 | 4.78 | B | Y |
| VI-26 | 535.21 | 2.62 | A | Y |
| VI-27 | 575.20 | 3.23 | A | Y |
| VI-28 | 549.16 | 3.13 | A | Y |

Example 41

2-Ethylamino-4-phenyl-5-propionyl-thiophene-3-carboxylic acid ethyl ester

To a stirring slurry of ethyl benzoylacetate (30 mmol) and K$_2$CO$_3$ (1.2 equivalents, 36 mmol) in DMF (30 mL) was added ethyl thioisocyanate (1.0 equivalent, 30 mmol) and stirred for 16 hours. The chloroacetone (1.0 equivalent, 30 mmol) was added to the mixture at room temperature and stirred for 3 hours. To the mixture was added water (150 mL) at room temperature with vigorous stirring. The solid was collected and washed with water (30 mL) and hexane (50 mL). The solid was dried under nitrogen pressure.

Example 42

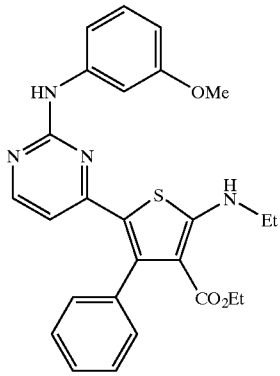

IIa-90

2-Ethylamino-5-[2-(3-methoxy-phenylamino)-pyrimidin-4-yl]-4-phenyl-thiophene-3-carboxylic acid ethyl ester (IIa-90)

This compound was prepared from 2-ethylamino-4-phenyl-5-propionyl-thiophene-3-carboxylic acid ethyl ester using the essentially the same general methods as described above. MS cal:474.17, obs [M+H]=475.1; $^1$H NMR(DMSO) 9.44(s, 1H), 8.37(t, J=5.8 Hz, 1H), 7.93(d, J=5.5 Hz, 1H), 7.63(s, 1H), 7.45(m, 3H), 7.24(m, 3H), 7.17(t, J=8.1 Hz, 1H), 6.53(dd, J=2.4, 8.1 Hz, 1H), 5.54(d(J=5.6 Hz, 1H), 3.80(s, 3H), 3.80(q, J=7.2 Hz, 2H), 3.40(quintet, J=7.1 Hz, 2H), 1.32(t, J=7.2 Hz, 3H), 0.67(t, J=7.1 Hz, 3H).

The following examples demonstrate how the compounds of this invention may be tested as inhibitors of c-Jun-N-terminal, Src, and Lck kinases.

Example 43

Cloning, Expression and Purification of JNK3 Protein

A BLAST search of the EST database using the published JNK3α1 cDNA as a query identified an EST clone (#632588) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites. The protein was expressed in *E. coli*. Due to the poor solubility of the expressed full-length protein (Met 1-Gln 422), an N-terminally truncated protein starting at Ser residue at position 40 (Ser 40) was produced. This truncation corresponds to Ser 2 of JNK1 and JNK2 proteins, and is preceded by a methionine (initiation) and a glycine residue. The glycine residue was added in order to introduce an NcoI site for cloning into the expression vector. In addition, systematic C-terminal truncations were performed by PCR to identify a construct that give rise to diffraction-quality crystals. One such construct encodes amino acid residues Ser40-Glu402 of JNK3α1 and is preceded by Met and Gly residues.

The construct was prepared by PCR using deoxyoligo-nucleotides: 5' GCTCTAGAGCTCC<u>ATG</u>GGCAGCAAAA-GCAAAGTTGACAA 3' (forward primer with initiation codon underlined)(SEQ ID NO:1) and 5' TAGCGGATCC <u>TCA</u>TTCTGAATTCATTACTTCCTTGTA 3' (reverse primer with stop codon underlined)(SEQ ID NO:2) as primers and was confirmed by DNA sequencing. Control experiments indicated that the truncated JNK3 protein had an equivalent kinase activity towards myelin basic protein when activated with an upstream kinase MKK7 in vitro.

*E.coli* strain BL21 (DE3) (Novagen) was transformed with the JNK3 expression construct and grown at 30° C. in LB supplemented with 100 μg/ml carbenicillin in shaker flasks until the cells were in log phase (OD$_{600}$~0.8). Isopropylthio-β-D-galactosidase (IPTG) was added to a final concentration of 0.8 mM and the cells were harvested 2 hours later by centrifugation.

*E. coli* cell paste containing JNK3 was resuspended in 10 volumes/g lysis buffer (50 mM HEPES, pH 7.2, containing 10% glycerol (v/v), 100 mM NaCl, 2 mM DTT, 0.1 mM PMSF, 2 μg/ml Pepstatin, lug/ml each of E-64 and Leupeptin). Cells were lysed on ice using a microfluidizer and centrifuged at 100,000×g for 30 min at 4° C. The 100,000×g supernatant was diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin was washed with 5 column volumes of Buffer A, followed by 5 column volumes of Buffer A containing 50 mM NaCl. Bound JNK3 was eluted with a 7.5 column volume linear gradient of 50–300 mM NaCl. JNK3 eluted between 150–200 mM NaCl.

Example 44

Activation of JNK3

Five mg of JNK3 was diluted to 0.5 mg/ml in 50 mM HEPES buffer, pH 7.5, containing 100 mM NaCl, 5 mM DTT, 20 mM MgCl$_2$ and 1 mM ATP. GST-MKK7(DD) was added at a molar ratio of 1:2.5 GST-MKK7:JNK3. After incubation for 30 minutes at 25° C., the reaction mixture was concentrated 5-fold by ultrafiltration in a Centriprep-30 (Amicon, Beverly, Mass.), diluted to 10 ml and an additional 1 mM ATP added. This procedure was repeated three times to remove ADP and replenish ATP. The final addition of ATP was 5 mM and the mixture incubated overnight at 4° C.

The activated JNK3/GST-MKK7(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interaction chromatography (at 25° C.) using a Rainin Hydropore column. GST-MKK7 and unactivated JNK3 do not bind under these conditions such that when a 1.1 to 0.05 M potassium phosphate gradient is developed over 60 minutes at a flow rate of 1 ml/minute, doubly phosphory-lated JNK3 is separated from singly phosphorylated JNK. Activated JNK3 (i.e. doubly phosphorylated JNK3) was stored at −70° C. at 0.25–1 mg/ml.

Example 45

JNK Inhibition Assay

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM MgCl$_2$, 2.5 mM phosphoenolpyruvate, 200 μM NADH, 150 μg/mL pyruvate kinase, 50 μg/mL lactate dehydrogenase, and 200 μM EGF receptor peptide. The EGF receptor peptide has the sequence KRELVEPLTPSGEAPNQALLR, and is a phosphoryl acceptor in the JNK3-catalyzed kinase reaction. The reaction was initiated by the addition of 10 μM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

Table 13 shows the results of the activity of selected compounds of this invention in the JNK inhibition assay. The compound numbers correspond to the compound numbers in Tables 1, 2, and 7. Compounds having a $K_i$ less than 0.1 micromolar (μM) are rated "A", compounds having a $K_i$ between 0.1 and 1 μM are rated "B" and compounds having a $K_i$ greater than 1 μM are rated "C". Compounds having an activity designated as "D" provided a percent inhibition less than or equal to 24%; compounds having an activity designated as "E" provided a percent inhibition of between 24% and 66%; and compounds having an activity designated as "F" provided a provided a percent inhibition of between 67% and 100%.

TABLE 13

JNK3 Activity of Selected Compounds

| No. | Activity | No. | Activity | No. | Activity |
|---|---|---|---|---|---|
| IIa-1 | D | IIa-2 | F | IIa-3 | D |
| IIa-4 | F | IIa-5 | D | IIa-6 | E |
| IIa-7 | D | IIa-8 | D | IIa-9 | D |
| IIa-10 | A | IIa-11 | A | IIa-12 | E |
| IIa-13 | B | IIa-14 | A | IIa-15 | A |
| IIa-16 | C | — | — | — | — |
| IIb-1 | D | IIb-2 | D | IIb-3 | D |
| IIb-4 | D | IIb-5 | D | IIb-6 | D |
| V-1 | B | — | — | — | — |

Example 46

The compounds were evaluated as inhibitors of human Src kinase using either a radioactivity-based assay or spectrophotometric assay.

Src Inhibition Assay A: Radioactivity-based Assay

The compounds were assayed as inhibitors of full length recombinant human Src kinase (from Upstate Biotechnology, cat. no. 14-117) expressed and purified from baculo viral cells. Src kinase activity was monitored by following the incorporation of $^{33}$p from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM MgCl$_2$, 2 mM DTT, 0.25 mg/ml BSA, 10 µM ATP (1–2 uCi $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells.

Inhibitors dissolved in DMSO were added to the wells to give a final DMSO concentration of 2.5%. The assay plate was incubated at 30° C. for 10 min before initiating the reaction with $^{33}$P-ATP. After 20 min of reaction, the reactions were quenched with 150 µl of 10% trichloroacetic acid (TCA) containing 20 mM Na$_3$PO$_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM Na$_3$PO$_4$ and then 4 times with methanol. 200 µl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM MgCl2, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 µM NADH, 30 µg/ml pyruvate kinase and 10 µg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30 C. for 10 min before initiating the reaction with 100 µM ATP. The absorbance change at 340 nm with time, the rate of the reaction, was monitored on a molecular devices plate reader. The data of rate as a function of the inhibitor concentration was fitted to compettive inhibition kinetics model to get the $K_i$ for the compound.

Table 14 shows the results of the activity of selected compounds of this invention in the Src inhibition assay. The compound numbers correspond to the compound numbers in Tables 1, 2, 7, and 8. Compounds having a $K_i$ less than 0.1 micromolar (µM) are rated "A", compounds having a $K_i$ between 0.1 and 1 µM are rated "B" and compounds having a $K_i$ greater than 1 µM are rated "C". Compounds having an activity designated as "D" provided a percent inhibition less than or equal to 24%; compounds having an activity designated as "E" provided a percent inhibition of between 24% and 66%; and compounds having an activity designated as "F" provided a provided a percent inhibition of between 67% and 100%.

TABLE 14

Src Activity of Selected Compounds

| No. | Activity | No. | Activity | No. | Activity |
|---|---|---|---|---|---|
| IIa-1 | D | IIa-2 | D | IIa-3 | D |
| IIa-4 | E | IIa-5 | D | IIa-6 | D |
| IIa-7 | D | IIa-8 | E | IIa-9 | D |
| IIa-10 | F | IIa-11 | F | IIa-12 | F |
| IIa-13 | F | IIa-14 | F | IIa-15 | F |
| IIa-42 | A | IIa-43 | A | IIa-44 | A |
| IIa-49 | B | IIa-50 | A | IIa-68 | A |
| IIa-69 | A | IIa-71 | A | IIa-72 | B |
| IIa-73 | B | IIa-81 | A | IIa-82 | B |
| IIa-83 | A | IIa-86 | B | IIa-87 | B |
| IIa-88 | B | IIa-89 | A | IIa-90 | C |
| IIb-1 | D | IIb-2 | D | IIb-3 | D |
| IIb-4 | E | IIb-5 | D | IIb-6 | D |
| V-4 | A | V-5 | A | V-15 | A |
| V-29 | A | V-30 | A | — | — |
| VI-18 | A | VI-19 | A | VI-20 | A |
| VI-21 | B | VI-22 | A | VI-23 | A |
| VI-24 | A | VI-25 | A | VI-117 | B |
| VI-118 | B | VI-119 | B | VI-120 | A |
| VI-130 | A | VI-132 | B | VI-133 | A |
| VI-134 | A | VI-135 | A | VI-141 | A |

Example 47

The compounds were evaluated as inhibitors of human Lck kinase using either a radioactivity-based assay or spectrophotometric assay.

Lck Inhibition Assay A: Radioactivity-based Assay

The compounds were assayed as inhibitors of full length bovine thymus Lck kinase (from Upstate Biotechnology, cat. no. 14-106) expressed and purified from baculo viral cells. Lck kinase activity was monitored by following the incorporation of $^{33}$p from ATP into the tyrosine of a random poly Glu-Tyr polymer substrate of composition, Glu:Tyr=4:1 (Sigma, cat. no. P-0275). The following were the final concentrations of the assay components: 0.025 M HEPES, pH 7.6, 10 mM MgCl$_2$, 2 mM DTT, 0.25 mg/ml BSA, 10 μM ATP (1–2 μCi $^{33}$P-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30 C. for 10 min before initiating the reaction with $^{33}$P-ATP. After 20 min of reaction, the reactions were quenched with 150 μl of 10% trichloroacetic acid (TCA) containing 20 mM Na$_3$PO$_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM Na$_3$PO$_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.

Lck Inhibition Assay B: Spectrophotometric Assay

The ADP produced from ATP by the human recombinant Lck kinase-catalyzed phosphorylation of poly Glu-Tyr substrate was quanitified using a coupled enzyme assay (Fox et al (1998) *Protein Sci* 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM MgCl$_2$, 2 mM DTT, 5 mg/ml poly Glu-Tyr, and 50 nM of recombinant human Lck kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with 150 μM ATP. The absorbance change at 340 nm with time, the rate of the reaction, was monitored on a molecular devices plate reader. The data of rate as a function of the inhibitor concentration was fitted to competitive inhibition kinetics model to get the $K_i$ for the compound.

Table 15 shows the results of the activity of selected compounds of this invention in the Lck inhibition assay. The compound numbers correspond to the compound numbers in Tables 1, 7, and 8. Compounds having a $K_i$ less than 0.1 micromolar (μM) are rated "A", compounds having a $K_i$ between 0.1 and 1 μM are rated "B" and compounds having a $K_i$ greater than 1 μM are rated "C".

TABLE 15

Lck Activity of Selected Compounds

| No. | Activity | No. | Activity | No. | Activity |
|---|---|---|---|---|---|
| IIa-10 | A | IIa-11 | B | IIa-14 | A |
| IIa-15 | A | IIa-38 | A | IIa-39 | A |
| IIa-40 | A | IIa-41 | C | IIa-42 | A |
| IIa-43 | A | IIa-44 | A | IIa-45 | A |
| IIa-46 | A | IIa-47 | B | IIa-48 | A |
| IIa-49 | B | IIa-50 | A | IIa-51 | A |
| IIa-52 | C | IIa-53 | C | IIa-54 | C |
| IIa-55 | C | IIa-56 | C | IIa-57 | A |
| IIa-58 | A | IIa-59 | A | IIa-60 | A |
| IIa-61 | A | IIa-62 | C | IIa-63 | A |
| IIa-64 | A | IIa-65 | B | IIa-66 | A |
| IIa-67 | A | IIa-68 | A | IIa-69 | A |
| IIa-70 | A | IIa-71 | A | IIa-72 | B |
| IIa-73 | B | IIa-74 | C | IIa-75 | A |
| IIa-76 | C | IIa-77 | B | IIa-78 | C |
| IIa-79 | A | IIa-80 | C | IIa-81 | A |
| IIa-82 | C | IIa-83 | B | IIa-84 | C |
| IIa-85 | — | IIa-86 | A | IIa-87 | A |
| IIa-88 | B | IIa-89 | A | IIa-90 | B |
| IIa-91 | A | IIa-92 | A | IIa-97 | A |
| IIa-98 | A | IIa-99 | A | IIa-100 | A |
| IIa-101 | A | IIa-105 | A | IIa-106 | A |
| IIa-107 | B | IIa-108 | A | — | — |
| V-1 | A | V-2 | A | V-3 | A |
| V-4 | A | V-5 | A | V-6 | A |
| V-7 | A | V-8 | A | V-9 | A |
| V-10 | A | V-11 | A | V-12 | B |
| V-13 | A | V-14 | B | V-15 | A |
| V-16 | B | V-17 | B | V-18 | A |
| V-19 | A | V-20 | A | V-21 | A |
| V-22 | C | V-23 | C | V-24 | A |
| V-25 | A | V-26 | A | V-27 | A |
| V-28 | A | V-29 | A | V-30 | A |
| V-31 | C | V-32 | A | — | — |
| VI-1 | A | VI-2 | A | VI-3 | A |
| VI-4 | A | VI-5 | A | VI-6 | A |
| VI-7 | A | VI-8 | A | VI-9 | A |
| VI-10 | A | VI-11 | A | VI-12 | A |
| VI-13 | A | VI-14 | A | VI-15 | A |
| VI-16 | A | VI-17 | A | VI-18 | A |
| VI-19 | A | VI-20 | A | VI-21 | A |
| VI-22 | B | VI-23 | C | VI-24 | A |
| VI-25 | B | VI-117 | B | VI-118 | A |
| VI-119 | A | VI-120 | A | VI-121 | B |
| VI-122 | A | VI-123 | B | VI-124 | B |
| VI-125 | B | VI-126 | B | VI-127 | B |
| VI-128 | A | VI-129 | A | VI-130 | A |
| VI-131 | A | VI-132 | A | VI-133 | A |
| VI-134 | A | VI-135 | A | VI-136 | A |
| VI-137 | A | VI-138 | A | VI-139 | A |
| VI-140 | A | VI-141 | A | — | — |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula I:

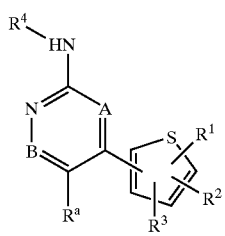

or a pharmaceutically acceptable salt thereof, wherein:
A is N and B is CH;
$R^1$ and $R^2$ are each independently selected from halogen, CN, $NO_2$, $N(R)_2$, OR, SR, or $(T)_n$—$R^5$;
$R^3$ is selected from a 3–6 membered carbocyclic or heterocyclic ring having one to two heteroatoms independently selected from nitrogen, oxygen, or sulfur, phenyl, or a 5–6 membered heteroaryl ring having one to three heteroatoms independently selected from nitrogen, oxygen, or sulfur, wherein said phenyl or heteroaryl ring is optionally substituted with one $(T)_n$—Ar and one to two $R^7$;
each n is independently selected from zero or one;
T is a $C_1$-$C_6$ alkylidene chain, wherein one methylene unit of T is optionally replaced by CO, $CO_2$, COCO, CONR, OCONR, NRNR, NRNRCO, NRCO, $NRCO_2$, NRCONR, $SO_2$, $NRSO_2$, $SO_2NR$, $NRSO_2NR$, O, S, or NR;
each R is independently selected from hydrogen or an optionally substituted $C_1$-$C_6$ aliphatic group; or two R on the same nitrogen atom may be taken together with the nitrogen to form a four to eight membered, saturated or unsaturated heterocyclic ring containing one to three heteroatoms independently selected from nitrogen, oxygen, or sulfur;
$R^4$ is $(T)_n$—R, $(T)_n$—Ar, or $(T)_n$—$Ar^1$;
$R^a$ is selected from $R^b$, halogen, $NO_2$, $OR^b$, $SR^b$, or $N(R^b)_2$;
$R^b$ is selected from hydrogen or a $C_1$-$C_4$ aliphatic group optionally substituted with oxo, OH, SH, $NH_2$, halogen, $NO_2$, or CN;
$R^5$ is an optionally substituted $C_1$-$C_6$ aliphatic or Ar;
Ar is a 5–6 membered saturated, partially unsaturated, or aryl monocyclic ring having zero to three heteroatoms independently selected from nitrogen, sulfur, or oxygen, or an 8–10 membered saturated, partially unsaturated, or aryl bicyclic ring having zero to four heteroatoms independently selected from nitrogen, sulfur, or oxygen, wherein Ar is optionally substituted with one to three $R^7$;
$Ar^1$ is a 6-membered aryl ring having zero to two nitrogens, wherein said ring is substituted with one Z—$R^6$ group and optionally substituted with one to three $R^7$;
Z is a $C_1$-$C_6$ alkylidene chain wherein up to two non-adjacent methylene units of Z are optionally replaced by CO, $C_2$, COCO, CONR, OCONR, NRNR, NRNRCO, NRCO, $NRC_2$, NRCONR, SO, $SO_2$, $NRSO_2$, $SO_2NR$, $NRSO_2NR$, O, S, or NR; provided that said optionally replaced methylene unit of Z is a methylene unit non-adjacent to $R^6$;
$R^6$ is selected from Ar, R, halogen, $NO_2$, CN, OR, SR, $N(R)_2$, NRC(O)R, $NRC(O)N(R)_2$, $NRC_2R$, C(O)R, $CO_2R$, OC(O)R, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$; and
each $R^7$ is independently selected from R, halogen, $NO_2$, CN, OR, SR, $N(R)_2$, NRC(O)R, $NRC(O)N(R)_2$, $NRCO_2R$, C(O)R, $CO_2R$, $C(O)N(R)_2$, $OC(O)N(R)_2$, SOR, $SO_2R$, $SO_2N(R)_2$, $NRSO_2R$, $NRSO_2N(R)_2$, C(O)C(O)R, or $C(O)CH_2C(O)R$; or two $R^7$ on adjacent positions of $Ar^1$ may be taken together to form a saturated, partially unsaturated, or fully unsaturated five to seven membered ring containing zero to three heteroatoms selected from O, S, or N.

2. The compound according to claim 1, wherein said compound has the formula IIa:

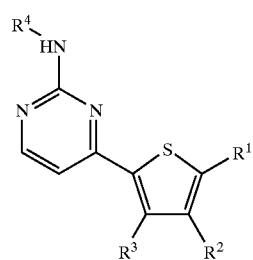

or a pharmaceutically acceptable salt thereof.

3. The compound according to claim 2, wherein said compound has one or more features selected from the group consisting of:
(a) $R^1$ is selected from $N(R)_2$, OR, SR, or $(T)_n$—$R^5$;
(b) T is a $C_{1-4}$ alkylidene chain, wherein one methylene unit of T is optionally replaced by S, O, N(R), or $CO_2$;
(c) $R^2$ is CN, R, halogen, $C_2R^5$, or $N(R)_2$;
(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one $(T)_n$—Ar group and one $R^7$; and
(e) $R^4$ is hydrogen or Ar, wherein Ar is an optionally substituted 6 membered saturated, partially saturated, or aryl ring having zero to two heteroatoms independently selected from nitrogen, oxygen, or sulfur.

4. The compound according to claim 3, wherein said compound has one or more features selected from the group consisting of:
(a) $R^1$ is selected from $SCH_2$-4-phenol, $SCH_3$, OH, OEt, $N(Me)_2$, OMe, 4-methylpiperidin-1-yl, NHEt, $NHCH_2CH_2$piperidin-1-yl, or $NHCH_2CH_2$morpholin-4-yl;
(b) $R^2$ is CN or $CO_2R^5$;
(c) $R^3$ is selected from phenyl, pyridyl, pyrimidinyl, cyclohexyl, or furanyl, wherein $R^3$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethyl-isoxazolyl, 3-ethoxyphenyl, 4-isopropylphenyl, 4-F-3-Cl-phenyl, pyrrolyl, pyrimidinyl, chloro, bromo, fluoro, trifluoromethyl, OH, $NH_2$, methyl, methoxy or ethoxy; and
(d) $R^4$ is selected from hydrogen or a phenyl, benzyl, pyridyl, piperidinyl, or cyclohexyl ring, wherein said ring is optionally subsituted with benzyloxy, phenoxy, $SO_2NH_2$, OH, $NO_2$, $NH_2$, OMe, Br, Cl, $CO_2Me$, $NHSO_2Me$, $NHSO_2Et$, $NHCON(Me)_2$, $NHCON(Et)_2$, NHCOpyrrolidin-1-yl, or NHCOmorpholin-4-yl.

5. The compound according to claim 1, wherein said compound has the formula IIb:

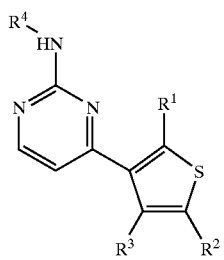

IIb or a pharmaceutically acceptable sat thereof.

6. The compound according to claim 5, wherein said compound has one or more features selected from the group consisting of:
(a) $R^1$ is selected from $N(R)_2$, OR, SR, or $(T)_n$—$R^5$;
(b) T is a $C_{1-4}$ alkylidene chain, wherein one methylene unit of T is optionally replaced by S, O, N(R), or $C_2$;
(c) $R^2$ is CN, $R^7$, Ar, halogen, or $N(R^6)_2$;
(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one $(T)_n$—Ar group and one $R^7$; and
(e) $R^4$ is hydrogen or Ar, wherein Ar is an optionally substituted 6 membered saturated, partially saturated, or aryl ring having zero to two heteroatoms independently selected from nitrogen, oxygen, or sulfur.

7. The compound according to claim 6, wherein said compound has one or more features selected from the group consisting of:
(a) $R^1$ is selected from $SCH_2$-4-phenol, $SCH_3$, OH, OEt, $N(Me)_2$, OMe, 4-methylpiperidin-1-yl, NHEt, $NHCH_2CH_2$piperidin-1-yl, or $NHCH_2CH_2$morpholin-4-yl;
(b) $R^2$ is CN or 4-($C_{1-3}$ alkyl)-thiazol-2-yl;
(c) $R^3$ is selected from phenyl, pyridyl, pyrimidinyl, cyclohexyl, or furanyl, wherein $R^3$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, OH, $NH_2$, methyl, methoxy or ethoxy; and
(d) $R^4$ is selected from hydrogen or a phenyl, benzyl, pyridyl, piperidinyl, or cyclohexyl ring, wherein said ring is optionally subsituted with benzyloxy, phenoxy, $SO_2NH_2$, OH, $NO_2$, $NH_2$, OMe, Br, Cl, $CO_2Me$, $NHSO_2Me$, $NHSO_2Et$, $NHCON(Me)_2$, $NHCON(Et)_2$, NHCOpyrrolidin-1-yl, or NHCOmorpholin-4-yl.

8. The compound according to claim 1, wherein said compound has the formula V:

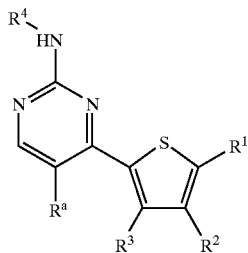

V or a pharmaceutically acceptable salt thereof.

9. The compound according to claim 8, wherein said compound has one or more of the following features:
(a) $R^1$ is selected from $N(R)_2$, OR, SR, or $(T)_n$—$R^5$;
(b) T is a $C_{1-4}$ alkylidene chain, wherein one methylene unit of T is optionally replaced by S, O, N(R), or $C_2$;
(c) $R^2$ is CN, R, halogen, $CO_2R^5$, or $N(R)_2$;
(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one $(T)_n$—Ar group and one $R^7$;
(e) $R^4$ is hydrogen or Ar, wherein Ar is an optionally substituted 6 membered saturated, partially saturated, or aryl ring having zero to two heteroatoms independently selected from nitrogen, oxygen, or sulfur; and
(f) $R^a$ is selected from $R^b$, $OR^b$, $SR^b$, or $N(R^b)_2$.

10. The compound according to claim 9, wherein said compound has one or more of the following features:
(a) $R^1$ is selected from $SCH_2$-4-phenol, $SCH_3$, OH, OEt, $N(Me)_2$, OMe, 4-methylpiperidin-1-yl, NHEt, $NHCH_2CH_2$piperidin-1-yl, or $NHCH_2CH_2$morpholin-4-yl;
(b) $R^2$ is CN or $CO_2R^5$;
(c) $R^3$ is selected from phenyl, pyridyl, pyrimidinyl, cyclohexyl, or furanyl, wherein $R^3$ is optionally substituted with phenyl, phenoxy, benzyl, benzyloxy, pyridyl, 3-hydroxyphenyl, 2-hydroxyphenyl, 3-aminophenyl, N-BOC-pyrrolyl, 4-chlorophenyl, 3-ethoxypyridyl, 2-methoxypyridyl, 2,5-dimethylisoxazolyl, 3-ethoxyphenyl, 4-isopropylphenyl, 4-F-3-Cl-phenyl, pyrrolyl, pyrimidinyl, chloro, bromo, fluoro, trifluoromethyl, OH, $NH_2$, methyl, methoxy or ethoxy;
(d) $R^4$ is selected from hydrogen or a phenyl, benzyl, pyridyl, piperidinyl, or cyclohexyl ring, wherein said ring is optionally subsituted with benzyloxy, phenoxy, $SO_2NH_2$, OH, $NO_2$, $NH_2$, OMe, Br, Cl, $CO_2Me$, $NHSO_2Me$, $NHSO_2Et$, $NHCON(Me)_2$, $NHCON(Et)_2$, NHCOpyrrolidin-1-yl, or NHCOmorpholin-4-yl; and
(e) $R^a$ is methyl, OH, OMe, or $NH_2$.

11. The compound according to claim 1, wherein said compound has the formula VI:

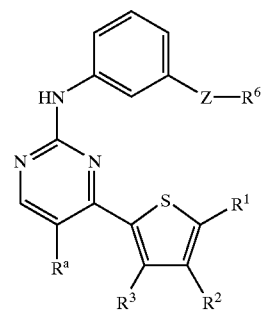

VI or a pharmaceutically acceptable salt thereof.

12. The compound according to claim 11, wherein said compound has one or more features selected from the group consisting of:
(a) $R^1$ is $N(R)_2$, OR, SR, or $(T)_n$—$R^5$;
(b) T is a $C_{1-4}$ alkylidene chain, wherein one methylene unit of T is optionally replaced by S, O, N(R), or $CO_2$;
(c) $R^2$ is CN, $R^7$, halogen, or $N(R^6)_2$;

(d) $R^3$ is a 5–6 membered ring selected from carbocyclic, phenyl, or a heterocyclyl or heteroaryl ring having one to two heteroatoms independently selected from nitrogen, oxygen or sulfur, wherein $R^3$ is optionally substituted with one $(T)_n$—Ar group and one $R^7$;

(e) Z is a $C_{1-4}$ alkylidene chain wherein one methylene unit of Z is optionally replaced by O, NH, NHCO, $NHCO_2$, $NHSO_2$, CONH;

(f) $R^6$ is selected from $N(R)_2$, NHCOR, or Ar wherein Ar is an optionally substituted 5–6 membered heterocyclic or heteroaryl ring having one to two heteroatoms independently selected from nitrogen, oxygen, or sulfur; and (g) $R^a$ is $R^b$, $OR^b$, $SR^b$, or $N(R^b)_2$.

13. The compound according to claim 12, wherein said compound has one or more features selected from the group consisting of:

(a) $R^1$ is selected from $SCH_2$-4-phenol, $SCH_3$, OH, OEt, $N(Me)_2$, OMe, 4-methylpiperidin-1-yl, NHEt, $NHCH_2CH_2$piperidin-1-yl, or $NHCH_2CH_2$morpholin-4-yl;

(b) $R^2$ is CN;

(c) $R^3$ is a phenyl, pyridyl, furyl, or cyclohexyl ring optionally substituted with $(T)_n$—Ar or $R^7$ wherein Ar is a 5–6 membered aryl ring having zero to two heteroatoms independently selected from nitrogen, oxygen, or sulfur, and wherein $R^7$ is selected from R, halogen, OR, $N(R)_2$, or $CO_2R$;

(d) $R^a$ is hydrogen or methyl; and (e) Z—$R^6$ is selected from $O(CH_2)_3OH$, $O(CH_2)_3NH(CH_2)_2OH$, $O(CH_2)_2NH(CH_2)_2OH$, $O(CH_2)_3N$(hydroxyethyl)(methyl), $O(CH_2)_3$pyrrolidin-1-yl, $O(CH_2)_2$morpholin-4-yl, $O(CH_2)_3N(Me)_2$, $O(CH_2)_3N(Et)_2$, $O(CH_2)_3$(4-hydroxyethylpiperazin-1-yl), $O(CH_2)_3$piperazin-1-yl, $O(CH_2)_3$(4-hydroxymethylpiperidin-1-yl), $O(CH_2)_3$(4-hydroxypiperidin-1-yl), $NHCO(CH_2)_3N(Me)_2$, $NHCO(CH_2)_3NCOCH_3$, $NHCOCH_2$pyridin-2-yl, $NHCOCH_2$(2-aminothiazol-4-yl), $NHCOCH_2$cyclopropyl, $NHCO(CH_2)_2N(Et)_2$, $NHCO(CH_2)_2$(piperazin-2,5-dione-3-yl), NHCOpyrrolidin-1-yl, NHCOmorpholin-4-yl, $NHCO_2CH_2$tetrahydrofuran-2-yl, $NHCO_2$tetrahydrofuran-2-yl, $NHCO_2$tetrahydropyran-4-yl, or $NHCO_2CH_2$tetrahydropyran-2-yl.

14. A compound selected from the following Table 1, Table 2, Table 7, or Table 8 compounds:

TABLE 1

Compounds of Formula IIa

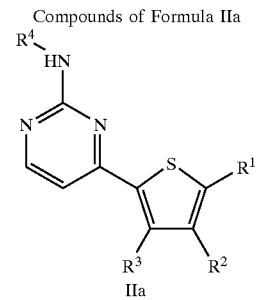

IIa

| No. IIa- | $R^1$ | $R^2$ | $R^3$ | $R^4$ |
|---|---|---|---|---|
| 1 | SMe | CN | 4-$CO_2H$-phenyl | H |
| 2 | SMe | CN | 4-Cl-phenyl | H |
| 3 | SMe | CN | 4-$CF_3$-phenyl | H |
| 4 | SMe | CN | 4-$CH_3$-phenyl | H |
| 5 | SMe | CN | 2-Cl-phenyl | H |
| 6 | SMe | CN | 4-$OCH_3$-phenyl | H |
| 7 | $NHCH_2Ph$ | CN | 4-$CF_3$-phenyl | H |
| 8 | $NHCH_2Ph$ | CN | 2-Cl-phenyl | H |
| 9 | $NHCH_2Ph$ | CN | 4-$OCH_3$-phenyl | H |
| 10 | SMe | CN | 4-Cl-phenyl | Ph |
| 11 | OEt | CN | 4-Cl-phenyl | Ph |
| 12 | SMe | CN | 4-$CF_3$-phenyl | Ph |
| 13 | OEt | CN | 4-$CF_3$-phenyl | Ph |
| 14 | SMe | CN | 4-$CH_3$-phenyl | Ph |
| 15 | OEt | CN | 4-$CH_3$-phenyl | Ph |
| 16 | SMe | CN | H | H |
| 17 | $CH_2CH_2OH$ | CN | OPh | Et |
| 18 | CONHEt | $CF_3$ | pyridine-3-yl | $CH_2Ph$ |
| 19 | $SCH_2Ph$ | NHEt | $CONHCH_2Ph$ | COPh |
| 20 | $CH_2NO_2$ | CONHEt | NH(4-Cl-phenyl) | H |
| 21 | $NHCONH_2$ | OMe | $CH_2Ph$ | $SO_2Me$ |
| 22 | Et | CN | thiazol-2-yl | Ph |
| 23 | SMe | CN | piperidin-1-yl | cyclohexyl |
| 24 | $OCH_2Ph$ | Cl | 4-CONHMe-phenyl | cyclohexyl |
| 25 | NHMe | $NO_2$ | NHPh | H |
| 26 | SMe | $NO_2$ | $NH_2$ | H |
| 27 | OEt | $NO_2$ | $NHCH_2Ph$ | H |
| 28 | NHMe | $NH_2$ | NHPh | Ph |
| 29 | SMe | $NH_2$ | $NH_2$ | Me |

TABLE 1-continued

Compounds of Formula IIa

IIa

| No. IIa- | R¹ | R² | R³ | R⁴ |
|---|---|---|---|---|
| 30 | OEt | NH₂ | NHCH₂Ph | Me |
| 31 | NHMe | NHCOEt | Ph | Ph |
| 32 | SME | NHCOEt | CH₂Ph | CH₂Ph |
| 33 | OEt | NHCOEt | CH₂Ph | H |
| 34 | NHMe | CONHMe | Ph | H |
| 35 | SMe | CONHMe | Ph | Ph |
| 36 | OEt | CONHMe | 4-Cl—Ph | Ph |
| 37 | SMe | CN | Ph | 3-OBn—Ph |
| 38 | SMe | CN | Ph | 3-SO₂NH₂—Ph |
| 39 | S—CH₂-phenol-4-ol | CN | Ph | Ph |
| 40 | SMe | CN | Ph | 3-OH—Ph |
| 41 | SMe | CN | Ph | 4-OBn—Ph |
| 42 | OH | CN | Ph | 3-OBn—Ph |
| 43 | SMe | CN | cyclohexyl | 3,5-OMe—Ph |
| 44 | SMe | CN | cyclohexyl | 3-SO₂NH₂—Ph |
| 45 | SMe | CN | cyclohexyl | 3-OBn—Ph |
| 46 | SMe | CN | cyclohexyl | Ph |
| 47 | SMe | CN | cyclohexyl | 4-CO₂Et—Ph |
| 48 | SMe | CN | cyclohexyl | 3-OH—Ph |
| 49 | SMe | CN | 3-OMe—Ph | 3-NO₂—Ph |
| 50 | SMe | CN | 3-OMe—Ph | 3-NH₂—Ph |
| 51 | SMe | CN | 3-OH—Ph | 3-NO₂—Ph |
| 52 | SMe | CN | 3-OBn—Ph | Ph |
| 53 | SMe | CN | 3-OBn—Ph | 3-NO₂—Ph |
| 54 | N(Me)₂ | CN | 3-OBn—Ph | Ph |
| 55 | N(Me)₂ | CN | 3-OBn—Ph | 3-NO₂—Ph |
| 56 | SMe | CN | 3-pyridyl | 3-OBn—Ph |
| 57 | SMe | CN | 3-pyridyl | 3-OH—Ph |
| 58 | OEt | CN | Ph | Ph |
| 59 | SMe | CN | 3-Br—Ph | 3-NH₂—Ph |
| 60 | N(Me)₂ | CN | 3-OPh—Ph | 3-NH₂—Ph |
| 61 | SMe | CN | 3-OPh—Ph | 3-NH₂—Ph |
| 62 | SMe | CN | 5-Br-3-pyridyl | 3-OBn—Ph |
| 63 | 4-Me-piperidin-1-yl | CN | 3-OPh—Ph | Ph |
| 64 | OH | CN | 4-tolyl | Ph |
| 65 | SMe | CN | 3-OBn—Ph | 3-OH—Ph |
| 66 | SMe | CN | 3-OPh—Ph | 3-OH—Ph |
| 67 | SMe | CN | 3-OH—Ph | 3-OH—Ph |
| 68 | SMe | CN | 3-Br—Ph | 3-OH—Ph |
| 69 | SMe | CN | 3-Br—Ph | 3-OBn—Ph |
| 70 | NHEt | CN | Ph | 3-OH—Ph |
| 71 | SMe | CN | 3-(3-OH—Ph)—Ph | 3-OH—Ph |
| 72 | SMe | CN | 3-(3-OEt—Ph)—Ph | 3-OH—Ph |
| 73 | SMe | CN | 3-(3-pyridyl)-Ph | 3-OH—Ph |
| 74 | SMe | CN | 5-Ph-pyridin-3-yl | 3-OBn—Ph |
| 75 | N(Me)₂ | CN | 5-Br-3-pyridyl | 3-OBn—Ph |
| 76 | N(Me)₂ | CN | 5-Ph-3-pyridyl | 3-OBn—Ph |
| 77 | SMe | CO₂Et | Ph | 3-OH—Ph |
| 78 | SMe | CO₂Et | Ph | Ph |
| 79 | NHEt | CN | Ph | 4-OH—Ph |
| 80 | N(Me)₂ | CN | 5-Ph-pyridin-3-yl | 3-OH—Ph |
| 81 | SMe | CN | 3-(3-NH₂—Ph)—Ph | 3-OH—Ph |
| 82 | SMe | CN | 3-(3-Cl,4-F—Ph)—Ph | 3-OH—Ph |
| 83 | SMe | CN | 3-(4-iPr—Ph)—Ph | 3-OH—Ph |
| 84 | SMe | CN | 5-Ph-pyridin-3-yl | 3-OH—Ph |
| 85 | SMe | CN | 5-Ph-pyridin-3-yl | 3-NO₂—Ph |
| 86 | SMe | CN | 3-(3-N—Boc-pyrrol-2-yl)-Ph | 3-OH—Ph |
| 87 | SMe | CN | 3-(4-iPr—Ph)—Ph | 3-OH—Ph |

TABLE 1-continued

Compounds of Formula IIa

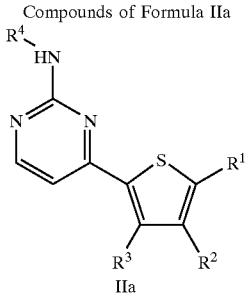

IIa

| No. IIa- | R¹ | R² | R³ | R⁴ |
|---|---|---|---|---|
| 88 | SMe | CN | 3-pyridyl | 3-NHSO₂Me—Ph |
| 89 | SMe | CN | 3-pyridyl | 3-NHSO₂Et—Ph |
| 90 | NHEt | CO₂Et | Ph | 3-OMe—Ph |
| 91 | SMe | CN | 3-pyridyl | 3-SO₂NH₂—Ph |
| 92 | SMe | CN | 3-(2-OH—Ph)—Ph | 3-OH—Ph |
| 93 | SMe | CN | 3-(3-pyrrol-2-yl)-Ph | 3-OH—Ph |
| 94 | SMe | CN | 3-(6-OMe-pyridin-2-yl)-Ph | 3-OH—Ph |
| 95 | SMe | CN | 3-(5-OMe-pyridin-2-yl)-Ph | 3-OH—Ph |
| 96 | SMe | CN | 3-(2,5-Me₂-isoxazol-4-yl)-Ph | 3-OH—Ph |
| 97 | NH(CH₃)₂morpholin-4-yl | CN | Ph | 3-OH—Ph |
| 98 | NH(CH₃)₂morpholin-4-yl | CN | Ph | 3-SO₂NH₂—Ph |
| 99 | NH(CH₃)₂morpholin-4-yl | CN | Ph | 4-OH—Ph |
| 100 | NH(CH₃)₃N(Et)₂ | CN | Ph | 3-OH—Ph |
| 101 | NH(CH₃)₃N(Et)₂ | CN | Ph | 4-OH—Ph |
| 102 | NH(CH₃)₂piperidin-1-yl | CN | Ph | 3-OH—Ph |
| 103 | NH(CH₃)₂piperidin-1-yl | CN | Ph | 3-SO₂NH₂—Ph |
| 104 | NH(CH₃)₂piperidin-1-yl | CN | Ph | 4-OH—Ph |
| 105 | SMe | CN | 3-(pyridin-4-yl)-Ph | 3-OH—Ph |

TABLE 2

Compounds of Formula IIb

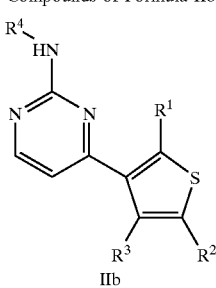

IIb

| No. IIb- | R¹ | R² | R³ | R⁴ |
|---|---|---|---|---|
| 1 | SMe | 4-CH₃thiazol-2-yl | Me | Ph |
| 2 | SMe | 4-CH₃thiazol-2-yl | Me | 4-F—Ph |
| 3 | SMe | 4-CH₃thiazol-2-yl | Me | 6-Cl-pyridin-3-yl |
| 4 | SMe | 4-CH₃thiazol-2-yl | Me | 3-Cl—Ph |
| 5 | SMe | 4-CH₃thiazol-2-yl | Me | 3-CH₃O—Ph |
| 6 | SMe | 4-CH₃thiazol-2-yl | Me | 3-BnO—Ph |

TABLE 2-continued

Compounds of Formula IIb

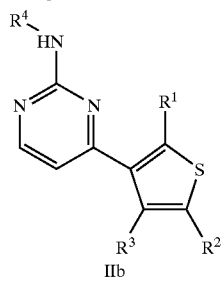

IIb

| No. IIb- | R¹ | R² | R³ | R⁴ |
|---|---|---|---|---|
| 7 | SMe | CN | Me | Ph |
| 8 | SMe | CN | Me | 4-F—Ph |
| 9 | SMe | CN | Me | 6-Cl-pyridin-3-yl |
| 10 | SMe | CN | Me | 3-Cl—Ph |
| 11 | SMe | CN | Me | 3-CH₃O—Ph |
| 12 | SMe | CN | Me | 3-BnO—Ph |

TABLE 7

Compounds of Formula V

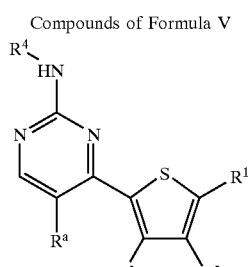

| No.V- | R¹ | Rᵃ | R³ | R⁴ |
|---|---|---|---|---|
| 1 | SCH₂phen-4-ol | Me | 3-Cl phenyl | Ph |
| 2 | OH | Me | Ph | 3-OBn—Ph |
| 3 | OEt | Me | Ph | 3-OBn—Ph |
| 4 | SMe | Me | Ph | 3-OBn—Ph |
| 5 | SMe | Me | Ph | 3-SO₂NH₂—Ph |
| 6 | SMe | Me | Ph | 3-OH—Ph |
| 7 | SMe | Me | Ph | 3-NO₂—Ph |
| 8 | SMe | Me | Ph | 3-NH₂—Ph |
| 9 | SMe | Me | 2-CF₃—Ph | 3-OBn—Ph |
| 10 | SMe | Me | 2-CF₃—Ph | 3-OH—Ph |
| 11 | SCH₂phen-4-ol | Me | 3-Cl—Ph | Ph |
| 12 | SMe | Me | 4-Me—Ph | 3-OBn—Ph |
| 13 | SMe | Me | 4-Me—Ph | 3-OH—Ph |
| 14 | SMe | Me | 4-Me—Ph | pyrid-3-yl |
| 15 | SMe | Me | pyrid-3-yl | 3-OBn—Ph |
| 16 | SMe | Me | pyrid-3-yl | Ph |
| 17 | SMe | Me | pyrid-3-yl | 3-OMe—Ph |
| 18 | SMe | Me | pyrid-3-yl | 3,5-OMe—Ph |
| 19 | SMe | Me | pyrid-3-yl | 3-Br—Ph |
| 20 | SMe | Me | pyrid-3-yl | 3-Cl—Ph |
| 21 | SMe | Me | pyrid-3-yl | 3-CO₂Me—Ph |
| 22 | SMe | Me | pyrid-3-yl | 6-Cl-pyrid-3-yl |
| 23 | SMe | Me | pyrid-3-yl | CH₂Ph |
| 24 | SMe | Me | pyrid-3-yl | 3-OH—Ph |
| 25 | SMe | Me | furan-2-yl | pyrid-3-yl |
| 26 | SMe | Me | furan-2-yl | 3-OH—Ph |
| 27 | SMe | Me | furan-2-yl | 3-OBn—Ph |
| 28 | SMe | Me | furan-2-yl | 3-NO₂—Ph |
| 29 | N(Me)₂ | Me | 3-OPh—Ph | 3-NO₂—Ph |
| 30 | N(Me)₂ | Me | 3-OPh—Ph | 3-OH—Ph |
| 31 | SMe | Me | 3-Ph—Ph | 3-OBn—Ph |
| 32 | SMe | Me | 3-Ph—Ph | 3-OH—Ph |

TABLE 8

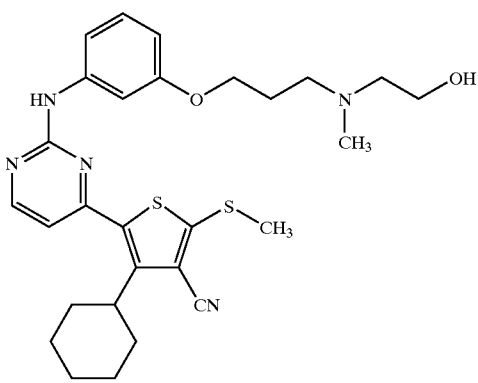

VI-1

TABLE 8-continued

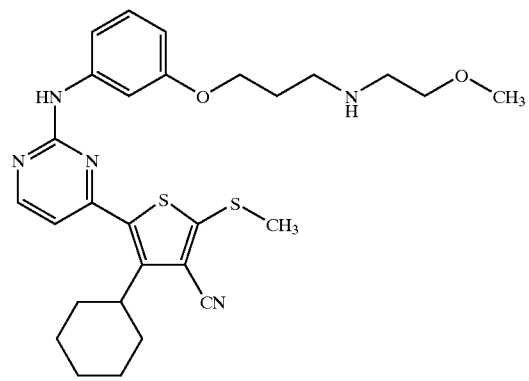

VI-2

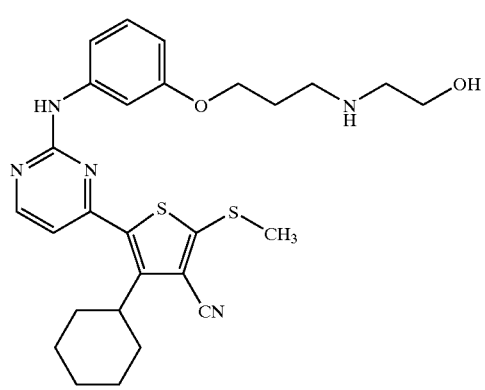

VI-3

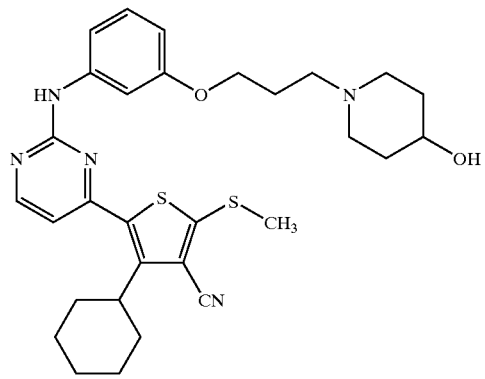

VI-4

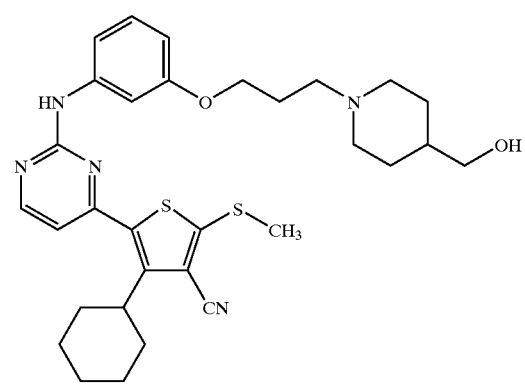

VI-5

TABLE 8-continued
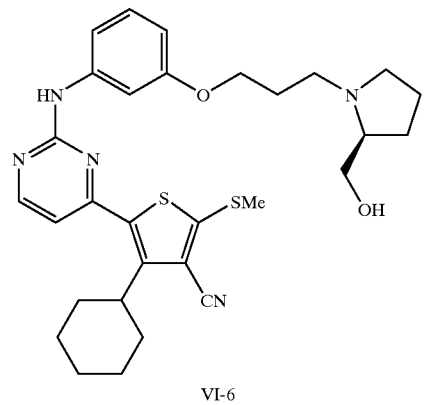
VI-6
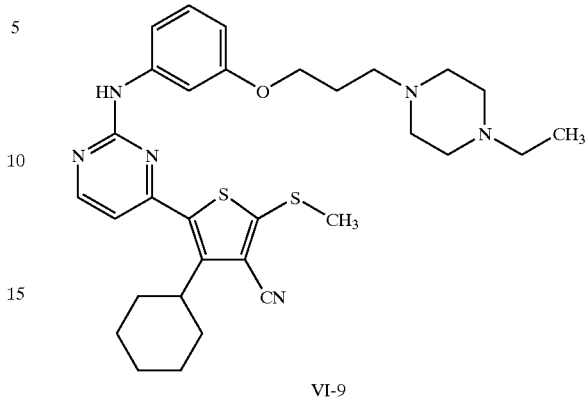
VI-9
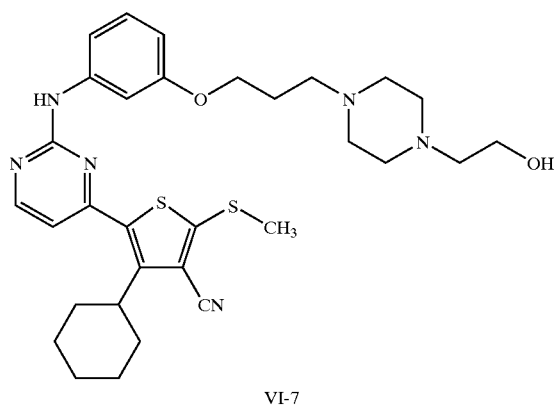
VI-7
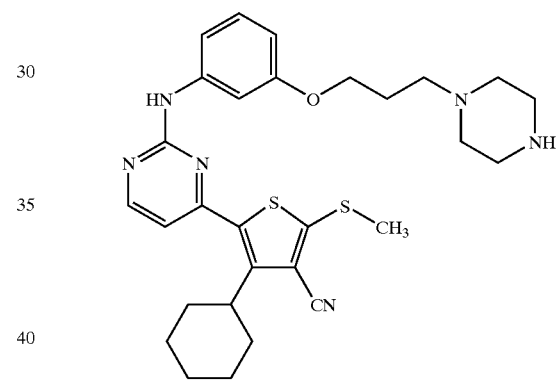
VI-10
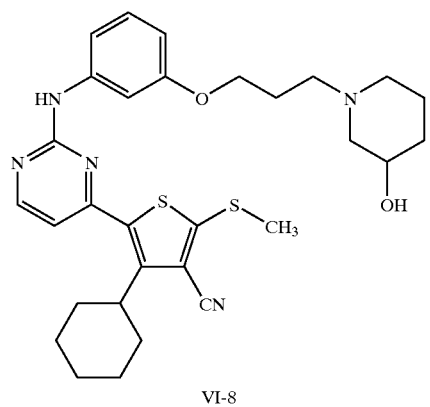
VI-8
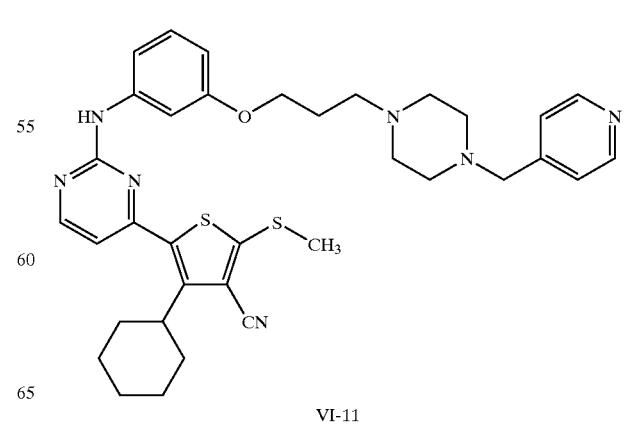
VI-11

TABLE 8-continued
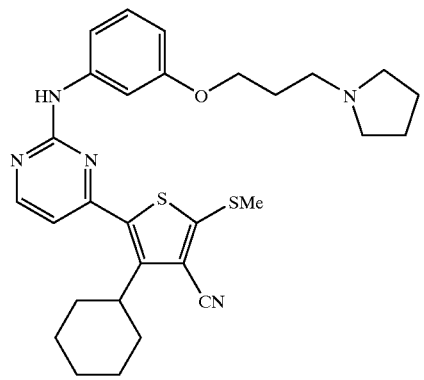
VI-12
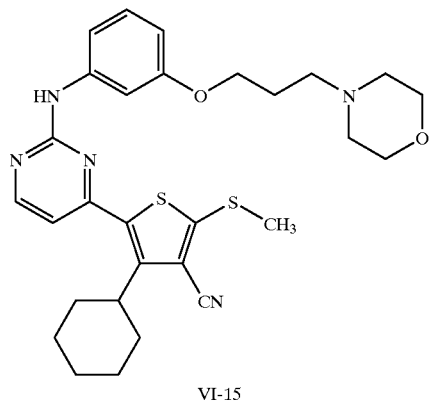
VI-15
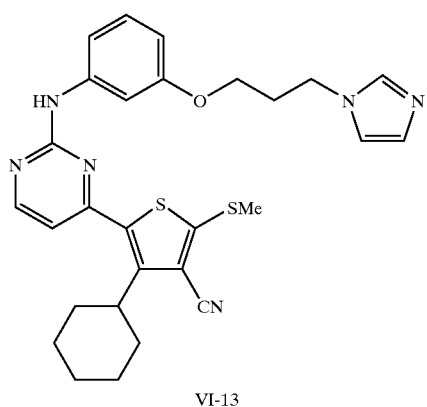
VI-13
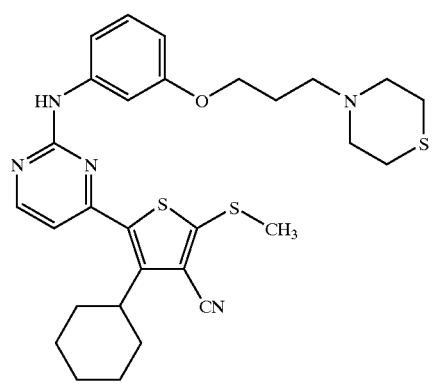
VI-16
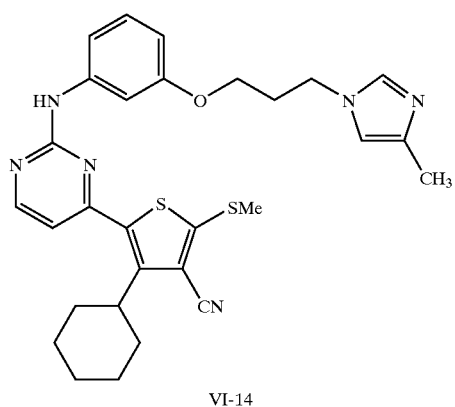
VI-14
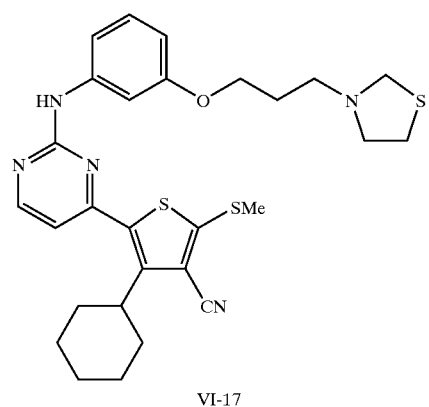
VI-17

TABLE 8-continued
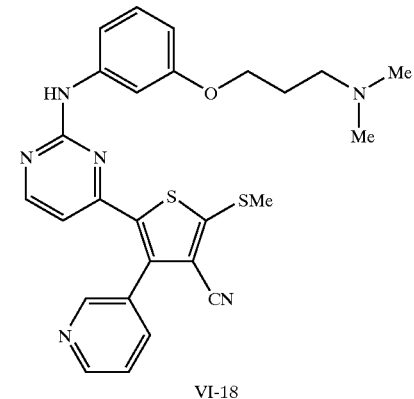
VI-18
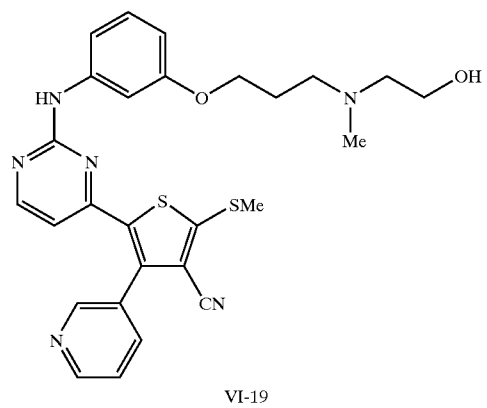
VI-19
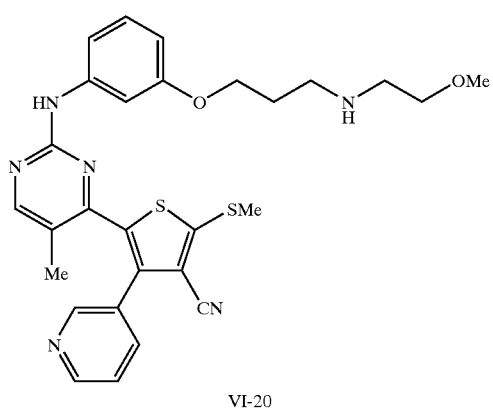
VI-20
TABLE 8-continued
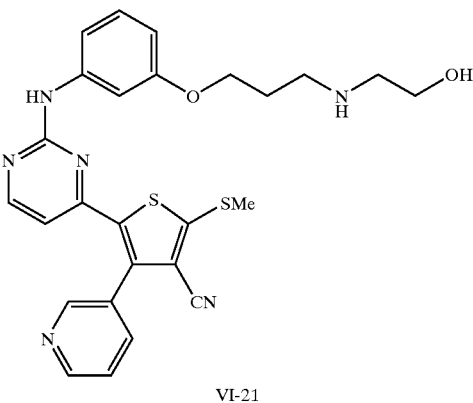
VI-21
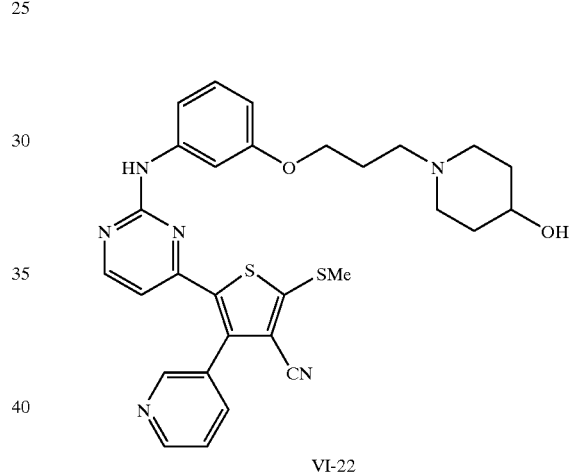
VI-22
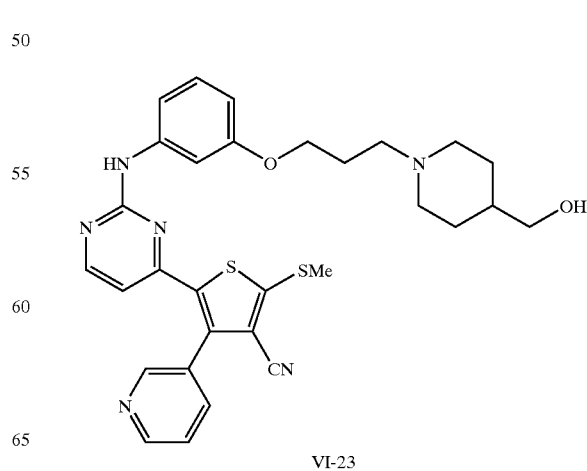
VI-23

TABLE 8-continued
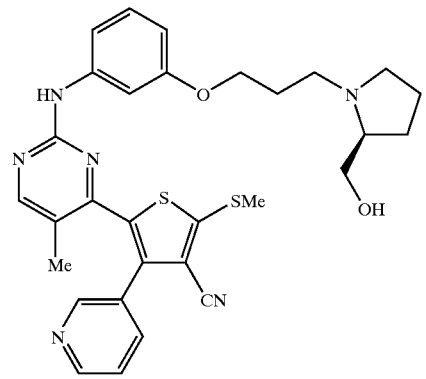
VI-24
TABLE 8-continued
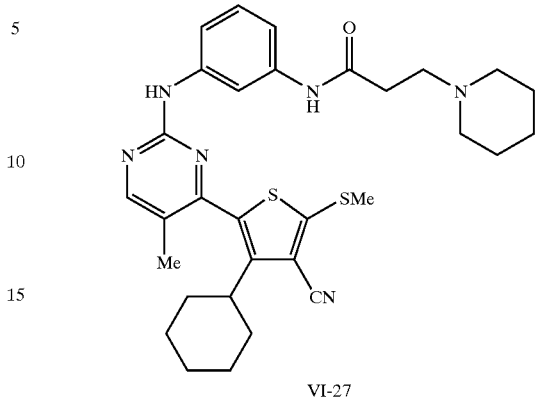
VI-27
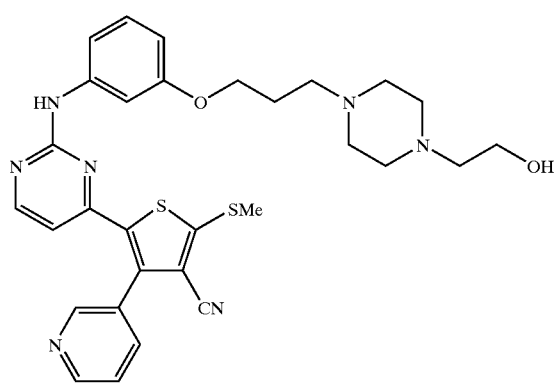
VI-25
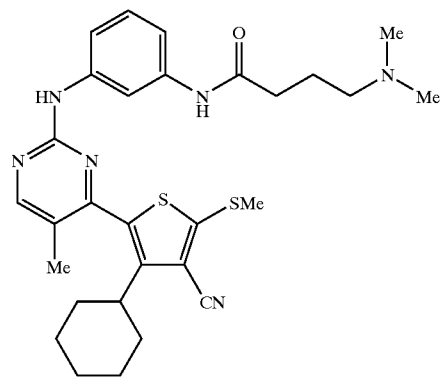
VI-28
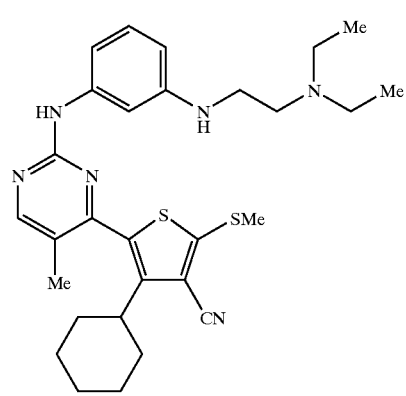
VI-26
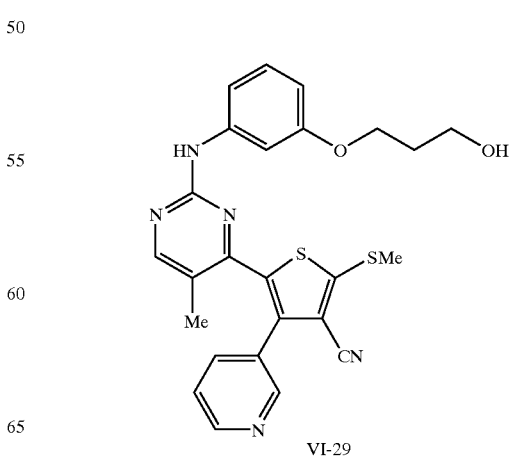
VI-29

TABLE 8-continued
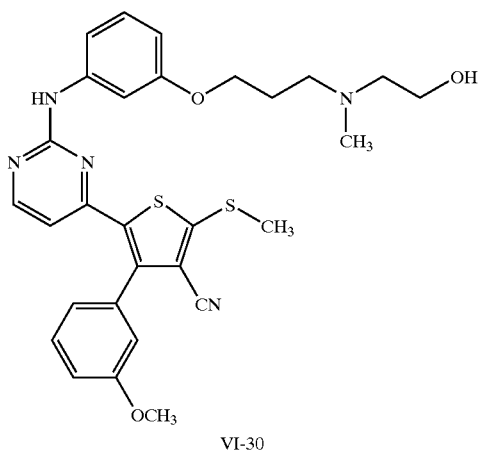
VI-30
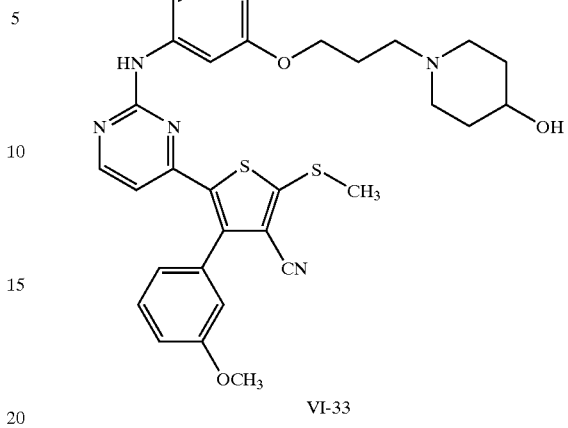
VI-33
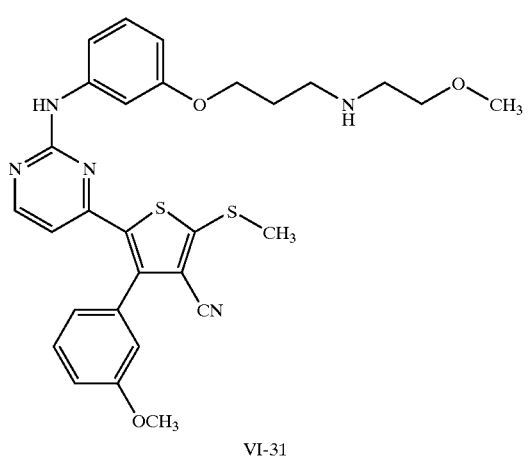
VI-31
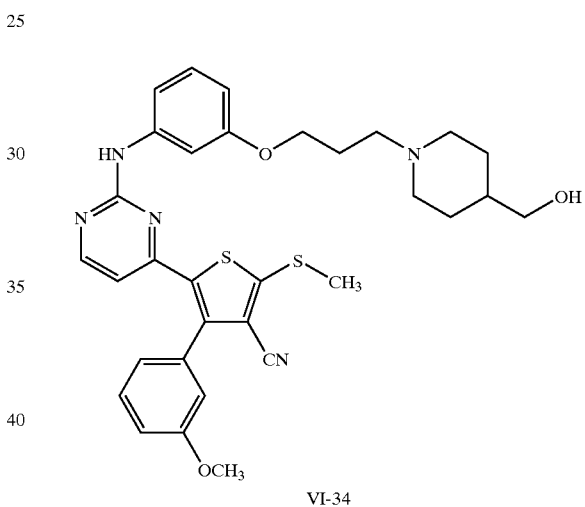
VI-34
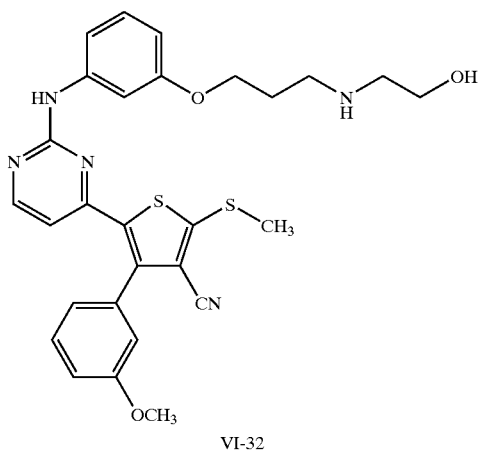
VI-32
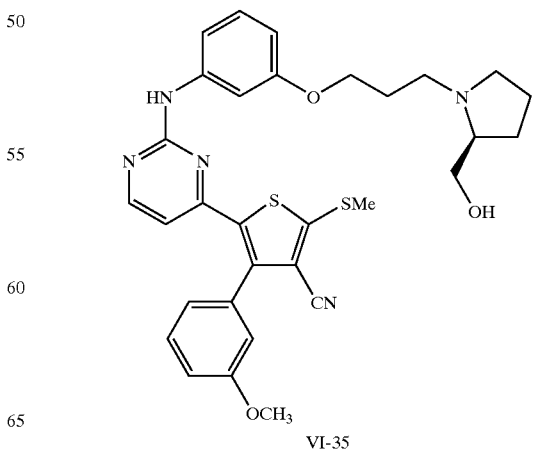
VI-35

TABLE 8-continued
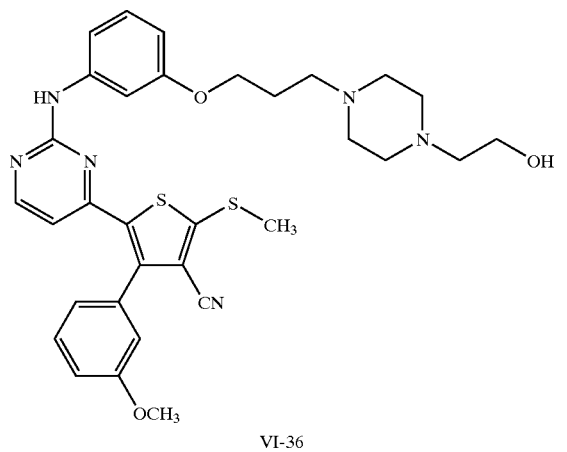
VI-36
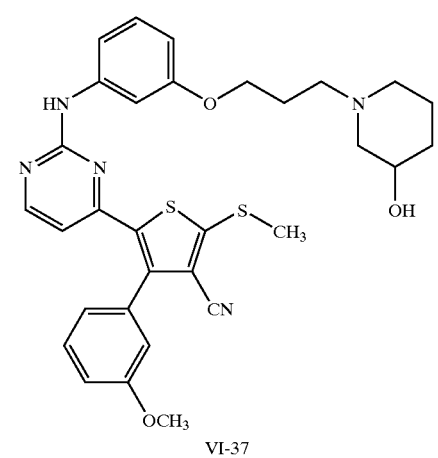
VI-37
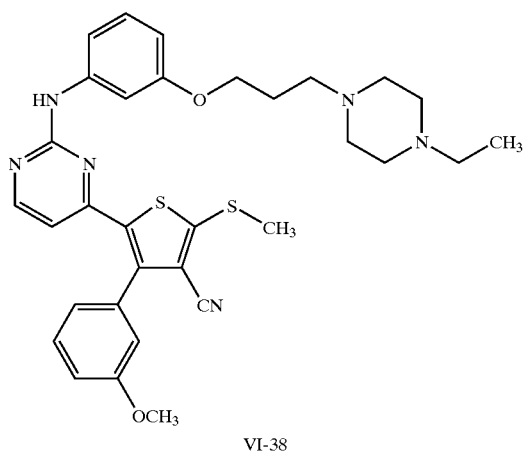
VI-38
TABLE 8-continued
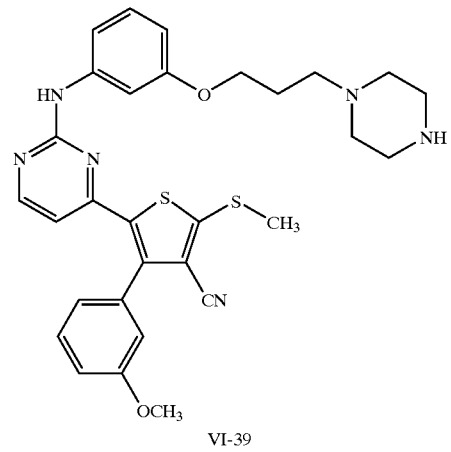
VI-39
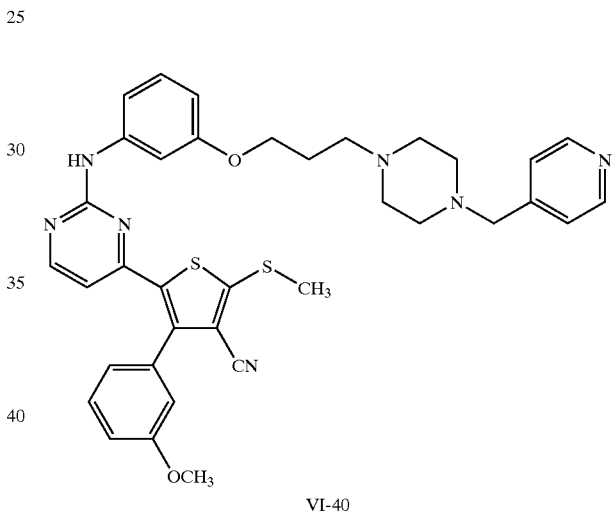
VI-40
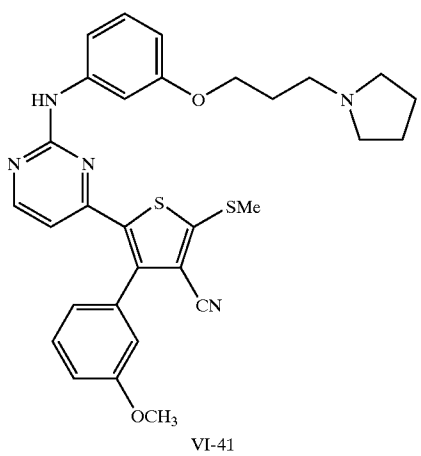
VI-41

TABLE 8-continued
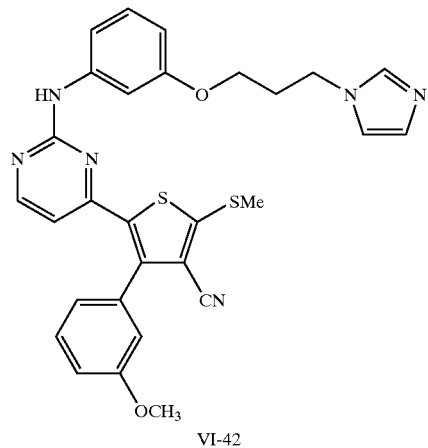
VI-42
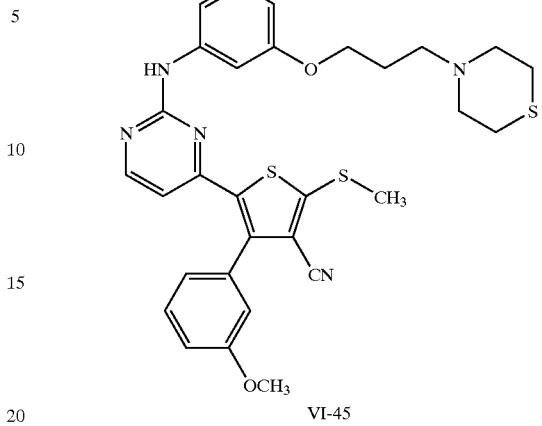
VI-45
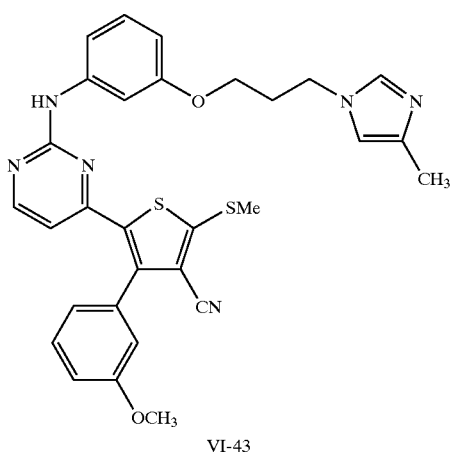
VI-43
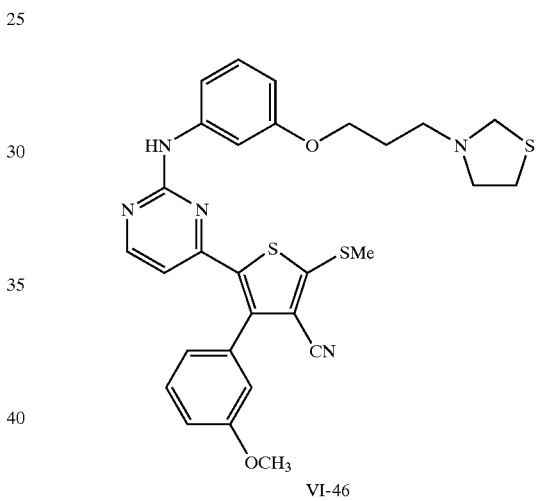
VI-46
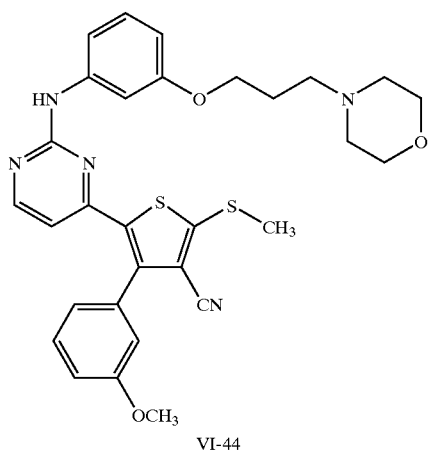
VI-44
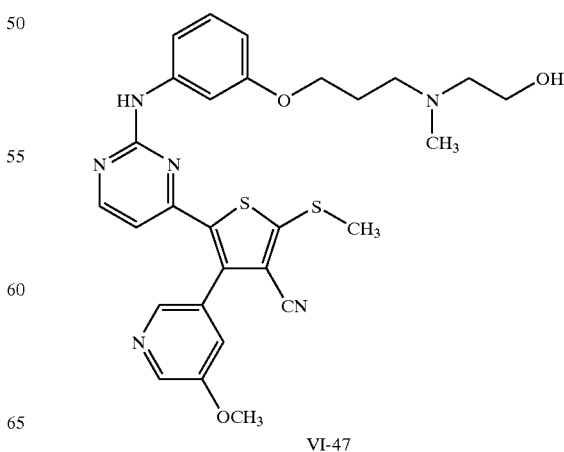
VI-47

TABLE 8-continued
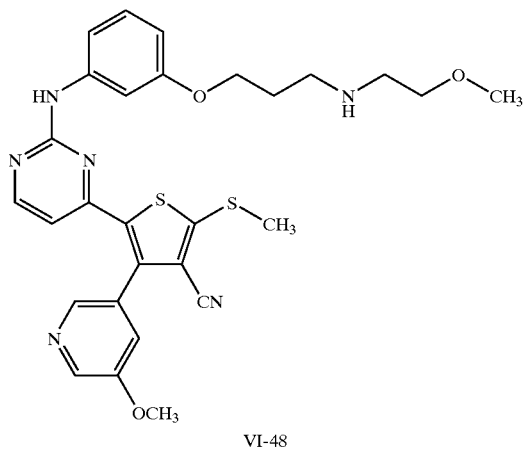
VI-48
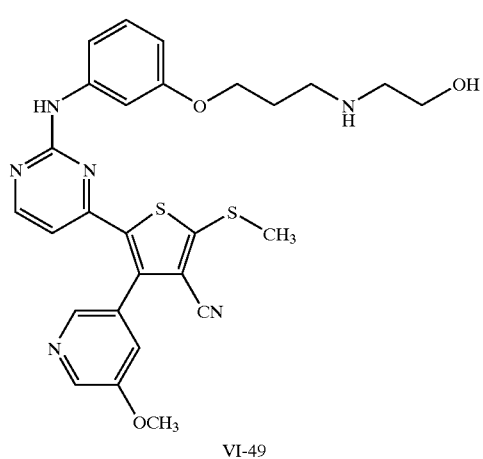
VI-49
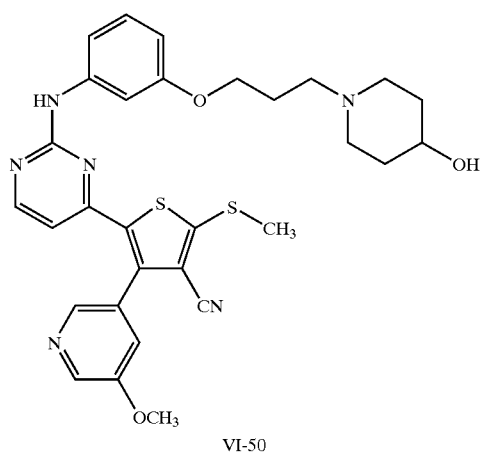
VI-50
TABLE 8-continued
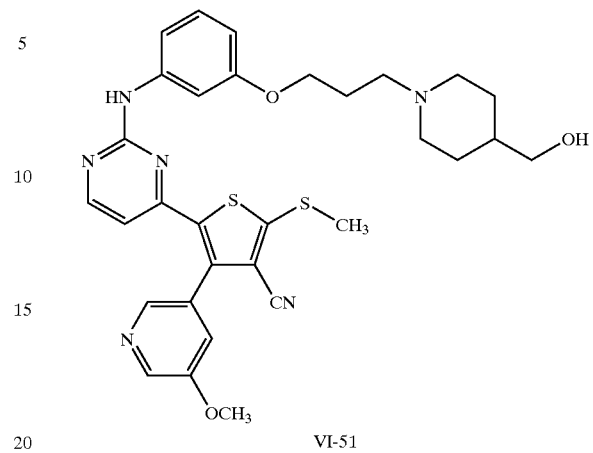
VI-51
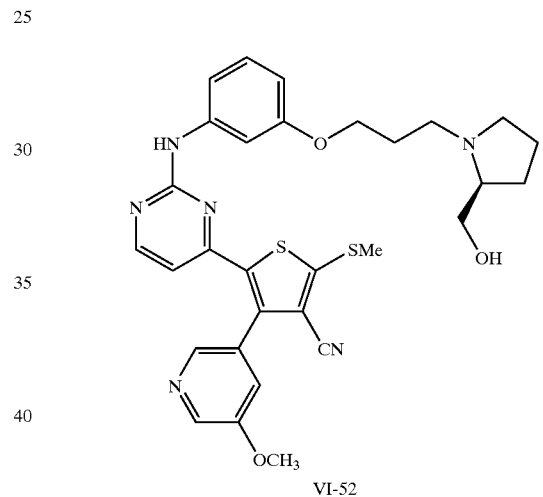
VI-52
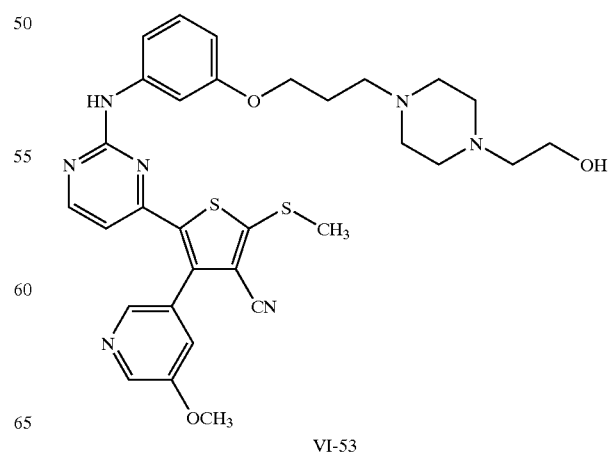
VI-53

TABLE 8-continued
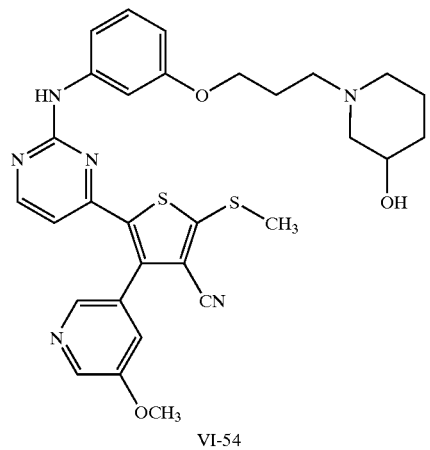
VI-54
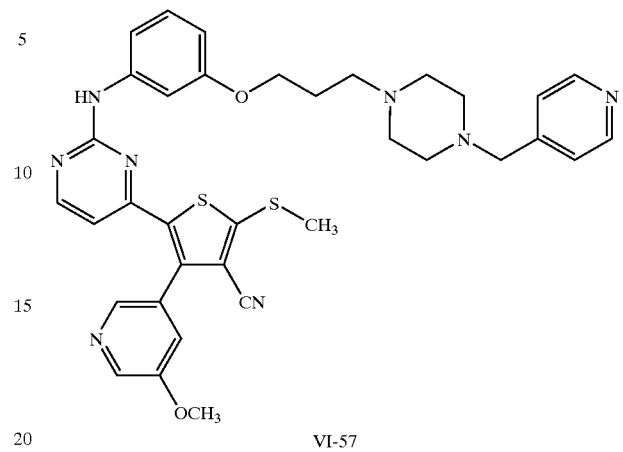
VI-57
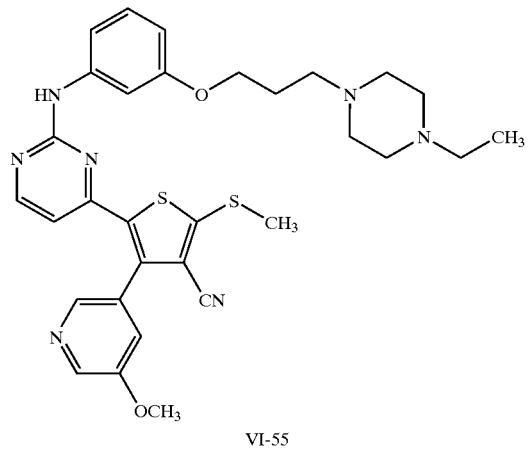
VI-55
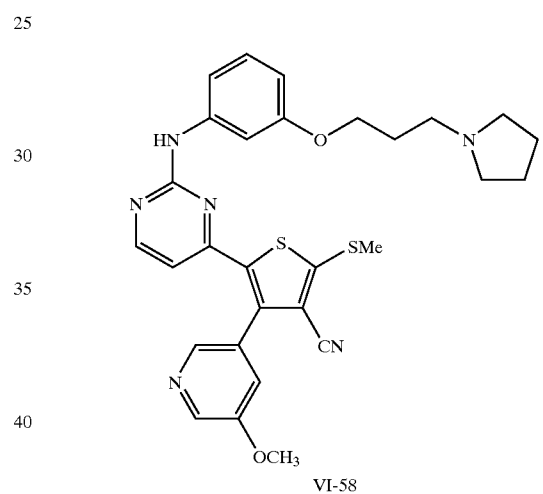
VI-58
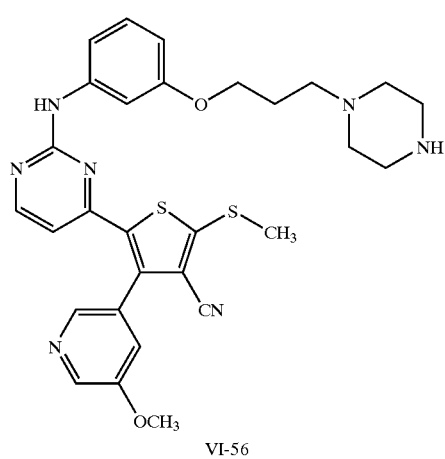
VI-56
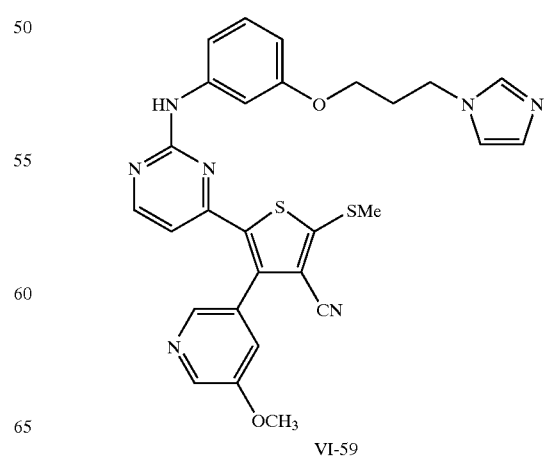
VI-59

TABLE 8-continued
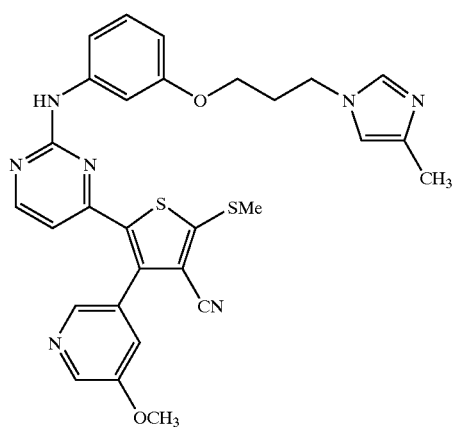
VI-60
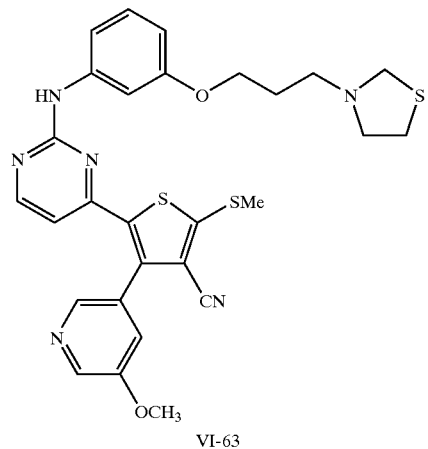
VI-63
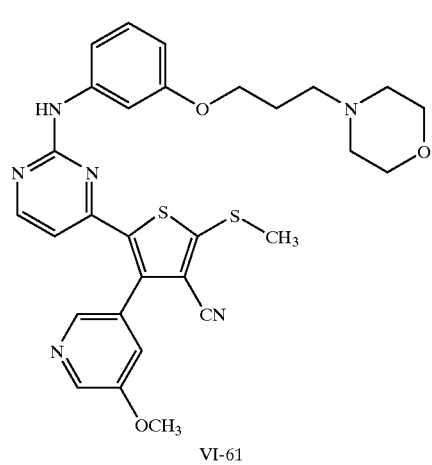
VI-61
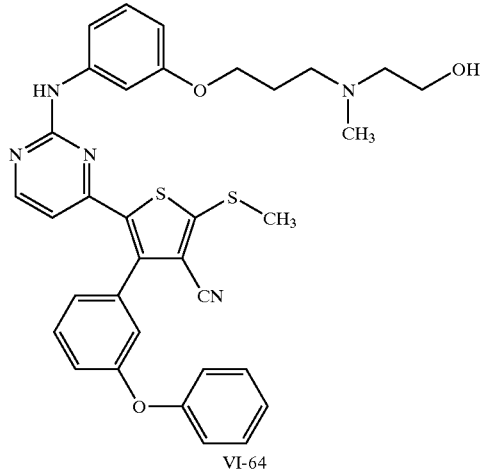
VI-64
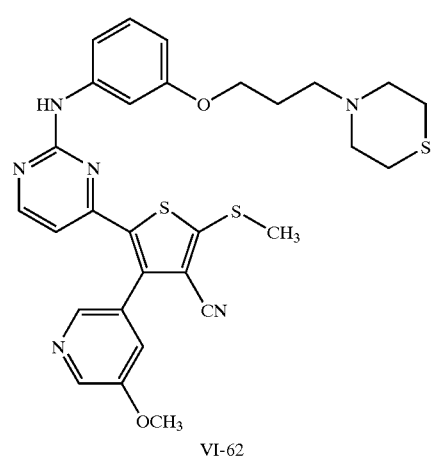
VI-62
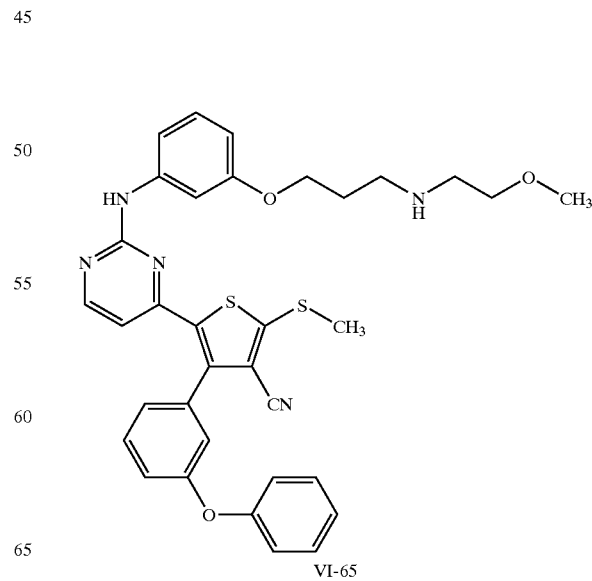
VI-65

TABLE 8-continued
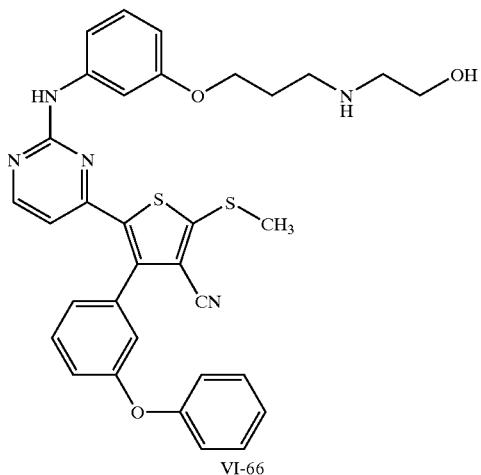
VI-66
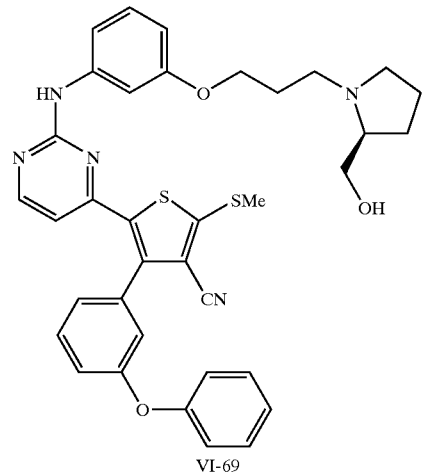
VI-69
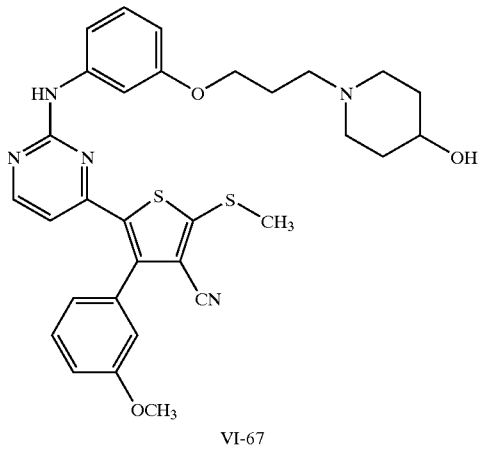
VI-67
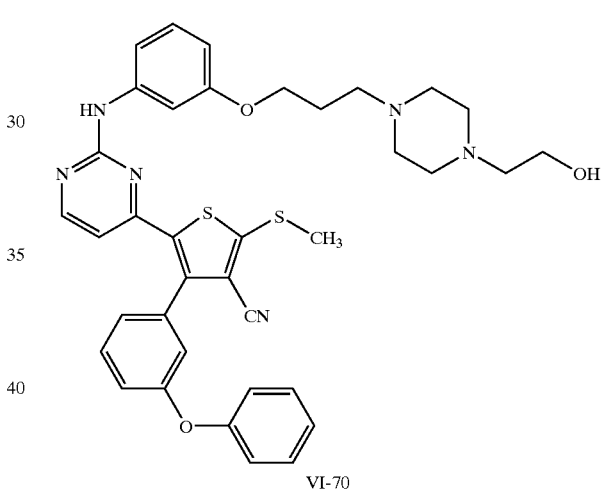
VI-70
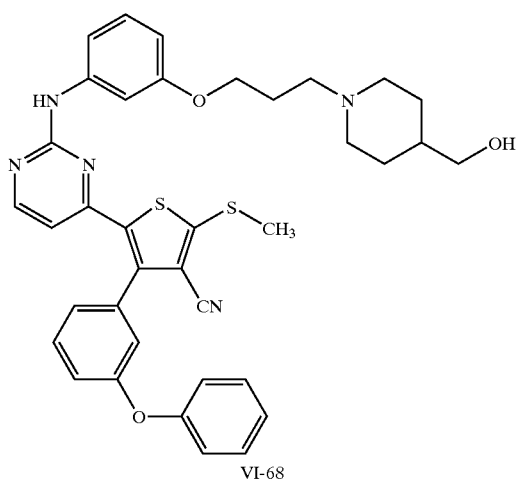
VI-68
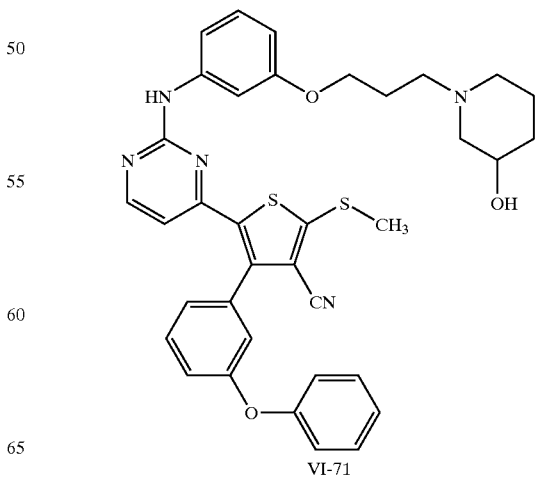
VI-71

TABLE 8-continued
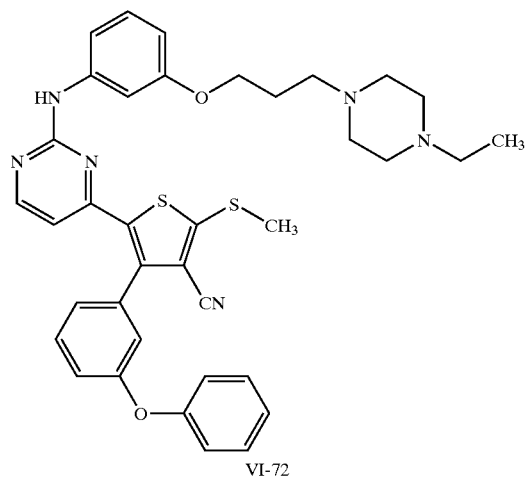
VI-72
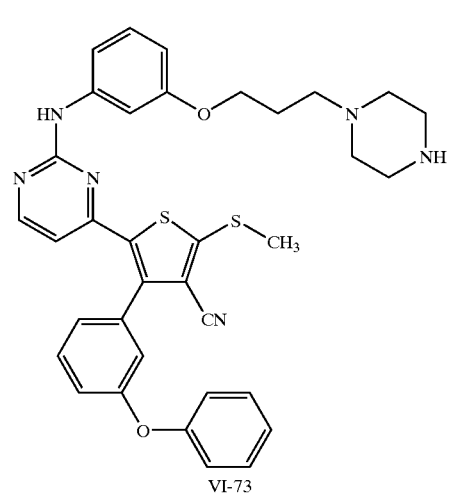
VI-73
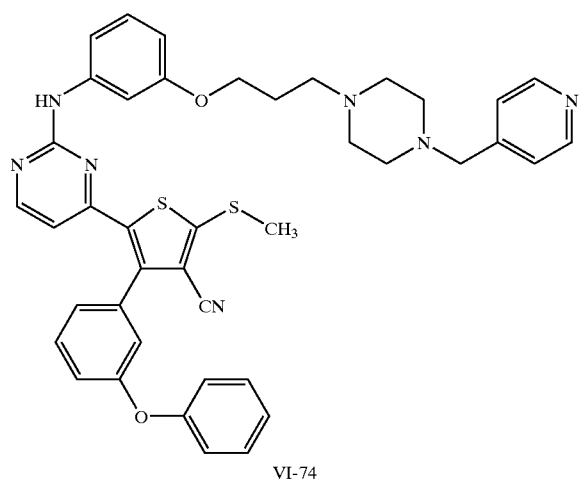
VI-74
TABLE 8-continued
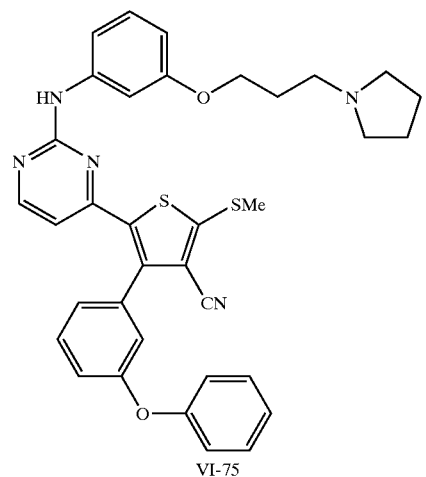
VI-75
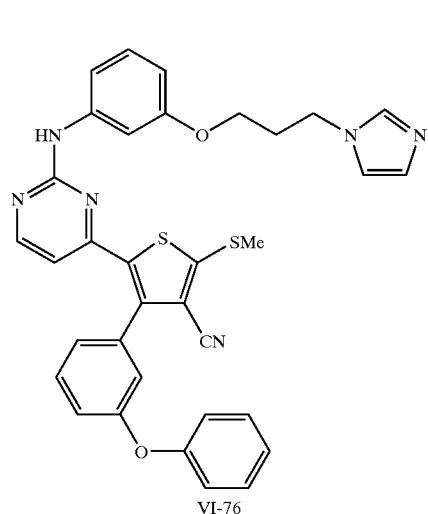
VI-76
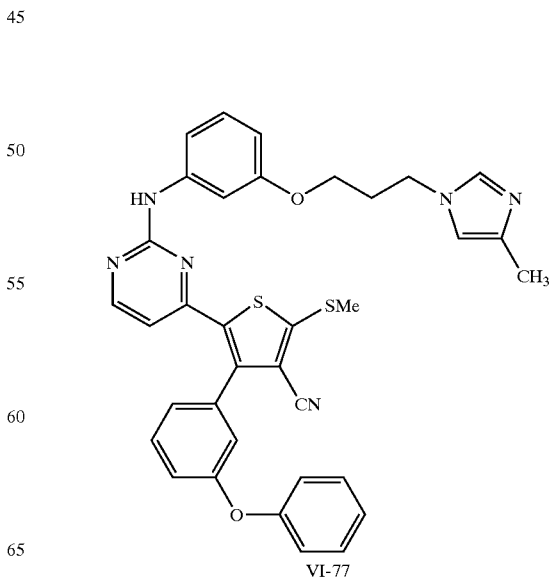
VI-77

TABLE 8-continued
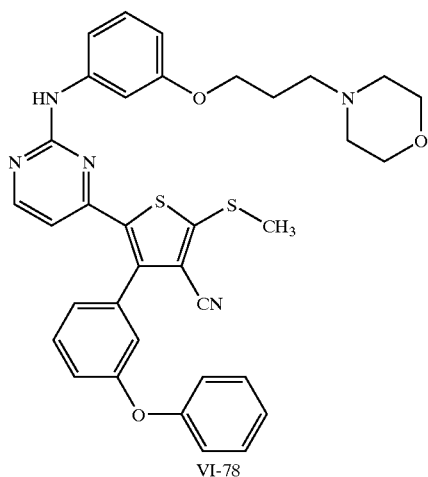
VI-78
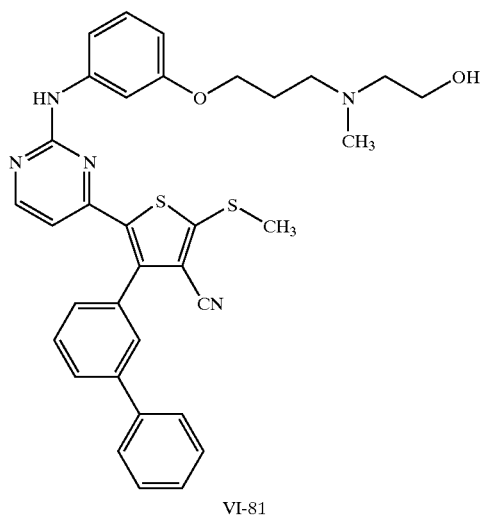
VI-81
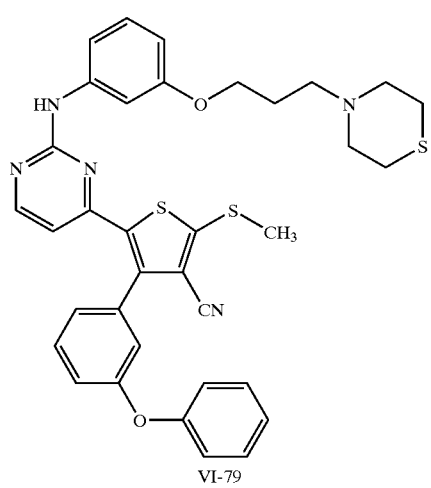
VI-79
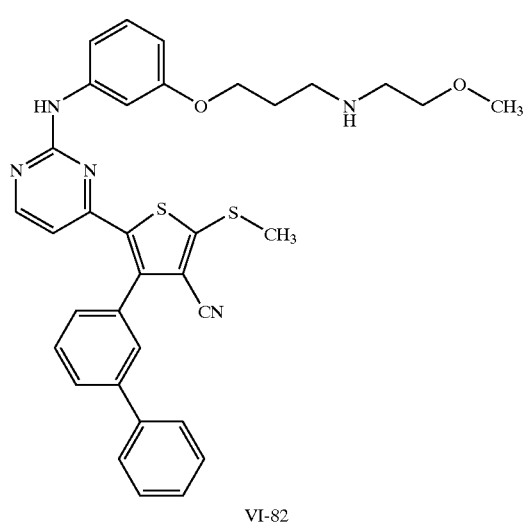
VI-82
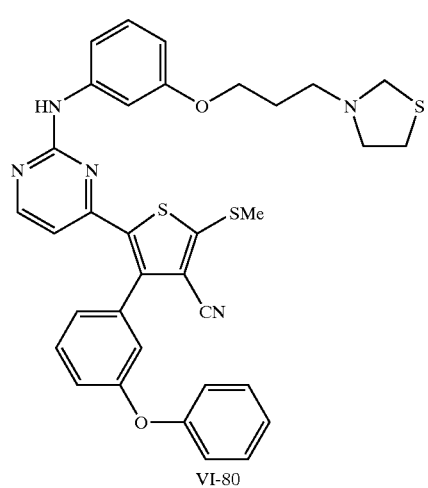
VI-80
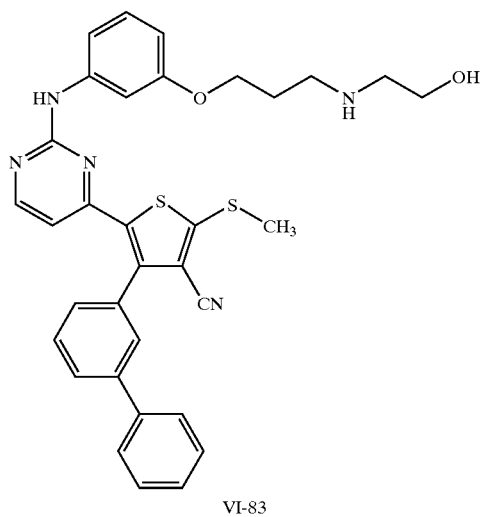
VI-83

TABLE 8-continued
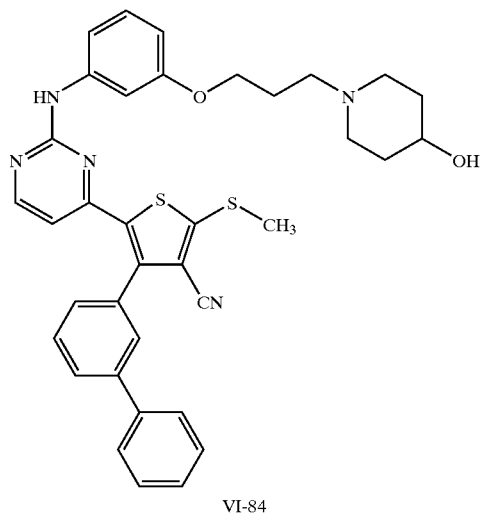
VI-84
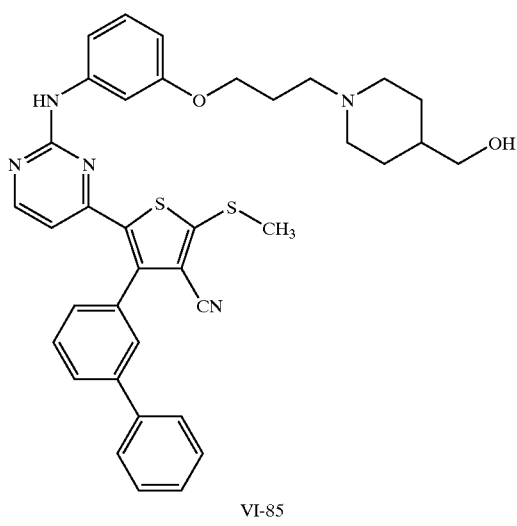
VI-85
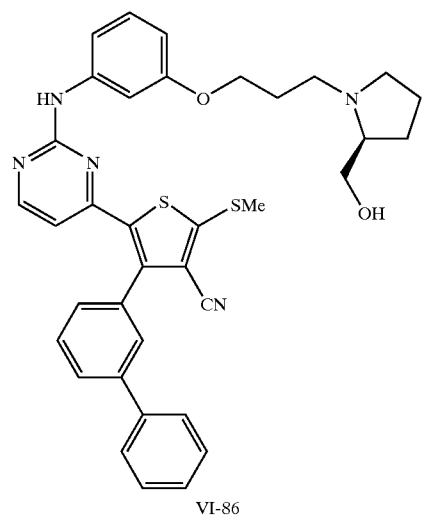
VI-86
TABLE 8-continued
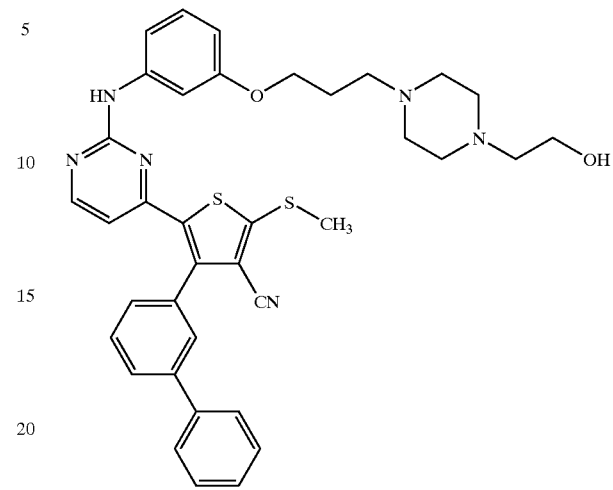
VI-87
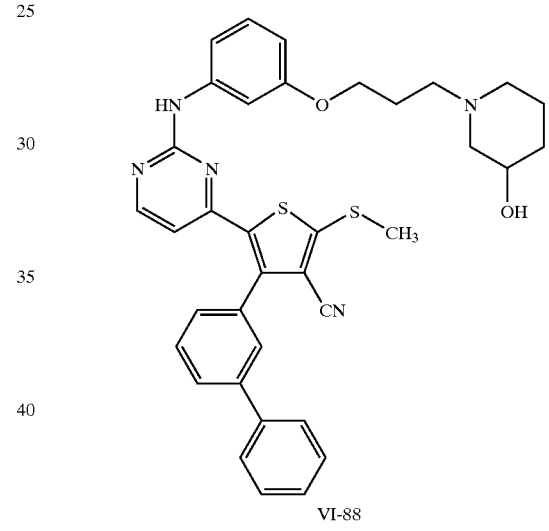
VI-88
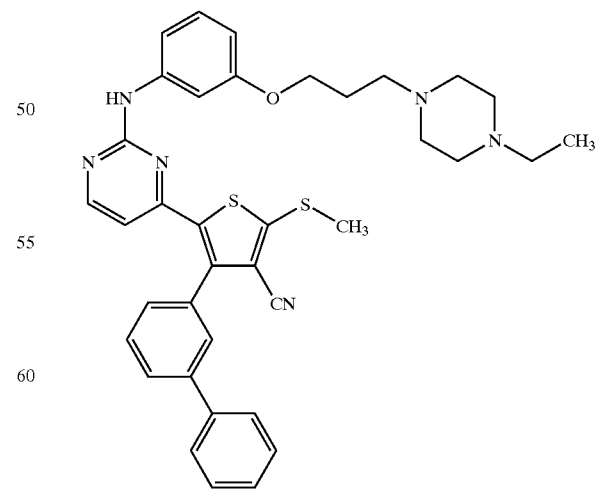
VI-89

TABLE 8-continued
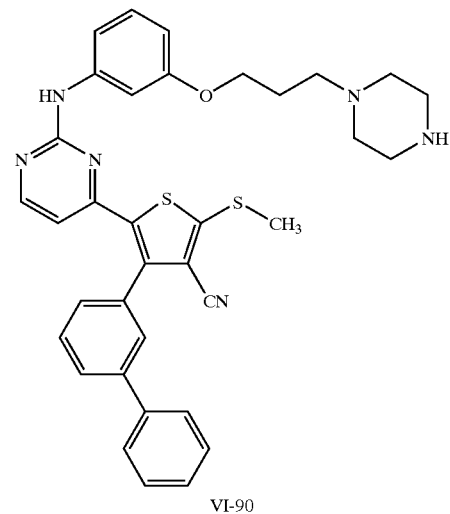
VI-90
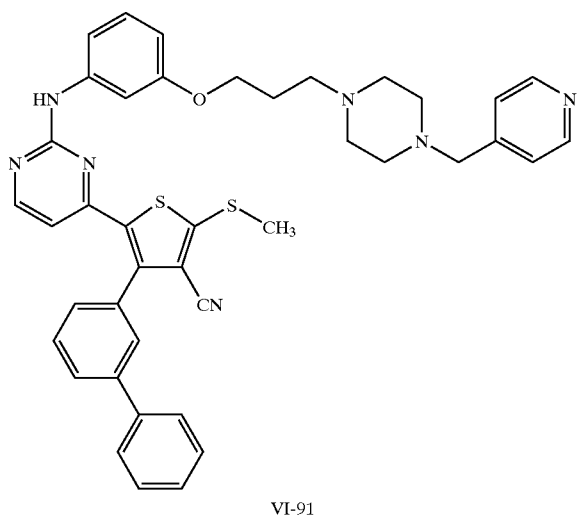
VI-91
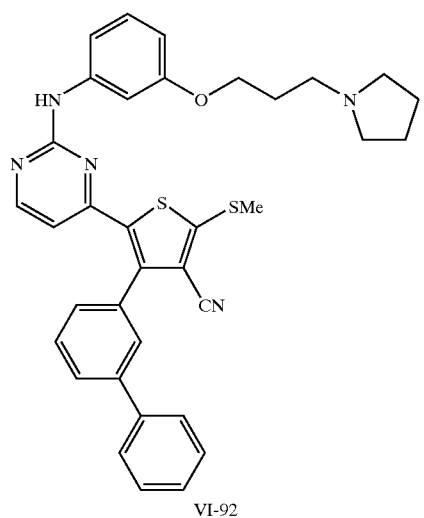
VI-92
TABLE 8-continued
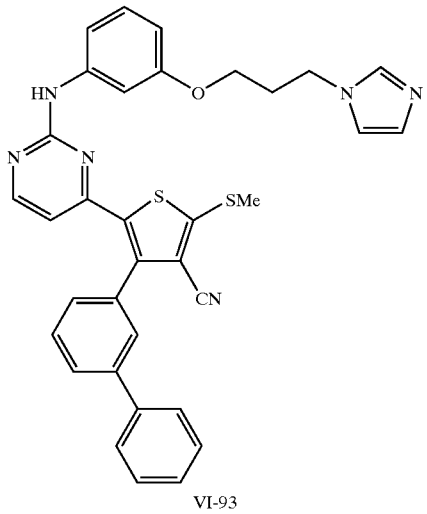
VI-93
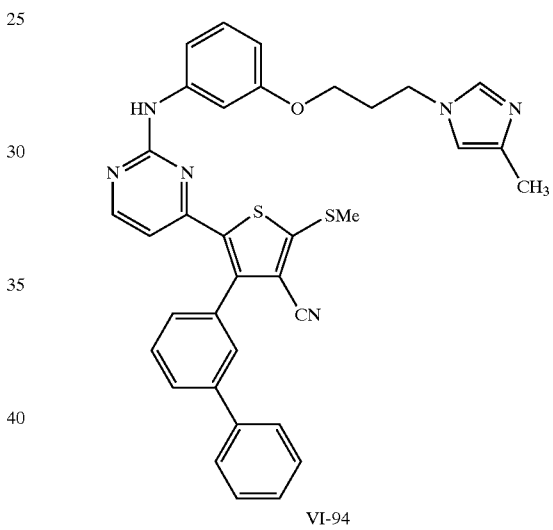
VI-94
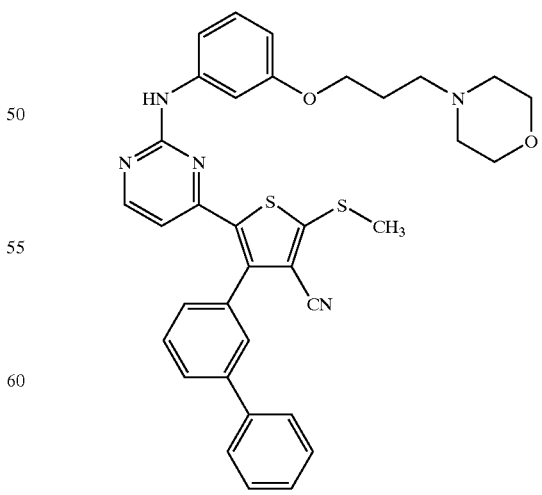
VI-95

TABLE 8-continued
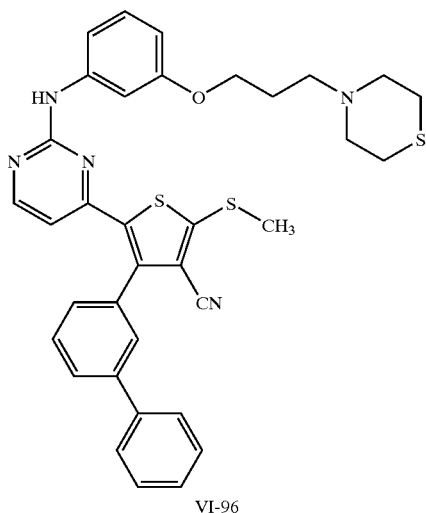
VI-96
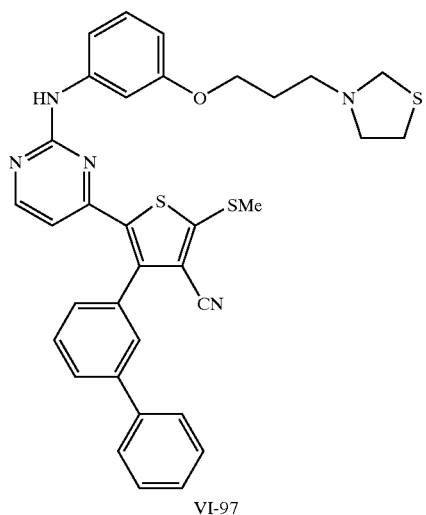
VI-97
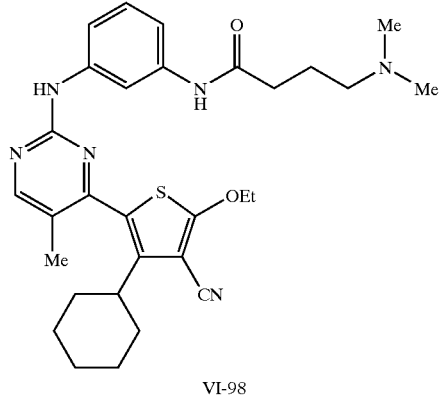
VI-98
TABLE 8-continued
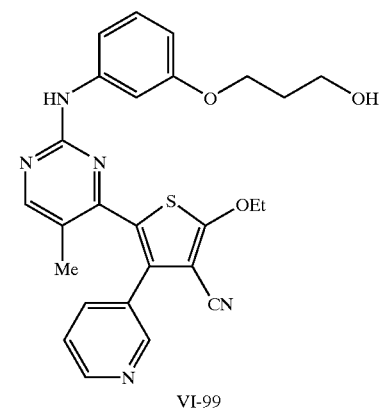
VI-99
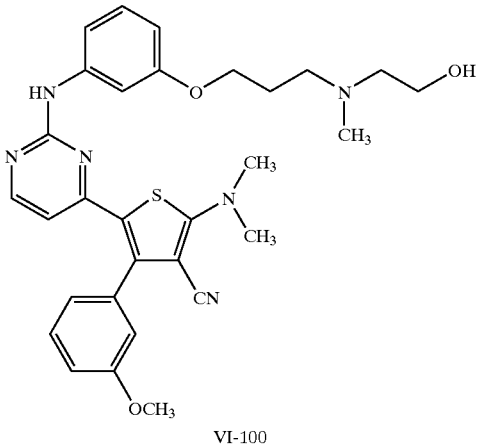
VI-100
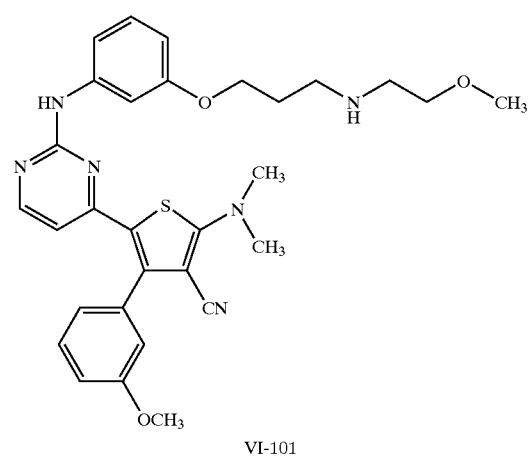
VI-101

TABLE 8-continued
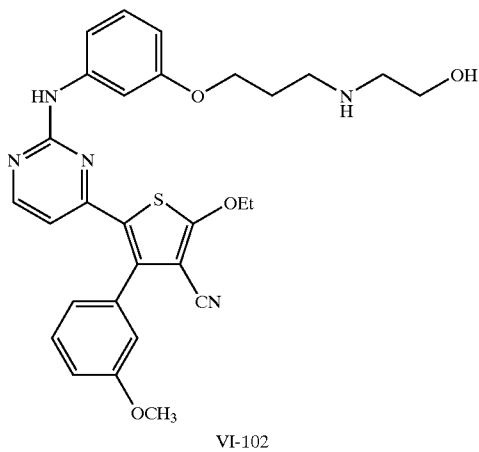
VI-102
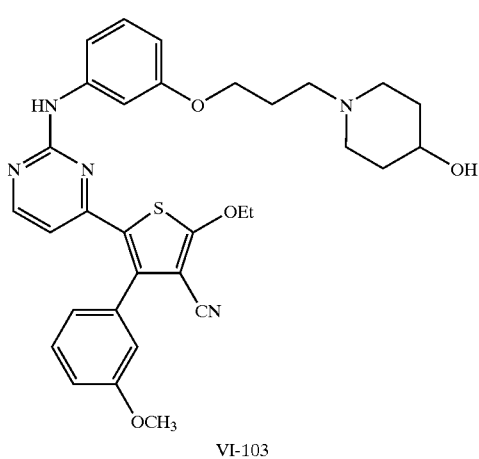
VI-103
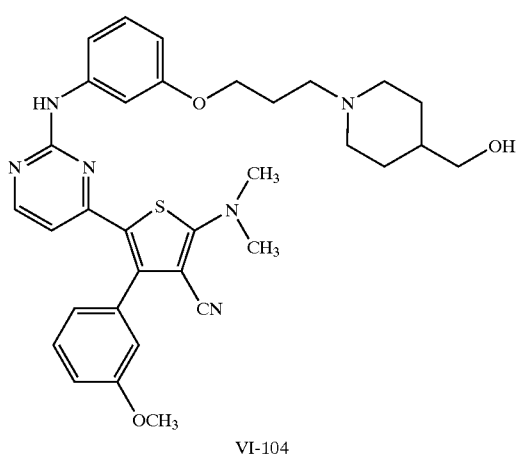
VI-104
TABLE 8-continued
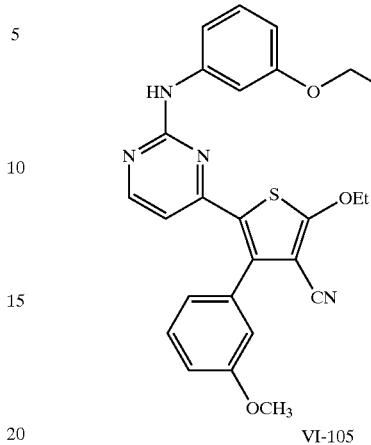
VI-105
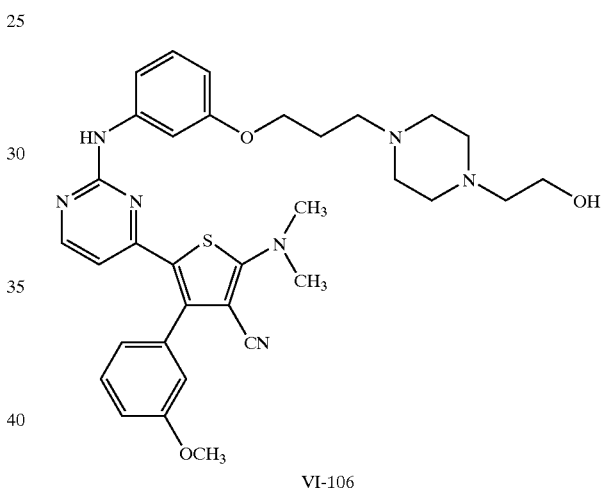
VI-106
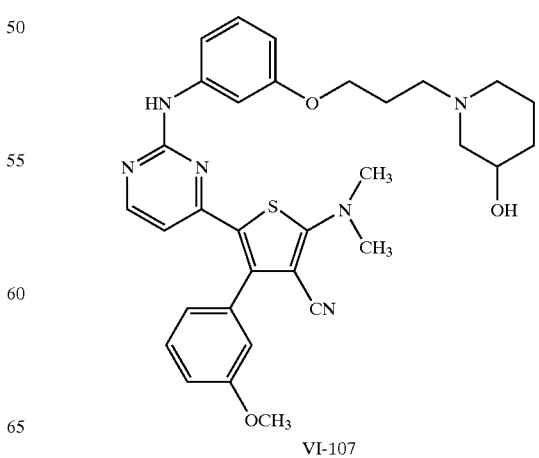
VI-107

TABLE 8-continued
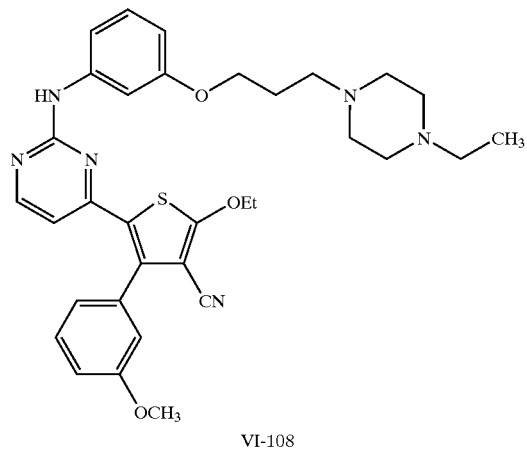
VI-108
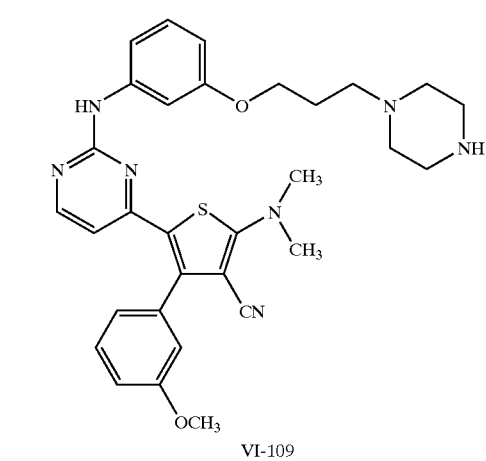
VI-109
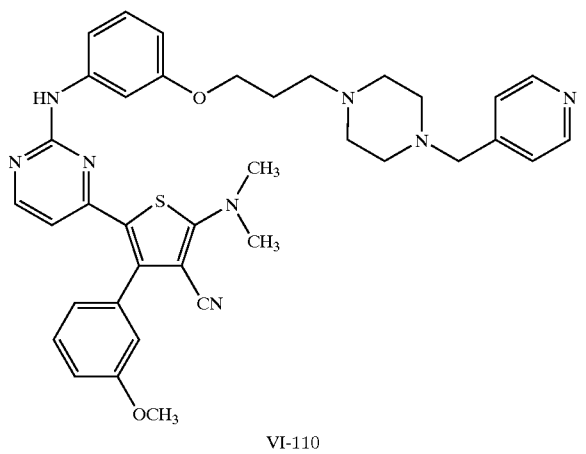
VI-110
TABLE 8-continued
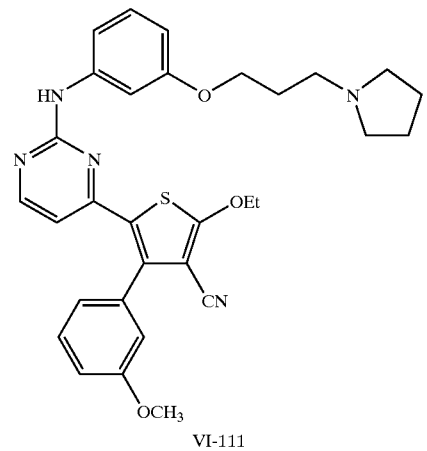
VI-111
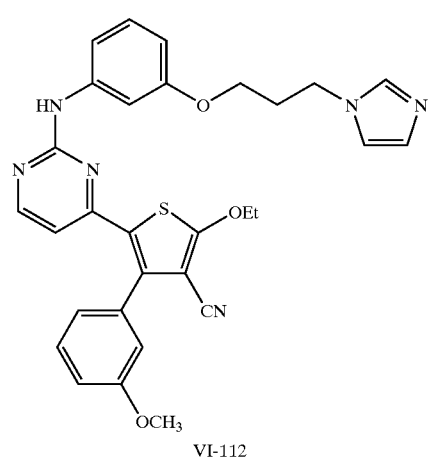
VI-112
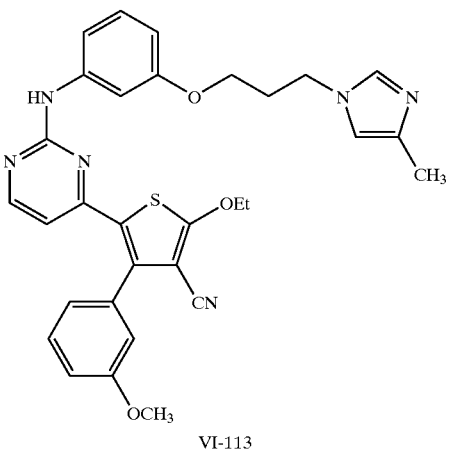
VI-113

TABLE 8-continued
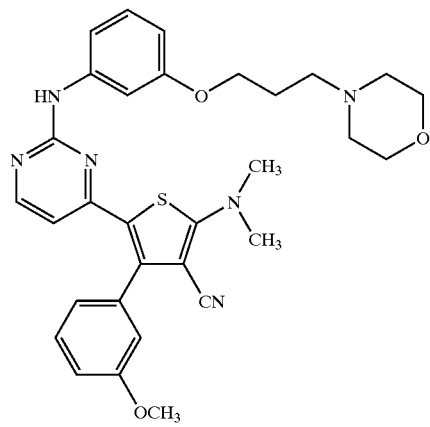
VI-114
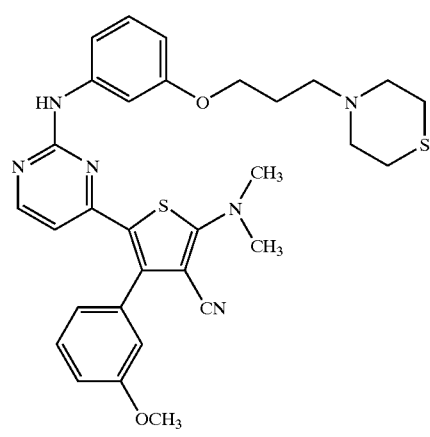
VI-115
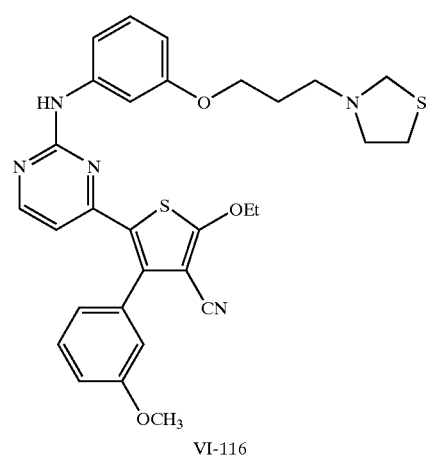
VI-116
TABLE 8-continued
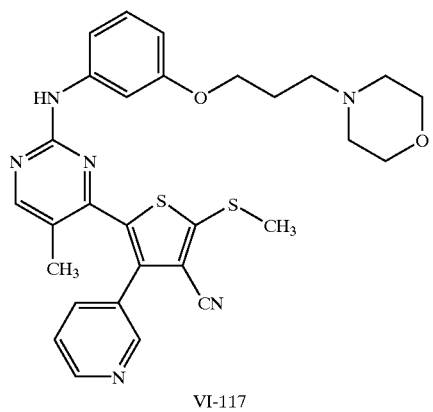
VI-117
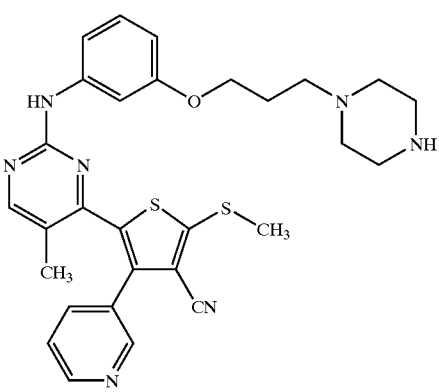
VI-118
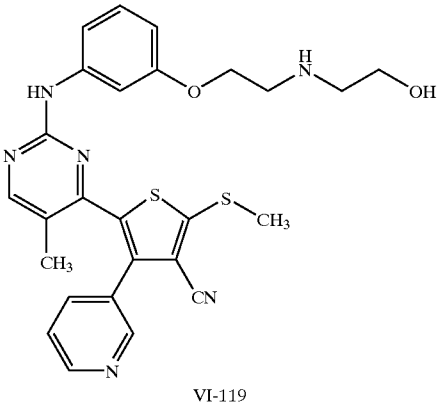
VI-119

TABLE 8-continued
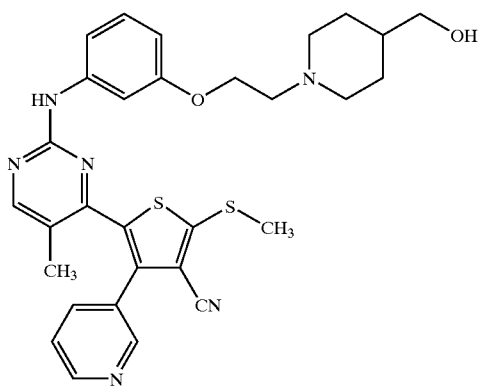
VI-120
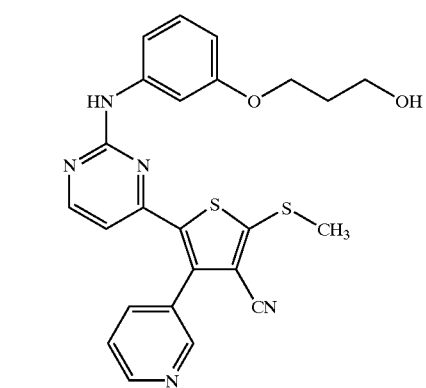
VI-121
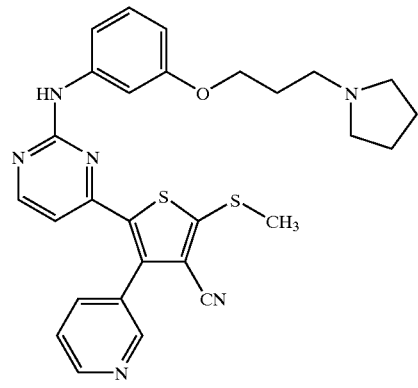
VI-122
TABLE 8-continued
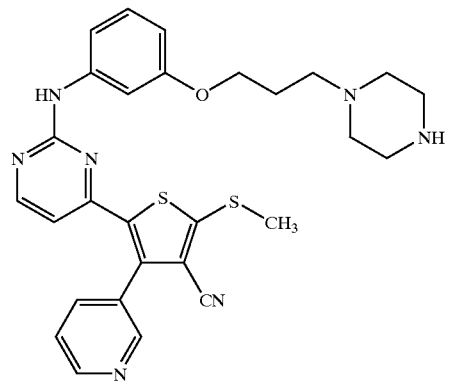
VI-123
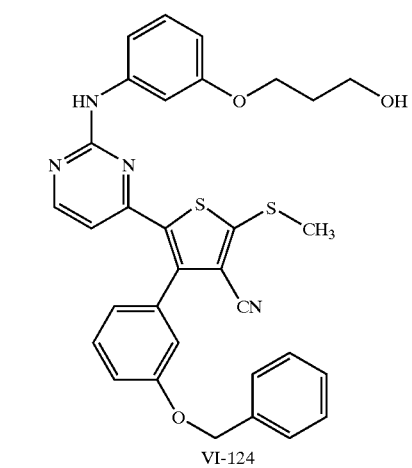
VI-124
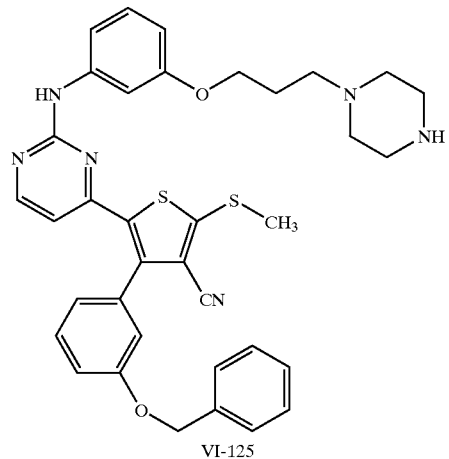
VI-125

TABLE 8-continued
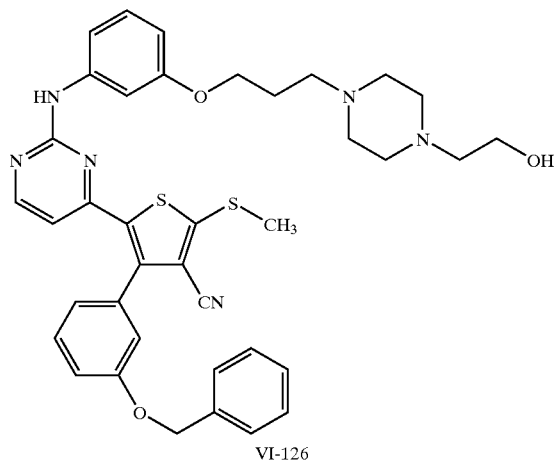
VI-126
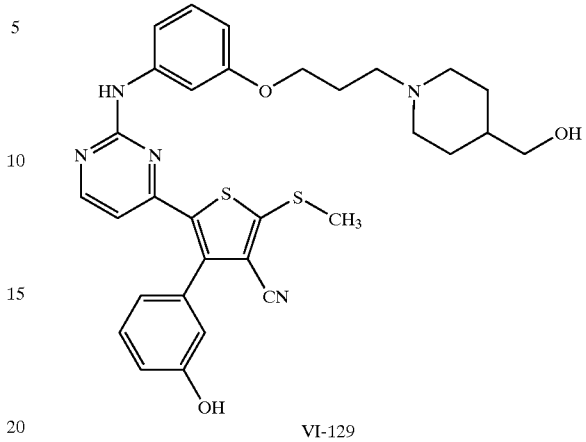
VI-129
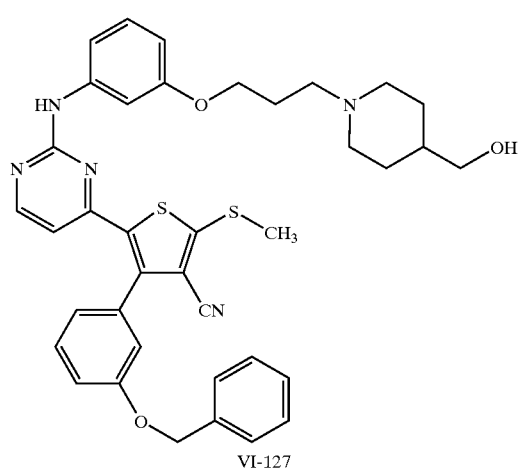
VI-127
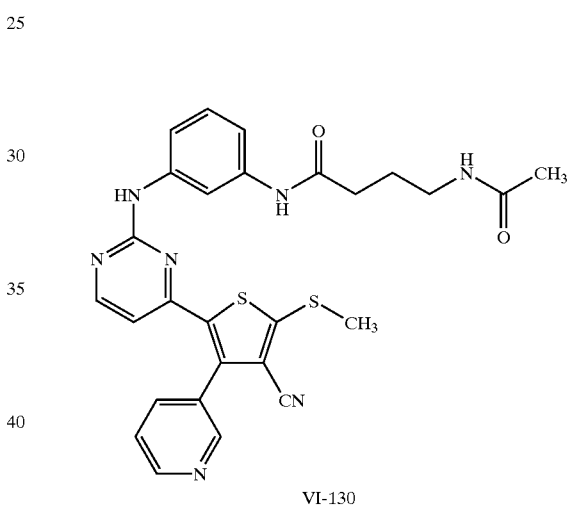
VI-130
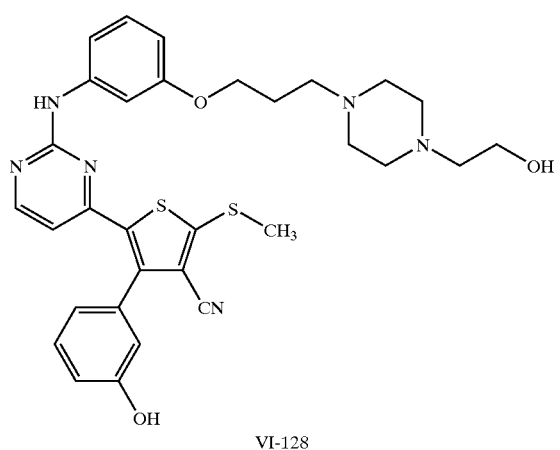
VI-128
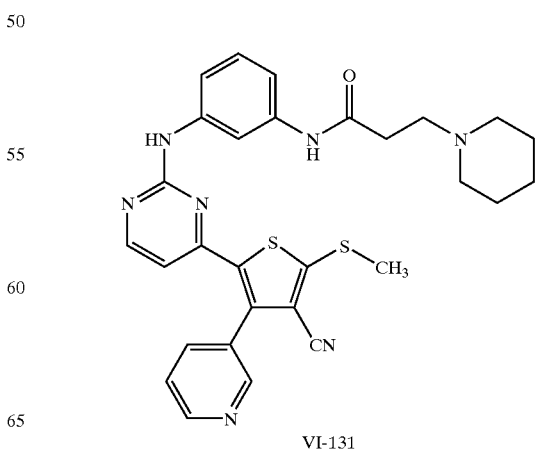
VI-131

TABLE 8-continued
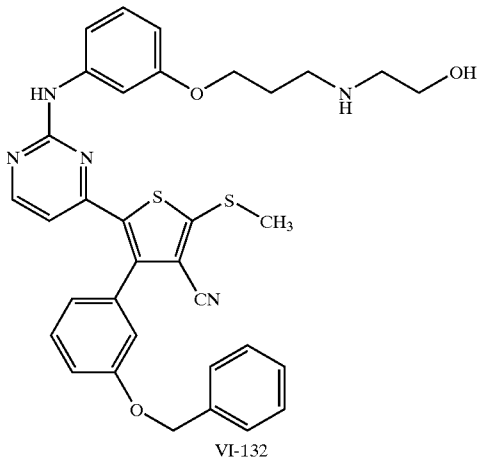
VI-132
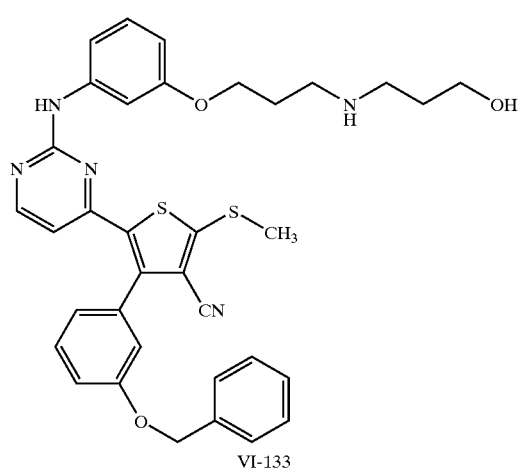
VI-133
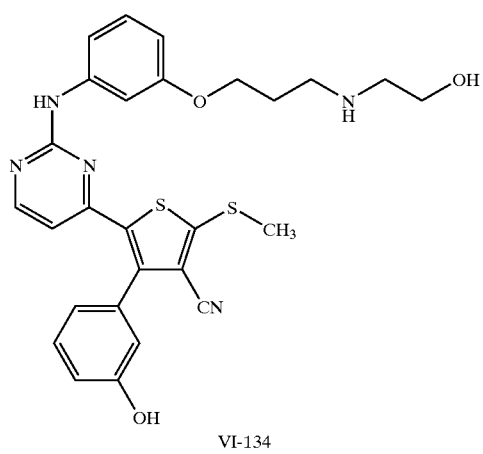
VI-134
TABLE 8-continued
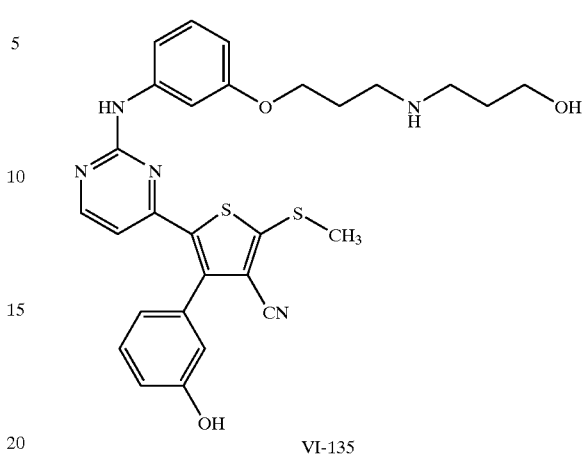
VI-135
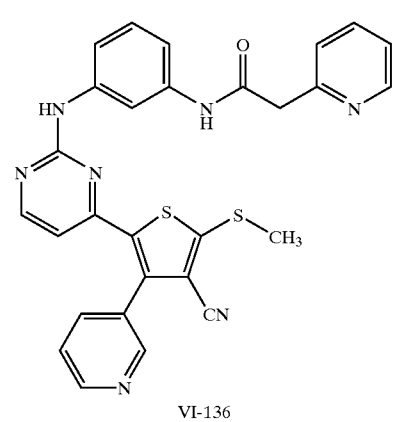
VI-136
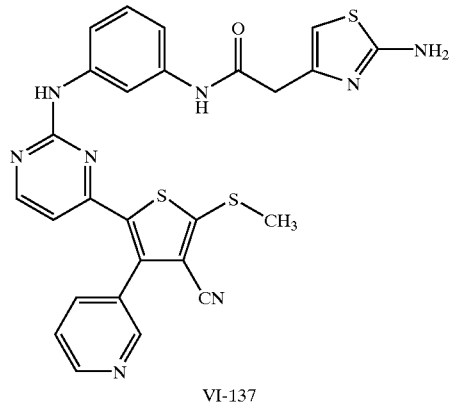
VI-137

TABLE 8-continued
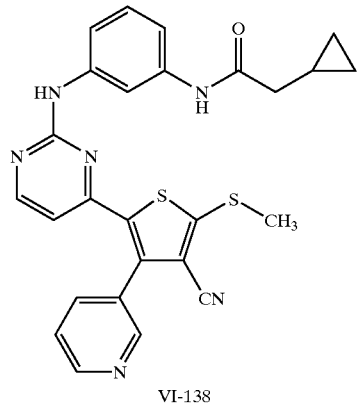
VI-138
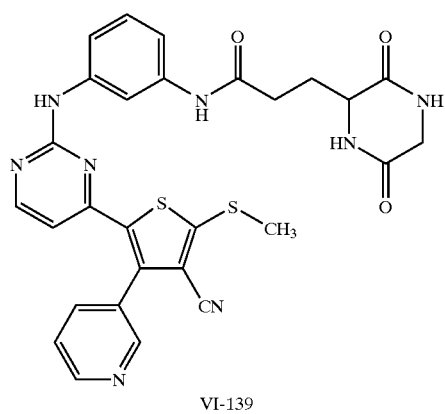
VI-139
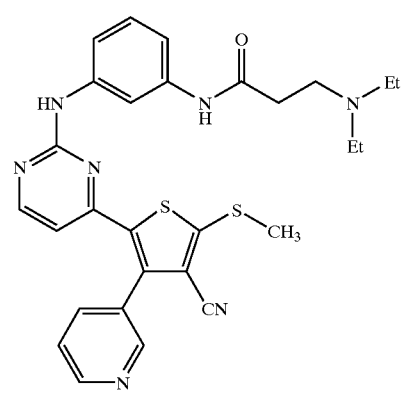
VI-140
TABLE 8-continued
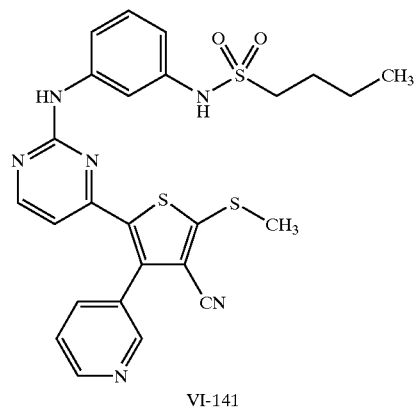
VI-141
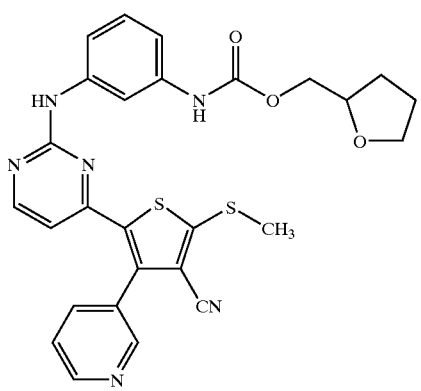
VI-142
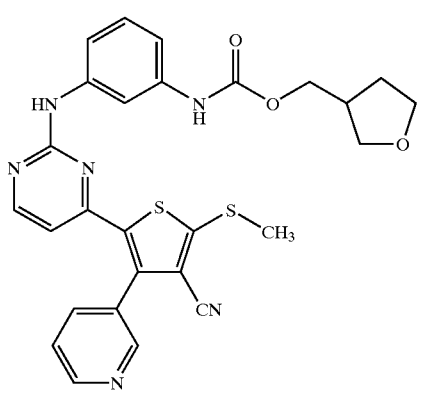
VI-143

TABLE 8-continued
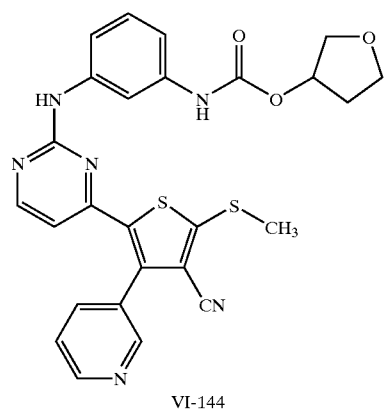
VI-144
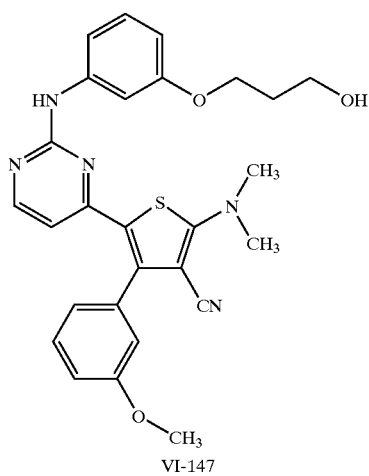
VI-147
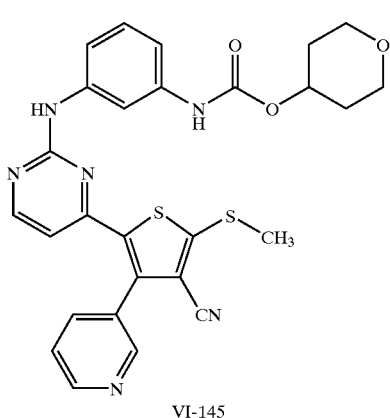
VI-145
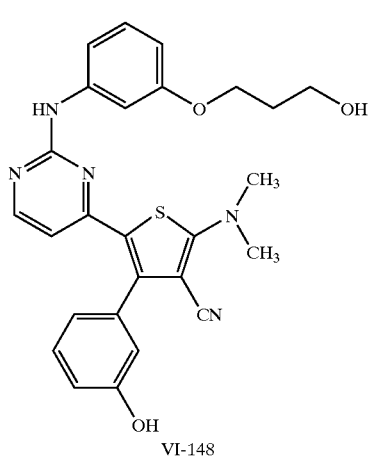
VI-148
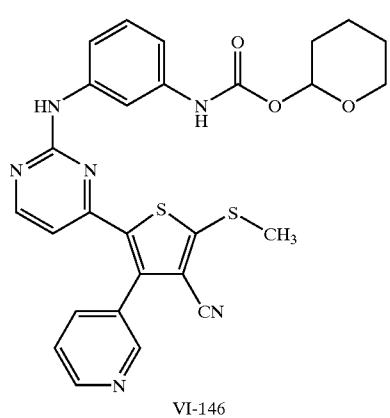
VI-146
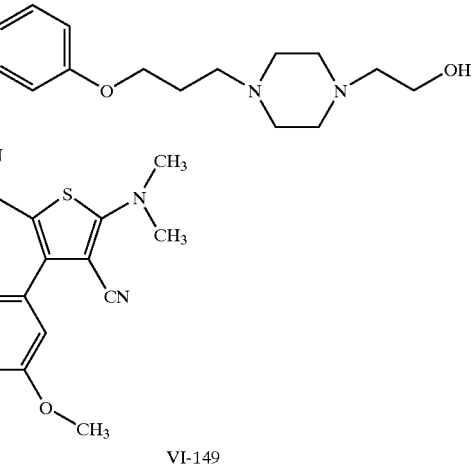
VI-149

TABLE 8-continued

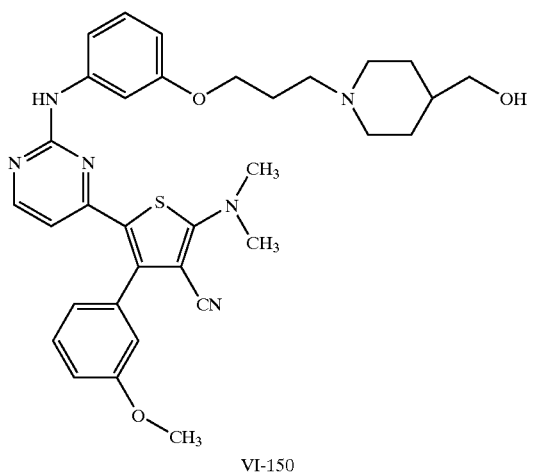

VI-150

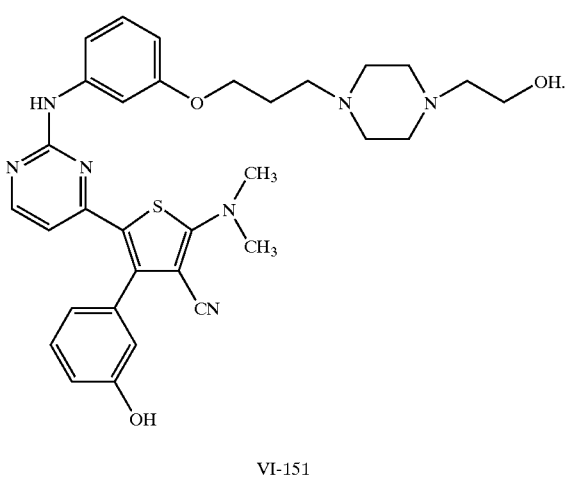

VI-151

15. A composition comprising an effective amount of a compound according to claim 1, and a pharmaceutically acceptable carrier, adjuvant, or vehicle.

16. The composition according to claim 15, additionally comprising a therapeutic agent selected from an anti-proliferative agent, an anti-inflammatory agent, an immunomodulatory agent, an agent for treating neurological disorders, an agent for treating cardiovascular disease, an agent for treating liver disease, an anti-viral agent, an agent for treating blood disorders, an agent for treating diabetes, or an agent for treating immunodeficiency disorders.

17. A composition for coating an implantable device comprising a compound according to claim 1 and a carrier suitable for coating said implantable device.

18. A method of inhibiting JNK, Lck, or Src kinase activity in a biological sample comprising the step of contacting said biological sample with:
  a) a compound according to claim 1; or
  b) a composition according to claim 15.

19. A method of treating or lessening the severity of an inflammatory disease, autoimmune disease, destructive bone disorder, proliferative disorder, infectious disease, neurodegenerative disease, allergy, reperfusion/ischemia in stroke, heart attack, angiogenic disorder, organ hypoxia, vascular hyperplasia, cardiac hypertrophy, thrombin-induced platelet aggregation or a condition associated with proinflammatory cytokines, comprising the step of administering to said patient a composition according to claim 15.

20. The method according to claim 19, wherein said method is used to treat or lessen the severity of an inflammatory disease selected from acute pancreatitis, chronic pancreatitis, asthma, allergies, or adult respiratory distress syndrome.

21. The method according to claim 20, wherein said method is used to treat or lessen the severity of an autoimmune disease selected from glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

22. The method according to claim 20, wherein said method is used to treat or lessen the severity of a destructive bone disorders selected from osteoarthritis, osteoporosis or multiple myeloma-related bone disorder.

23. The method according to claim 20, wherein said method is used to treat or lessen the severity of a proliferative disease selected from acute myelogenous leukemia, chronic myelogenous leukemia, metastatic melanoma, Kaposi's sarcoma, or multiple myeloma.

24. The method according to claim 20, wherein said method is used to treat or lessen the severity of a neurodegenerative disease selected from Alzheimer's disease, Parkinson's disease, amyotrophic lateral sclerosis, Huntington's disease, cerebral ischemia or neurodegenerative disease caused by traumatic injury, glutamate neurotoxicity or hypoxia.

25. The method according to claim 20, wherein said method is used to treat or lessen the severity of ischemia/reperfusion in stroke or myocardial ischemia, renal ischemia, heart attacks, organ hypoxia or thrombin-induced platelet aggregation.

26. The method according to claim 20, wherein said method is used to treat or lessen the severity of a condition associated with T-Cell activation or pathologic immune responses.

27. The method according to claim 20, wherein said method is used to treat or prevent an angiogenic disorder selected from solid tumors, ocular neovasculization, or infantile haemangiomas.

28. The method according to claim 20, wherein said disease is selected from hypercalcemia, restenosis, hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-Cell mediated hypersensitivity disease, Hashimoto's thyroiditis, Guillain-Barre syndrome, chronic obtructive pulmonary disorder, contact dermatitis, cancer, Paget's disease, asthma, ischemic or reperfusion injury, allergic disease, atopic dermatitis, or allergic rhinitis.

29. The method according to claim 28, wherein said disease is selected from hypercalcemia, osteoperosis, osteoarthritis, or sympomatic treatment of bone metastasis.

30. The method according to claim 19, wherein said disease is selected from autoimmune diseases, allergies, rheumatoid arthritis, and leukemia.

31. The method according to claim 19, comprising the additional step of administering to said patient an additional therapeutic agent selected from an anti-proliferative agent, an anti-inflammatory agent, an immunomodulatory agent, an agent for treating neurological disorders, an agent for treating cardiovascular disease, an agent for treating liver disease, an anti-viral agent, an agent for treating blood disorders, an agent for treating diabetes, or an agent for treating immunodeficiency disorders, wherein:

said additional therapeutic agent is appropriate for the disease being treated; and said additional therapeutic agent is administered together with said composition as a single dosage form or separately from said composition as part of a multiple dosage form.

* * * * *